US009580718B2

(12) United States Patent
Curtiss, III et al.

(10) Patent No.: US 9,580,718 B2
(45) Date of Patent: Feb. 28, 2017

(54) ATTENUATED LIVE BACTERIA WITH INCREASED ACID RESISTANCE AND METHODS OF USE THEREOF

(71) Applicant: Arizona Board of Regents on Behalf of Arizona State University, Tempe, AZ (US)

(72) Inventors: Roy Curtiss, III, Paradise Valley, AZ (US); Karen Brenneman, Phoenix, AZ (US); Kenneth Roland, Mesa, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 16 days.

(21) Appl. No.: 14/307,091

(22) Filed: Jun. 17, 2014

(65) Prior Publication Data

US 2014/0370057 A1   Dec. 18, 2014

Related U.S. Application Data

(60) Provisional application No. 61/836,140, filed on Jun. 17, 2013.

(51) Int. Cl.
| | |
|---|---|
| *A01N 63/00* | (2006.01) |
| *A01N 65/00* | (2009.01) |
| *C12N 1/00* | (2006.01) |
| *C12N 1/22* | (2006.01) |
| *C12N 15/74* | (2006.01) |
| *A61K 39/00* | (2006.01) |
| *A61K 39/112* | (2006.01) |
| *C12N 9/88* | (2006.01) |

(52) U.S. Cl.
CPC .............. *C12N 15/74* (2013.01); *A61K 39/00* (2013.01); *A61K 39/0275* (2013.01); *A61K 2039/522* (2013.01); *A61K 2039/542* (2013.01); *A61K 2039/552* (2013.01); *C12N 9/88* (2013.01)

(58) Field of Classification Search
CPC ..... C12N 15/67; C12N 15/70; C12N 15/8279
See application file for complete search history.

(56) References Cited

U.S. PATENT DOCUMENTS

| 4,190,495 A | 2/1980 | Curtiss, III |
| 4,888,170 A | 12/1989 | Curtiss, III |
| 4,968,619 A | 11/1990 | Curtiss, III |
| 5,210,035 A | 5/1993 | Stocker |

(Continued)

FOREIGN PATENT DOCUMENTS

| EP | 0315682 B1 | 12/1993 |
| EP | 0381706 B1 | 4/1995 |

(Continued)

OTHER PUBLICATIONS

Waterman et al., (J. Bacteriol. 2003. 185(15): 4644-4647).*

(Continued)

*Primary Examiner* — Ja'Na Hines
(74) *Attorney, Agent, or Firm* — McCarter & English, LLP; Elizabeth A. Hanley, Esq.; Marcie B. Clarke

(57) ABSTRACT

The present invention relates to inducing acid resistance in a bacterium and methods of increasing the acid resistance of an acid sensitive bacterium.

8 Claims, 19 Drawing Sheets
(2 of 19 Drawing Sheet(s) Filed in Color)

(56) References Cited

U.S. PATENT DOCUMENTS

| | | |
|---|---|---|
| 5,294,441 A | 3/1994 | Curtiss, III |
| 5,387,744 A | 2/1995 | Curtiss |
| 5,389,368 A | 2/1995 | Gurtiss, III |
| 5,424,065 A | 6/1995 | Curtiss, III |
| 5,468,485 A | 11/1995 | Curtiss, III |
| 5,536,658 A | 7/1996 | Shotts, Jr. et al. |
| 5,654,184 A | 8/1997 | Curtiss, III |
| 5,656,488 A | 8/1997 | Curtiss, III |
| 5,672,345 A | 9/1997 | Curtiss, III |
| 5,679,880 A | 10/1997 | Curtiss, III |
| 5,686,079 A | 11/1997 | Curtiss, III |
| 5,817,317 A | 10/1998 | Titball |
| 5,827,705 A | 10/1998 | Dean |
| 5,840,483 A | 11/1998 | Curtiss, III |
| 5,855,879 A | 1/1999 | Curtiss, III |
| 5,855,880 A | 1/1999 | Curtiss, III |
| 5,961,983 A | 10/1999 | Brey et al. |
| 6,024,961 A | 2/2000 | Curtiss, III |
| 6,180,614 B1 | 1/2001 | Davis |
| 6,248,329 B1 | 6/2001 | Chandrashekar et al. |
| 6,350,454 B1 | 2/2002 | Thune |
| 6,383,496 B1 | 5/2002 | Curtiss, III |
| 6,399,074 B1 | 6/2002 | Roland |
| 6,403,094 B1 | 6/2002 | Titball |
| 6,610,529 B1 | 8/2003 | Curtiss, III |
| 6,780,405 B1 | 8/2004 | Curtiss, III |
| 6,872,547 B1 | 3/2005 | Curtiss, III |
| 6,969,513 B2 | 11/2005 | Galen |
| 7,083,794 B2 | 8/2006 | Curtiss, III |
| 7,195,757 B2 | 3/2007 | Curtiss, III |
| 7,205,125 B2 | 4/2007 | Castillo |
| 7,341,860 B2 | 3/2008 | Curtiss, III |
| 7,871,604 B1 | 1/2011 | Curtiss, III |
| 7,968,101 B2 | 6/2011 | Kawaoka |
| 8,133,493 B2 | 3/2012 | Curtiss, III |
| 8,445,254 B2 | 5/2013 | Curtiss, III et al. |
| 8,465,755 B2 | 6/2013 | Curtiss, III et al. |
| 2003/0031683 A1 | 2/2003 | Curtiss, III |
| 2003/0175772 A1 | 9/2003 | Wang |
| 2004/0077556 A1 | 4/2004 | Chinery |
| 2004/0101531 A1 | 5/2004 | Curtiss, III |
| 2004/0120962 A1 | 6/2004 | Curtiss, III |
| 2004/0137003 A1 | 7/2004 | Curtiss, III |
| 2004/0203039 A1 | 10/2004 | Hensel |
| 2005/0036987 A1 | 2/2005 | Pawelek et al. |
| 2005/0106175 A1 | 5/2005 | Montanes |
| 2005/0106176 A1 | 5/2005 | Curtiss, III |
| 2005/0118193 A1 | 6/2005 | Andino-Pavlovsky et al. |
| 2006/0140975 A1 | 6/2006 | Curtiss, III |
| 2006/0171917 A1 | 8/2006 | Campbell |
| 2006/0206961 A1 | 9/2006 | Cirpus |
| 2006/0233829 A1 | 10/2006 | Curtiss, III |
| 2006/0234346 A1 | 10/2006 | Retallack |
| 2006/0275255 A1 | 12/2006 | Gudkov |
| 2007/0025981 A1 | 2/2007 | Szalay |
| 2008/0096809 A1 | 4/2008 | Shai |
| 2008/0248066 A1 | 10/2008 | Dubensky, Jr. |
| 2009/0175829 A1 | 7/2009 | Forbes et al. |
| 2010/0124558 A1* | 5/2010 | Curtiss, III ............ A61K 35/74 424/200.1 |
| 2010/0154293 A1 | 6/2010 | Hom et al. |
| 2010/0255022 A1 | 10/2010 | Prescott et al. |
| 2010/0285592 A1 | 11/2010 | Curtiss et al. |
| 2010/0317084 A1 | 12/2010 | Curtiss, III |
| 2011/0033501 A1 | 2/2011 | Curtiss, III et al. |
| 2011/0256181 A1 | 10/2011 | Curtiss et al. |
| 2011/0287052 A1 | 11/2011 | Curtiss, III et al. |
| 2012/0087946 A1 | 4/2012 | Curtiss, III |
| 2013/0004537 A1 | 1/2013 | Curtiss, III et al. |
| 2013/0171190 A1 | 7/2013 | Curtiss, III et al. |

FOREIGN PATENT DOCUMENTS

| | | | |
|---|---|---|---|
| EP | 0465560 B1 | 6/1996 | |
| EP | 0500699 B1 | 6/1998 | |
| EP | 0558631 B1 | 3/1999 | |
| EP | 0433372 B1 | 6/2002 | |
| EP | 1030690 B1 | 7/2002 | |
| EP | 0556333 B1 | 3/2003 | |
| EP | 1326960 B1 | 12/2004 | |
| EP | 0832255 B1 | 12/2005 | |
| EP | 1537214 B1 | 3/2006 | |
| EP | 1292687 B1 | 8/2006 | |
| JP | 2002223770 | * 8/2002 | ............ C12N 15/09 |
| WO | 88/09669 A1 | 12/1988 | |
| WO | 89/03427 A1 | 4/1989 | |
| WO | 90/02484 A1 | 3/1990 | |
| WO | 90/11687 A1 | 10/1990 | |
| WO | 90/11688 A1 | 10/1990 | |
| WO | 90/12086 A1 | 10/1990 | |
| WO | 91/06317 A1 | 5/1991 | |
| WO | 92/08486 A1 | 5/1992 | |
| WO | 92/09684 A1 | 6/1992 | |
| WO | 93/04202 A1 | 3/1993 | |
| WO | 94/24291 A2 | 10/1994 | |
| WO | 94/24291 A3 | 12/1994 | |
| WO | 96/40947 A1 | 12/1996 | |
| WO | 99/25387 A1 | 5/1999 | |
| WO | 01/83785 A2 | 11/2001 | |
| WO | 02/30457 A2 | 4/2002 | |
| WO | 01/83785 A3 | 6/2002 | |
| WO | 02/059292 A2 | 8/2002 | |
| WO | 02/030457 A3 | 1/2003 | |
| WO | 02/030457 A3 | 7/2003 | |
| WO | 02/059292 A3 | 7/2003 | |
| WO | 03/079792 A1 | 10/2003 | |
| WO | 03/096812 A1 | 11/2003 | |
| WO | 2004/020643 A2 | 3/2004 | |
| WO | 2004/020643 A3 | 4/2004 | |
| WO | 2005/001069 A1 | 1/2005 | |
| WO | 2012087483 A1 | 6/2008 | |
| WO | 2008/141226 A2 | 11/2008 | |
| WO | 2009/025888 A2 | 2/2009 | |
| WO | 2009/046449 A1 | 4/2009 | |
| WO | 2009/046451 A1 | 4/2009 | |
| WO | 2010/045620 A1 | 4/2010 | |
| WO | 2010/078584 A1 | 8/2010 | |
| WO | 2010/135563 A1 | 11/2010 | |
| WO | 2011/091291 A1 | 7/2011 | |
| WO | 2011/150421 A2 | 12/2011 | |

OTHER PUBLICATIONS

PCT/US2011/061896 (WO2012/087483)—International Search Report and Written Opinion of the International Searching Authority, Apr. 5, 2012.

Spellberg et al., Type 1/type 2 immunity in infectious diseases. Clin. Infect. Dis., 2001, pp. 76-102, vol. 32.

Schnaitman et al., Genetics of Lipopolysaccharide Biosynthesis in Enteric Bacteria. Microbiological Reviews, 1993, pp. 655-682, vol. 57, No. 3.

Byl et al, Sequence of the Genomore of *Salmonella* Bacteriophage P22. Journal of Bacteriology, 2000, pp. 6472-6484, vol. 182, 22.

Steel et al., Live attenuated influenza viruses containing NS1 truncations as vaccine candidates against H5N1 highly pathogenic avian influenza. J. Virol., 2009, pp. 1742-1753, vol. 83.

Tacket et al., Safety and immunogenicity in humans of an attenuated *Salmonella typhi* vaccine vector strain expressing plasmid-encoded hepatitis B antigens stabilized by the asd-balanced lethal vector system. Infect Immun, 1997, pp. 3381-3385, vol. 65.

Taubenberger et al., 1918 Influenza: the mother of all pandemics. Emerg. Infect. Dis., 2006, pp. 15-22, vol. 12.

Török et al., Accumulation of ppGpp in a relA mutant of *Escherichia coli* during amino acid starvation. J. Biol. Chem., 1980, pp. 3838-3840, vol. 255.

Tu et al., The PhoP/PhoQ two-component system stabilizes the alternative sigma factor RpoS in *Salmonella enterica*. Proc Natl Acad Sci U S A., 2006, pp. 13503-13508, vol. 103.

(56) References Cited

OTHER PUBLICATIONS

Tumpey et al., Characterization of the reconstructed 1918 Spanish influenza pandemic virus. Science, 2005, pp. 77-80, vol. 310.

Van Rossum et al., Host and bacterial factors contributing to the clearance of colonization by *Streptococcus pneumoniae* in a murine model. Infect Immun, 2005, pp. 7718-7726, vol. 73.

Van Velkinburgh et al., PhoP-PhoQ-regulated loci are required for enhanced bile resistance in *Salmonella* spp. Infect Immun, 1999, pp. 1614-1622, vol. 67.

Webster et al., Evolution and ecology of influenza A viruses. Microbiol Rev, 1992, pp. 152-179, vol. 56.

Wilmes-Riesenberg et al., Role of acid tolerance response in virulence of *Salmonella typhimurium*. Infect.Immun, 1996, pp. 1085-1092, vol. 64.

Wu et al., The mechanism underlying T cell help for induction of an antigen-specific in vivo humoral immune response to intact *Streptococcus pneumoniae* is dependent on the type of antigen. J Immunol, 2002, pp. 5551-5557, vol. 168.

Zahn, Overexpression of an mRNA dependent on rare codons inhibits protein synthesis and cell growth. J Bacteriol, 1996, pp. 2926-2933, vol. 178, No. 10.

Zhang et al., Characterization and immunogenicity of *Salmonella typhimurium* SL1344 and UK-1 crp and cdt deletion mutants. Infect. Immun., 1997, pp. 5381-5387, vol. 65.

Zobel et al., RNA polymerase I catalysed transcription of insert viral cDNA. Nucleic. Acids. Res., 1993, pp. 3607-3614, vol. 21.

Baek et al., Leucine-Responsive Regulator Protein (Lrp) Acts as a Virulence Respressor in *Salmonella enterica* Servoar Typhimurium. Journal of Bacteriology, 2009, pp. 1278-1292, vol. 191, No. 4.

U.S. Appl. No. 12/615,872, Office Action dated Mar. 14, 2012.

Collins et al, Mutation at rfc or pmi Attenuate *Salmonella typhimurium* Virulence for Mice. Infect and Immun, 1991, pp. 1079-1085, vol. 59, No. 3.

Curtiss et al., Stabilization of Recombinant Avirulent Vaccine Strains in vivo. Res. Microbiol., 1990, pp. 797-805, vol. 141.

Curtiss et al, Avirulent *Salmonell typhimurim* cyc crp oral vaccine strains expressing a streptococcal colonization and virulence antigen. Vaccine, 1988, pp. 155-160, vol. 6.

Darzins et al., Nucleotide sequence analysis of the phosphomannose isomerase gene (pmi) of Pseudomonas aeruginose and comparison with the corresponding *Escherichia coli* gene manA. Gene, 1986, pp. 293-302, vol. 42.

Doggett et al., Immune Responses to *Streptococcus sobrinus* Surface Protein Antigen A Expressed by Recombinant *Salmonella typhimurium*. Infect and Immun, 1993, pp. 1859-1866, vol. 61, No. 5.

Egan et al., A Regulatory Cascade in the Induction of rhaBAD. J. Mol. Biol., 1993, pp. 87-98, vol. 234.

Guzman et al., Tight regulations, Modulations, and High-Level Expression by Vectors Containing the Arabinose Pbad Promotor. Journal of Bacteriology, 1995, pp. 4121-4130, vol. 177, No. 14.

Kennedy et al., Attenuation and Immunogenicity of cya crp Derivatives of *Salmonella choleraeuis* in Pigs. Infect Immun, 1999, pp. 4628-4636, vol. 67, No. 9.

Nickerson et al., Role of Sigma Factor RpoS in Initial Stages of *Salmonella typhimurium* Infection. Infect Immun, 1997, p. 1814-23, vol. 65, No. 5.

Schodel et al., Hybrid Hepatitis B Virus Core-Pre-S Proteins Synthesized in Avirulent *Salmonella typhimurium* and *Salmonella typhi* for Oral Vaccination. Infect Immun, 1994, pp. 1669-1676, vol. 62, No. 5.

Schodel, Recombinant Avirulent Salmonellae as Oral Vaccine Carriers. Infection, 1992, vol. 20, pp. 1-12, No. 1.

Siegele et al., Gene Expression from plasmids containing the araBAD promoter at subsaturating inducer concentrations represents mixed populations. PNAS, 1997, pp. 8168-8172, vol. 94.

Song et al., Organization and Regulation of the d-Xylose Operons in *Escherichia coli* K-12: XylR Acts as a Transcriptional Activator. Journal of Bacteriology, 1997, pp. 7025-7032, vol. 179, No. 22.

Srinivasan et al., Oral Immunization with Attenuated *Salmonella* Expressing Human Sperm Antigen Induces Antibodies in Serum and the Reproductive Tract. Biology of Reproduction, 1995, p. 462-71 vol. 53.

PCT/US2008/063293 (WO 2009/025888)—International Search Report and Written Opinion of the International Searching Authority, Feb. 12, 2009.

Mesika et al., A Regulated, NFkB—Assisted Import of Plasmid DNA into Mammalian Cell Nuclei, Molecular Therapy, vol. 3, No. 5, May 2001, pp. 653-657.

Quenee, et al., Yersinia pestis caf1 Variants and the Limits of Plague Vaccine Protection, Infection and Immunity, May 2008, vol. 76, No. 5, pp. 2025-2036.

U.S. Appl. No. 13/088,141, Office Action dated Dec. 6, 2012.

U.S. Appl. No. 13/006,072, Office Action dated Dec. 11, 2012.

Kong. Improving DNA Vaccine Vector for Efficient Vaccine Delivery using Live Attenuated Bacterial Carrier. American Society for Microbiology, T-010, 2008, vol. 108, p. 668.

Whitworth et al., Expression of the Rickettsia prowazekii pld or tlyC Gene in *Salmonella enterica* Serovar Typhimurium Mediates Phagosomal Escape, Infection and Immunity, 2005, vol. 73(10), pp. 6668-6673.

Folkesson et al., Components of the peptidoglycan-recycling pathway modulate invasion and intracellular survival of *Salmonella enterica* serovar Typhimurium. Cellular Microbiology, 2005, vol. 7(1) pp. 147-155.

U.S. Appl. No. 12/599,655, Office Action dated Mar. 12, 2013.

U.S. Appl. No. 12/681,711, Office Action dated Nov. 28, 2012.

U.S. Appl. No. 12/789,869, Office Action dated Jun. 3, 2014.

U.S. Appl. No. 13/088,141, Office Action dated Apr. 24, 2014.

U.S. Appl. No. 13/574,718, Office Action dated Sep. 6, 2013.

U.S. Appl. No. 13/574,718, Office Action dated Apr. 28, 2014.

Takaya, A. et al, The ATP-Dependent Lon Protease of *Salmonella enterica* Serovar Typhimurium Regulates Invasion and Expression of Genes Carried on *Salmonella* Pathogenicity Island 1. Journal of Bacteriology. Jan. 2002, vol. 184(1), pp. 224-232: abstract.

Navasa, M. et al., Temperature has reciprocal effect on colanic acid and polysialic acid biosynthesis in *E. Coli* K92. Appl. Microbiol Biotechnol., Jan. 13, 2009, vol. 82, pp. 721-729.

Sheehan et al., Generation and characterization of hamster monoclonal antibodies that neutralize murine tumor necrosis factors. J Immunol, 1989, pp. 3884-3893, vol. 142.

Sizemore et al., Attenuated bacteria as a DNA delivery vehicle for DNA-mediated immunization. Vaccine, 1997, pp. 804-807, vol. 15.

Snapper et al., Distinct types of T-cell help for the induction of a humoral immune response to *Streptococcus pneumoniae*. Trends Immunol, 2001, pp. 308-311, vol. 22.

Sodeinde et al., Plasminogen activator/coagulase gene of Yersinia pestis is responsible for degradation of plasmid-encoded outer membrane proteins. Infect Immun, 1988, pp. 2749-2752, vol. 56.

Sternberg et al., Bacteriophage-mediated nucleic acid sequenceralized transduction in *Escherichia coli* and *Salmonella typhimurium*. Methods Enzymol, 1991, pp. 18-43, vol. 204.

Straley et al., Virulence genes regulated at the transcriptional level by Ca2+ in Yersinia pestis include structural genes for outer membrane proteins. Infect Immun, 1986, pp. 445-454, vol. 51.

Sun et al., The role of relA and spoT in Yersinia pestis KIM5+ pathogenicity. PLoS One, 2009, pp. E6720, vol. 4.

Thompson et al., The bacterial signal molecule, ppGpp, mediates the environmental regulation of both the invasion and intracellular virulence gene programs of *Salmonella*. J Biol Chem, 2006, pp. 30112-30121, vol. 281.

Une et al., In vivo comparison of avirulent Vwa- and Pgm- or Pstr phenotypes of Yersiniae. Infect Immun, 1984, pp. 895-900, vol. 43.

Uzzau et al., Epitope tagging of chromosomal genes in *Salmonella*. Proc Natl Acad Sci U S A, 2001, pp. 15264-15269, vol. 98.

Viboud et al., Yersinia outer proteins: role in modulation of host cell signaling responses and pathogenesis. Annu Rev Microbiol, 2005, pp. 69-89, vol. 59.

Wasserman et al., Two alanine racemase genes in *Salmonella typhimurium* that differ in structure and function. J. Bacteriol., 1983, pp. 1439-1450, vol. 153.

(56) References Cited

OTHER PUBLICATIONS

Whitfield, Biosynthesis and assembly of capsular polysaccharides in *Escherichia coli*. Annu Rev. Biochem., 2006, pp. 39-68, vol. 75.
Winter et al., The *Salmonella enterica* serotype Typhi regulator TviA reduces interleukin-8 production in intestinal epithelial cells by repressing flagellin secretion. Cell Microbiol, 2008, pp. 247-261, vol. 10, No. 1.
Wolf et al., Evolution of aminoacyl tRNA synthetases—analysis of unique domain architectures and phylogenetic trees reveals a complex history of horizontal gene transfer events. Genome Res, 1999, pp. 689-710, vol. 9.
Xiao et al., Residual guanosine 39,59-bispyrophosphate synthetic activity of reIA null mutants can be eliminated by spoT null mutations. J Biol Chem, 1991, pp. 5980-5990, vol. 266.
Zahorchak et al., Effect of exogenous nucleotides on Ca2+ dependence and V antigen synthesis in Yersinia pestis. Infect Immun, 1982, pp. 953-959, vol. 38.
Zhang et al., A "one-plasmid" system to generate influenza virus in cultured chicken cells for potential use in influenza vaccine. J. Virol., 2009, pp. 9296-9303, vol. 83.
Zhang et al., Transcription activation parameters at ara pBAD. J Mol Biol, 1996, pp. 14-24, vol. 258, No. 1.
Zinkernagel et al., Antigen localisation regulates immune responses in a dose- and time-dependent fashion: a geographical view of immune reactivity. Immunol Rev, 1997, pp. 199-209, vol. 156.
Briles et al., PspA, a protection-eliciting pneumococcal protein: immunogenicity of isolated native PspA in mice. Vaccine, 1996, pp. 858-867, vol. 14.
Hanisch, et al, The Ralstonia eutropha H16 phasin PhaP1 is targeted to intracellular triacylglycerol inclusions in Rhodococcus opacus PD630 and Mycobacterium smegmatis mc2155, and provides an anchor to target other proteins. Microbiology, 2006, pp. 3271-3280, vol. 152.
Kong et al, Regulated Delayed Expression of rfaH in an Attenuated *Salmonella enterica* Serovar Typhimurium Vaccine Enhances Immunogenicity of Outer Membrane Proteins and Heterologous Antigen. Infec Immun. 2009, pp. 5572-5582, vol. 77, No. 12.
U.S. Appl. No. 13/302,575, Office Action dated Sep. 25, 2012.
Morita et al., Antibacterial Activity of Bacillus amyloliquefaciencs Phage Endolysin without Holin Conjugation. Journal of Biosciences and Bioengineering, 2001, pp. 469-473, vol. 91, No. 5.
U.S. Appl. No. 13/302,575, Office Action dated Jun. 18, 2013.
Stevens, Immunization with the C-Domain of alpha-Toxin Prevents Lethal Infection, Localizes Tissue Injury, and Promotes Host Responses to Challenge with Clostridium perfringens. JID, 2004, pp. 767-773, vol. 190.
Verjan et al, Genetic Loci of Major Antigenic Protein Genes of Edwardsiella tarda. Applied and Environmental Microbiology, 2005, pp. 5654-5658, vol. 71, No. 9.
U.S. Appl. No. 12/599,655 Office Action dated Jul. 2, 2012.
U.S. Appl. No. 12/681,721, Office Action dated May 24, 2012.
U.S. Appl. No. 12/759,842, Office Action dated Jun. 7, 2012.
Ellis, New Technologies for Making Vaccines. Vaccines, 1988, pp. 568-574, Chapter 29, WB Saunders Company, United States.
Greenspan et al, Defining eptiopes: It's not as easy as it seems. Nature Biotechnology, 1999, pp. 936-937, vol. 17.
Houghten et al, Relative Importance of Position and Individual Amino Acid Residues in Peptide Antigen-Antibody Interactions: Implications in the Mechanism of Antigenic Drift and Antigenic Shift. Vaccines86, 1986, pp. 21-25; Cold Spring Harbor Laboratory.
U.S. Appl. No. 12/615,872 Office Action dated Oct. 23, 2012.
Bittner et al., RpoS and RpoN are involved in the growth-dependent regulation of rfaH transcription and O antigen expression in *Salmonella enterica* serovar Typhi, Microbial Pathogenisis. vol. 36, 2004 (p. 19).
Kong et al, *Salmonella* Synthesizing 1-Monophosphorylated Lipopolysaccharide Exhibits Low Endotoxic Activity while Retaining its Immunogenicity. J. Immunol. Jun. 1, 2011, vol. 187, pp. 412-423.

Moreno et al., *Salmonella* as Live Trojan Horse for Vaccine Development and Cancer Gene Therapy. Current Gene Therapy, 2010, 10: 56-76.
U.S. Appl. No. 13/898,241 Office Action dated Apr. 17, 2014.
Liu et al.—CO2—limitation—inducible Green Recovery of fatty acids from cyanobacterial biomass. PNAS, vol. 108, 2011, pp. 6905-6908.
Liu et al., Nickel-inducible lysis system in Synechocystis sp. PCC 6803. PNAS, vol. 106, 2009, pp. 21550-21554.
Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.
Amann et al., Tightly regulated tac promoter vectors useful for the expression of unfused and fused proteins in *Escherichia coli*. Nucleic acid sequence, 1988. pp. 301-315, vol. 69, No. 2.
Anderson et al., Delivery of the Pertactin/P.69 polypeptide of Bordetella pertussis using an attenuated *Salmonella typhimurium* vaccine strain: expression levels and immune response. Vaccine, 1996, pp. 1384-1390 , vol. 14, No. 14.
Aravind et al., The HD domain defines a new superfamily of metal-dependent phosphohydrolases. Trends Biochem Sci, 1998, pp. 469-472, vol. 23.
Arricau et al., The RcsB-RcsC regulatory system of *Salmonella typhi* differentially modulates the expression of invasion proteins, flagellin and Vi antigen in response to osmolarity., Mol Microbiol, 1998, pp. 85-50, vol. 29, No. 3.
Arulanandam et al., Intranasal vaccination with pneumococcal surface protein A and interleukin-12 augments antibody-mediated opsonization and protective immunity against *Streptococcus pneumoniae* infection. Infect Immun, 2001, pp. 6718-6724, vol. 69.
Audia et al., Breaking through the acid barrier: an orchestrated response to proton stress by enteric bacteria. Int J Med Microbiol, 2001, pp. 97-106, vol. 291.
Battesti et al., Acyl carrier protein/SpoT interaction, the switch linking SpoT-dependent stress response to fatty acid metabolism. Mol Microbiol, 2006, pp. 1048-1063, vol. 62.
Blattner et al., The complete genome sequence of *Escherichia coli* K-12. Science, 1997, pp. 1453-1474, vol. 277.
Branger et al., Oral vaccination with different antigens from Yersinia pestis KIM delivered by live attenuated *Salmonella typhimurium* elicits a protective immune response against plague. Adv Exp Med Biol, 2007, pp. 387-399, vol. 603.
Briles et al. The potential for using protein vaccines to protect against otitis media caused by *Streptococcus pneumoniae*. Vaccine, 2001, pp. S87-S95, vol. 19, Suppl 1.
Brubaker, Interleukin-10 and inhibition of innate immunity to Yersiniae: roles of Yops and LcrV (V antigen). Infect Immun, 2003, pp. 3673-3681, vol. 71.
Brubaker, The Vwa+ virulence factor of Yersiniae: the molecular basis of the attendant nutritional requirement for Ca2+. Rev Infect Dis, 1983,pp. S748-S758, vol. 5, Suppl 4.
Brumell et al., (2004) *Salmonella* redirects phagosomal maturation. Curr Opin Microbiol, 2004, pp. 78-84, vol. 7.
Cárdenas et al., Oral immunization using live attenuated *Salmonella* spp. as carriers of foreign antigens. Clin. Microbiol. Rev., 1992, pp. 328-342, vol. 5, No. 3.
Charnetzky et al., RNA synthesis in Yersinia pestis during growth restriction in calcium-deficient medium. J Bacteriol, 1982, pp. 108-195, vol. 149.
Chatfield et al., Use of the nirB promoter to direct the stable expression of heterologous antigens in *Salmonella* oral vaccine strains: development of a single-dose oral tetanus vaccine. Biotechnology (N Y), 1992, pp. 888-892, vol. 10, No. 8.
Cheng et al., Simultaneous analyses of neutral carbohydrates and amino sugars in freshwaters with HPLC—PAD. J. Chromatogr. Sci., 2003, pp. 434-438, vol. 41.
Chipman et al., The ACT domain family. Curr Opin Struct Biol, 2001, pp. 694-700, vol. 11.
Chromy et al., Proteomic characterization of Yersinia pestis virulence. J Bacteriol, 2005, pp. 8172-8180, vol. 187.

(56) References Cited

OTHER PUBLICATIONS

Coombes et al., SseL Is a *Salmonella*-Specific Translocated Effector Integrated into the SsrB-Controlled *Salmonella* Pathogenicity Island 2 Type III Secretion System. Infection and Immunity, 2007, pp. 574-580, vol. 75, No. 2.
Cornelis et al., The virulence plasmid of Yersinia, an antihost genome. Microbiol Mol Biol Rev, 1998, pp. 1315-1352, vol. 62.
Curtiss et al. Nonrecombinant and recombinant avirulent *Salmonella* vaccines for poultry. Vet Immunol Immunopathol, 1996, pp. 365-372, vol. 54.
Curtiss et al., Live oral avirulent *Salmonella* vaccines. Vet. Microbiol., 1993, pp. 397-405, vol. 37.
Curtiss et al., Recombinant *Salmonella* vectors in vaccine development. Dev Biol Stand., 1994, pp. 23-33, vol. 82.
Datsenko et al., One-step inactivation of chromosomal genes in *Escherichia coli* K-12 using PCR products. Proc Natl Acad Sci U S A, 2000, pp. 6640-6645, vol. 97.
Davison, Towards safer vectors for the field release of recombinant bacteria. Environ. Biosafety Res., 2002, pp. 9-18, vol. 1.
De Groote et al., Homocysteine antagonism of nitric oxide-related cytostasis in *Salmonella typhimurium*. Science, 1996, pp. 414-417, vol. 272.
Dekruyff et al., Induction of immunoglobulin synthesis by CD4+ T cell clones. Seminars in Immunology, 1993, pp. 421-430, vol. 5.
Del Beccaro et al., Bacteriology of acute otitis media: a new perspective. J Pediatr, 1992, pp. 81-84, vol. 120.
Deng et al., Genome sequence of Yersinia pestis Kim. J Bacteriol, 2002, pp. 4601-4611, vol. 184.
Doggett et al., Delivery of antigens by recombinant avirulent *Salmonella* strains. Adv. Exp. Med. Biol., 1992, pp. 165-173, vol. 327.
Doublet et al., The murI gene of *Escherichia coli* is an essential gene that encodes a glutamate racemase activity. J. Bacteriol., 1993, pp. 2970-2979, vol. 175.
Dubnau, DNA uptake in bacteria. Annu. Rev. Microbiol., 1999, pp. 217-244, vol. 53.
Edwards et al., Improved allelic exchange vectors and their use to analyze 987P fimbria nucleic acid sequence expression. Gene, 1998, pp. 149-157, vol. 207, No. 2.
Fooks, Development of oral vaccines for human use. Curr Opin Mol Ther, 2000, pp. 80-86, vol. 2, No. 1.
Foster et al., How *Salmonella* survive against the odds. Annu Rev Microbiol, 1995, pp. 145-174, vol. 49.
Galen et al., Can a 'flawless' live vector vaccine strain be engineered? Trends Microbiol, 2001, pp. 372-376, vol. 9, No. 8.
Garmory et al., The Use of Live Attenuated Bacteria as a Delivery System for Heterologous Antigens. Journal of Drug Targeting, 2003, pp. 471, vol. 11.
Garzon et al., recB recJ mutants of *Salmonella typhimurium* are deficient in transductional recombination, DNA repair and plasmid maintenance. Mol. Gen. Genet., 1996, pp. 570-580, vol. 250.
Gentry et al., Mutational analysis of the *Escherichia coli* spoT gene identifies distinct but overlapping regions involved in ppGpp synthesis and degradation. Mol Microbiol, 1996, pp. 1373-1384, vol. 19.
Gentschev et al., The *E. coli* alpha-hemolysin secretion system and its use in vaccine development. Trends Microbiol, 2002, pp. 39-45, vol. 10, No. 1.
Giannella et al., Gastric acidity and cholera. Ann Intern Med, 1973, p. 780, vol. 78.
Gilbert, The lac repressor and the lac operator. Ciba Found Symp, 1972, pp. 24-59, vol. 7.
Gong et al., Characterization of the Yersinia pestis Yfu ABC inorganic iron transport system. Infect Immun, 2001, pp. 2829-2837, vol. 69.
Gor et al., TH1-TH2: a Procrustean paradigm. Nat Immunol, 2003, p. 503-5, vol. 4.
Grillot-Courvalin et al., Functional gene transfer from intracellular bacteria to mammalian cells. Nat. Biotechnol., 1998, pp. 862-866, vol. 16.

Guerrant et al., Magnitude and Impact of Diarrheal Diseases. Arch. Med. Res., 2002, pp. 351-355, vol. 33.
Gunn, Mechanisms of bacterial resistance and response to bile. Microbes Infect, 2000, pp. 907-913, vol. 2.
Hengge-Aronis et al., Identification and molecular analysis of glgS, a novel growth-phase-regulated and rpoS-dependent gene involved in glycogen synthesis in *Escherichia coli*. Mol Microbiol, 1992, pp. 1877-1886, vol. 6.
Hess et al., Secretion of different listeriolysin cognates by recombinant attenuated *Salmonella typhimurium*: superior efficacy of haemolytic over non-haemolytic constructs after oral vaccination. Microbes Infect., 2000, pp. 1799-1806, vol. 2.
Hohmann et al., Evaluation of a phoP/phoQ-deleted, aroA-deleted live oral *Salmonella typhi* vaccine strain in human volunteers. Vaccine, 1996, pp. 19-24, vol. 14.
Hu et al., The inducible lac operator-repressor system is functional in mammalian cells. Cell, 1987, pp. 555-566, vol. 48, No. 4.
Hu et al., The inducible lac operator-repressor system is functional for control of expression of injected DNA in Xenopus oocytes. Gene, 1988, pp. 301-313, vol. 62, No. 2.
Huang et al., Genome-wide screen of *Salmonella* nucleic acid sequences expressed during infection in pigs, using in vivo expression technology. Appl Environ Microbiol, 2007, pp. 7522-7530, vol. 73, No. 23.
Iannelli et al., Allelic variation in the highly polymorphic locus pspC of *Streptococcus pneumoniae*. Gene, 2002, pp. 63-71, vol. 284.
In Soo Lee et al., The stationary-phase sigma factor sS (RpoS) is required for a sustained acid tolerance response in virulent *Salmonella typhimurium*. Molecular Microbiology, 1995, pp. 155-167, vol. 17.
Isoda et al., Expression of a Porphyromonas gingivalis hemagglutinin on the surface of a *Salmonella* vaccine vector. Vaccine, 2007, pp. 117-126, vol. 25, No. 1.
Ivancic-Bace et al, Effects of recJ, recQ, and recFOR mutations on recombination in nuclease-deficient recB recD double mutants of *Escherichia coli*. J. Bacteriol., 2005, pp. 1350-1356, vol. 187.
Kaufmann et al., Impact of intracellular location of and antigen display by intracellular bacteria: implications for vaccine development. Immunol. Lett., 1999, pp. 81-84, vol. 65.
Khan et al., Immunogenicity and protective efficacy of DnaJ (hsp40) of *Streptococcus pneumoniae* against lethal infection in mice. Vaccine, 2006, pp. 6225-6231, vol. 24.
Kim et al., Direct transcriptional control of the plasminogen activator gene of Yersinia pestis by the cyclic AMP receptor protein. J Bacteriol, 2007, pp. 8890-8900, vol. 189.
Kolodrubetz et al., Regulation of the L-arabinose transport operons in *Escherichia coli*. J Mol Biol, 1981, pp. 215-227, vol. 151, No. 2.
Kwon et al., *Salmonella*-based vaccines for infectious diseases. Expert Review of Vaccines, 2007, pp. 147-152, vol. 6.
Lange et al., Identification of a central regulator of stationary-phase gene expression in *Escherichia coli*. Mol Microbiol, 1991, pp. 49-59, vol. 5.
Lee et al., Regulation of L-arabinose transport in *Salmonella typhimurium* LT2. Mol Gen Genet, 1982, pp. 136-141, vol. 185, No. 1.
Lee et al., Surface-displayed viral antigens on *Salmonella* carrier vaccine. Nat Biotechnol, 2000, pp. 645-648, vol. 18, No. 6.
Lewis, The lac repressor. C R Biol, 2005, pp. 521-548, vol. 328, No. 6.
Lobell et al., AraC-DNA looping: orientation and distance-dependent loop breaking by the cyclic AMP receptor protein. J Mol Biol, 1991, pp. 45-54, vol. 218.
Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.
Loessner et al., Bacteria-mediated DNA transfer in gene therapy and vaccination. Expert. Opin. Biol. Ther., 2004, pp. 157-168, vol. 4.
Loessner et al., Remote control of tumour-targeted *Salmonella enterica* serovar Typhimurium by the use of L-arabinose as inducer of bacterial gene expression in vivo. Cell Microbiol, 2007, pp. 1529-1537, vol. 9.

(56) References Cited

OTHER PUBLICATIONS

Marshall et al., Use of the stationary phase inducible promoters, spv and dps, to drive heterologous antigen expression in *Salmonella* vaccine strains. Vaccine, 2000, pp. 1298-1306, vol. 18, No. 14.
Medina et al., Use of live bacterial vaccine vectors for antigen delivery: potential and limitations. Vaccine, 2001, pp. 1573-1580, vol. 19.
Mehigh et al., Expression of the low calcium response in Yersinia pestis. Microb Pathog, 1989, pp. 203-217, vol. 6.
Moore et al., Enhanced protective immunity against pneumococcal infection with PspA DNA and protein. Vaccine, 2006, p. 5755, vol. 24.
Mossing et al., Upstream operators enhance repression of the lac promoter. Science, 1986, pp. 889-892, vol. 233, No. 4766.
Motin et al., Passive immunity to Yersiniae mediated by anti-recombinant V antigen and protein A-V antigen fusion peptide. Infect Immun, 1994, pp. 4192-4201, vol. 62.
Muller et al., Repression of lac promoter as a function of distance, phase and quality of an auxiliary lac operator. J Mol Biol, 1996, pp. 21-29, vol. 257, No. 1.
Muller-Hill et al., Mutants that mke more lac repressor. Proc Natl Acad Sci U S A, 1968, pp. 1259-1264, vol. 59, No. 4.
Muller-Hill, Lac repressor and lac operator. Prog Biophys Mol Biol, 1975, pp. 227-252, vol. 30, No. 2-3.
Nabors et al., Immunization of healthy adults with a single recombinant pneumococcal surface protein A (PspA) variant stimulates broadly cross-reactive antibodies to heterologous PspA molecules. Vaccine, 2000, p. 1743, vol. 18.
Nakayama et al., Construction of an Asd+ expression-cloning vector: stable maintenance and high level expression of cloned nucleic acid sequences in a *Salmonella vaccine* strain. BioTechnology, 1988, pp. 693-697, vol. 6.
Nedialkov et al., Resistance to lipopolysaccharide mediated by the Yersinia pestis V antigen-polyhistidine fusion peptide: amplification of interleukin-10. Infect Immun, 1997, pp. 1196-1203, vol. 65.
Neutra et al., Antigen sampling across epithelial barriers and induction of mucosal immune responses. Annu Rev Immunol, 1996, pp. 275-300, vol. 14.
O'Callaghan et al., High efficiency transformation of *Salmonella typhimurium* and *Salmonella typhi* by electroporation. Mol Gen Genet, 1990, pp. 156-158, vol. 223, No. 1.
Ortqvist et al., Randomised trial of 23-valent pneumococcal capsular polysaccharide vaccine in prevention of pneumonia in middle-aged and elderly people. Swedish Pneumococcal Vaccination Study Group. Lancet, 1998, pp. 399-403, vol. 351.
Perry et al., Temperature regulation of the hemin storage (Hms+) phenotype of Yersinia pestis is posttranscriptional. J Bacteriol, 2004, pp. 1638-1647, vol. 186.
Petersen et al., Essential role for cyclic AMP and its receptor protein in Yersinia enterocolitica virulence. Infect Immun, 2004, pp. 3665-3672, vol. 70.
Ramarathinam et al., *Salmonella Typhimurium* induces IFN-gamma production in murine splenocytes. Role of natural killer cells and macrophages. J Immunol, 1993, pp. 3973-3981, vol. 150.
Raupach et al., Bacterial virulence, proinflammatory cytokines and host immunity: how to choose the appropriate *Salmonella* vaccine strain? Microbes and Infection, 2001, p. 1261, vol. 3.
Roland et al., Construction and evaluation of a delta cya delta crp *Salmonella typhimurium* strain expressing avian pathogenic *Escherichia coli* 078 LPS as a vaccine to prevent airsacculitis in chickens. Avian Dis, 1999, pp. 429-441, vol. 43, No. 3.
Sarubbi et al., (1989) Characterization of the spoT gene of *Escherichia coli*. J Biol Chem, 1989, pp. 15074-15082, vol. 264.
Schmieger et al., Altered cotransduction frequencies exhibited by HT-mutants of *Salmonella*-phage P22. Mol Gen Genet, 1976, pp. 307-309, vol. 143.
Schmieger, Phage P22-mutants with increased or decreased transduction abilities. Mol Gen Genet, 1972, pp. 75-88, vol. 119.
Schödel et al., Hybrid hepatitis B virus core antigen as a vaccine carrier moiety. II. Expression in avirulent *Salmonella* spp. For mucosal immunization. Adv Exp Med Biol., 1996, pp. 15-21, vol. 397.
Schodel, Prospects for oral vaccination using recombinant bacteria expressing viral epitopes. Adv. Virus Res., 1992, pp. 409-446, vol. 41.
Schwyn et al., Universal chemical assay for the detection and determination of siderophores. Analytical Biochemistry, 1987, p. 47, vol. 160.
Sedgwick et al., A solid-phase immunoenzymatic technique for the enumeration of specific antibody-secreting cells. Journal of Immunological Methods, 1983, p. 301, vol. 57.
Shalaby, Development of oral vaccines to stimulate mucosal and systemic immunity: barriers and novel strategies. Clin Immunol Immunopathol, 1995, pp. 127-134, vol. 74, No. 2.
U.S. Appl. No. 08/761,769, Office Action dated Sep. 25, 2001.
U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.
U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 09/686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.
U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
U.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office Action dated Feb. 22, 2012.
Nieto et al., Complex Structure of the nuclear translocation signal of influenza virus polymerase PA subunit. Journal of General Virology, 1994, pp. 29-36, vol. 75.
U.S. Appl. No. 12/681,711, Office Action dated Jan. 31, 2012.
U.S. Appl. No. 12/789,869, Office Action dated Mar. 22, 2011.
U.S. Appl. No. 12/789,869, Office Action dated Dec. 7, 2011.
Bang et al., OmpR regulates the stationary-phase acid tolerance response of *Salmonella enterica* serovar Typhimurium. J. Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.

(56) References Cited

OTHER PUBLICATIONS

Bartlett, Planning for avian influenza. Ann. Intern. Med., 2006, pp. 141-144, vol. 145.

Bearson et al., A low-pH-inducible, PhoPQ-dependent acid tolerance response protects *Salmonella typhimurium* against inorganic acid stress. J. Bacteriol, 1998, pp. 2409-2417, vol. 180.

Bertani, Studies on lysonucleic acid sequencesis. I. The mode of phage liberation by lysogenic *Escherichia coli*. J. Bacteriol, 1951, pp. 293-300, vol. 62, No. 3.

Black et al., Aspartic—semialdehydedehydrogenase and aspartic—semialdehyde, J. Biol. Chem., 1955, pp. 39-50, vol. 213.

Briles et al., Immunization of humans with recombinant pneumococcal surface protein A (rPspA) elicits antibodies that passively protect mice from fatal infection with *Streptococcus pneumoniae* bearing heterologous PspA. J. Infect. Dis., 2000, pp. 1694-1701, vol. 182.

Brooks-Walter et al., The pspC gene of *Streptococcus pneumoniae* encodes a polymorphic protein, PspC, which elicits cross-reactive antibodies to PspA and provides immunity to pneumococcal bacteremia. Infect. Immun. 1999, pp. 6533-6542, vol. 67.

Brosius et al., Spacing of the -10 and -35 regions in the tac promoter. Effect on its in vivo activity. J Biol Chem, 1985, pp. 3539-3540, vol. 260, No. 6.

Brown et al., MurA (MurZ), the enzyme that catalyzes the first committed step in peptidoglycan biosynthesis, is essential in *Escherichia coli*. J. Bacteriol., 1995, pp. 4194-4197, vol. 177.

Buchanan et al., IL-12 Enhances Antibody Responses to T-Independent Polysaccharide Vaccines in the Absence of T and NK Cells. J. Immunol., 1998, pp. 5525-5533, vol. 161.

Buchmeier, et al., DNA repair is more important than catalase for *Salmonella* virulence in mice. J. Clin. Invest., 1995, pp. 1047-1053, vol. 95.

Bumann, Regulated antigen expression in live recombinant *Salmonella enterica* serovar Typhimurium strongly affects colonization capabilities and specific CD4(+)-T-cell responses. Infect. Immun, 2001. pp. 7493-7500, vol. 69, No. 12.

CDC, Update: influenza activity—United States, Sep. 30, 2007-Apr. 5, 2008, and composition of the 2008-09 influenza vaccine. MMWR Morb. Mortal. Wkly Rep., 2008, pp. 404-409, vol. 57.

Chen et al., Genetic mapping of the cold-adapted phenotype of B/Ann Arbor/1/66, the master donor virus for live attenuated influenza vaccines (FluMist). Virology, 2006, pp. 416-423, vol. 345.

U.S. Appl. No. 13/006,072, Office Action dated Apr. 19, 2012.

Sun et al., Highly efficient method for introducing successive multiple scarless gene deletions and markerless gene insertions into the Yersinia pestis chromosome. Appl Environ Microbiol, 2008, pp. 4241-4245, vol. 74.

Curtiss et al., New technologies in using recombinant attenuated *Salmonella* vaccine vectors. Crit. Rev. Immunol., 2010, pp. 255-270, vol. 30.

Curtiss et al., *Salmonella* strains with regulated delayed attenuation in vivo. Infect. Immun., 2009, pp. 1071-1082, vol. 77.

Curtiss et al., *Salmonella typhimurium* deletion mutants lacking adenylate cyclase and cyclic AMP receptor protein are avirulent and immunogenic. Infect Immun, 1987, pp. 3035-3043, vol. 55.

Waltman et al., Biochemical Characteristics of Edwardsiella ictaluri. Applied and Enviornmental Microbiology, 1986, pp. 101-104, vol. 51, No. 1.

Curtiss, Bacterial infectious disease control by vaccine development. J. Clin. Investig., 2002, pp. 1061-1066, vol. 110.

Curtiss, Chromosomal aberrations associated with mutations to bacteriophage resistance in *Escherichia coli*. J. Bacteriol., 1965, pp. 28-40, vol. 89.

Daigle et al., Identification of *Salmonella typhi* genes expressed within macrophages by selective capture of transcribed sequences (SCOTS). Mol Microbiol, 2001, pp. 1211-1222, vol. 41.

U.S. Appl. No. 13/700,591, Office Action dated Apr. 2, 2014.

Dean, 1997. Import of plasmid DNA into the nucleus is sequence specific. Exp. Cell Res., 1997, pp. 293-302, vol. 230.

Reed et al., The W-Beijing Lineage of *Mycobacterium tuberculosis* Overproduces Triglycerides and Has the DosR Dormancy Regulon Constitutively Upregulated. Journal of Bacteriology, 2007, pp. 2583-2589, vol. 189, No. 7.

Dunstan et al., Comparison of the Abilities of Different Attenuated *Salmonella Typhimurium* Strains to Elicit Humoral Immune Responses against a Heterologous Antigen. Infect. Immun., 1998, pp. 732-740, vol. 66.

Dusek et al., Brown, Systemic and mucosal immune responses in mice orally immunized with avirulent *Salmonella typhimurium* expressing a cloned Porphyromonas gingivalis hemagglutinin. Infect Immun, 1994, pp. 1652-1657, vol. 62, No. 5.

Pickard et al., Characterization of defined ompR mutants of *Salmonella typhi*: ompR is involved in the regulation of Vi polysaccharide expression. Infect Immun, 1994, pp. 3984-3993, vol. 62, No. 9.

Egorov et al., Transfectant influenza A viruses with long deletions in the NS1 protein grow efficiently in Vero cells. J. Virol., 1998, pp. 6437-6441, vol. 72.

Enami et al., Introduction of site-specific mutations into the genome of influenza virus. Proc. Natl. Acad. Sci. USA, 1990, pp. 3802-3805, vol. 87.

Fodor et al., Rescue of influenza A virus from recombinant DNA. J. Virol., 1999, pp. 9679-9682, vol. 73.

Formal et al., Construction of a potential bivalent vaccine strain: introduction of Shigella sonnei form I antigen genes into the galE *Salmonella typhi* Ty21a typhoid vaccine strain. Infect. Immun., 1981, pp. 746-750, vol. 34.

Fraser et al., The amino acid composition of T3 bacteriophage. J Biol Chem, 1953, pp. 291-295, vol. 205, No. 1.

Galan et al., Cloning and molecular characterization of genes whose products allow *Salmonella typhimurium* to penetrate tissue culture cells. Proc Natl Acad Sci U S A, 1989, pp. 6383-6387, vol. 86.

Galen et al., Optimization of Plasmid Maintenance in the Attenuated Live Vector Vaccine Strain *Salmonella typhi* CVD 908-htrA. Infect. Immun., 1999, pp. 6424-6433, vol. 67.

Garmory et al., Antibiotic-free plasmid stabilization by operator-repressor titration for vaccine delivery by using live *Salmonella enterica* serovar Typhimurium. Infect. Immun., 2005, pp. 2005-2011, vol. 73.

Gay et al., Positive selection procedure for entrapment of insertion sequence elements in gram-negative bacteria. J Bacteriol, 1985, pp. 918-921, vol. 164, No. 2.

Gentschev et al., Delivery of the p67 sporozoite antigen of Theileria parva by using recombinant *Salmonella dublin*: secretion of the product enhances specific antibody responses in cattle. Infect. Immun., 1998, pp. 2060-2064, vol. 66.

Gerdil, The annual production cycle for influenza vaccine. Vaccine, 2003, pp. 1776-1779, vol. 21.

Ghany et al. Candidate live, attenuated *Salmonella enterica* serotype Typhimurium vaccines with reduced fecal shedding are immunogenic and effective oral vaccines. Infect. Immun., 2007, pp. 1835-1842, vol. 75.

Greenwood, The epidemiology of pneumococcal infection in children in the developing world. Philos. Trans. R. Soc. Lond. B. Biol. Sci., 1999, pp. 777-785, vol. 354.

Gulig et al., Plasmid-associated virulence of *Salmonella typhimurium*. Infect Immun, 1987, pp. 2891-2901, vol. 55.

Lefman J. et al, Three-Dimensional Electron Microscopic Imaging of Membrane Invaginations in *Excherichia coli* Overproducing the Chemotaxis Receptor Tsr. Journal of Bacteriology. Aug. 2004, vol. 186 (15), pp. 5052-5061: abstract; p. 5054.

Hall et al., The role of fur in the acid tolerance response of *Salmonella typhimurium* is physiologically and genetically separable from its role in iron acquisition. J Bacteriol, 1996, pp. 5683-5691, vol. 178.

Hess et al., Superior efficacy of secreted over somatic antigen display in recombinant *Salmonella* vaccine induced protection against listeriosis. Proc. Natl. Acad. Sci. USA, 1996, pp. 1458-1463, vol. 93.

Hicks et al., Incidence of pneumococcal disease due to non-pneumococcal conjugate vaccine (PCV7) serotypes in the United

(56) References Cited

OTHER PUBLICATIONS

States during the era of widespread PCV7 vaccination, 1998-2004. J Infect Dis, 2007, pp. 1346-1354, vol. 196.

Hitchcock et al., Morphological heteronucleic acid sequenceity among *Salmonella* lipopolysaccharide chemotypes in silver-stained polyacrylamide gels. J Bacteriol, 1983, pp. 269-277, vol. 154, No. 1.

Hoffmann et al., "Ambisense" approach for the generation of influenza A virus: vRNA and mRNA synthesis from one template. Virology, 2000, pp. 310-317, vol. 267.

Hohmann et al., Macrophage-inducible expression of a model antigen in *Salmonella typhimurium* enhances immunogenicity. Proc Natl Acad Sci U S A, 1995, pp. 2904-2908, vol. 92, No. 7.

Hollingshead et al., Diversity of PspA: mosaic genes and evidence for past recombination in *Streptococcus pneumoniae*. Infect. Immun., 2000, pp. 5889-5900, vol. 68.

Hopkins et al., A recombinant *Salmonella typhimurium* vaccine induces local immunity by four different routes of immunization. Infect Immun, 1995, pp. 3279-3286, vol. 63.

Jin et al., Multiple amino acid residues confer temperature sensitivity to human influenza virus vaccine strains (FluMist) derived from cold-adapted A/Ann Arbor/6/60. Virology, 2003, pp. 18-24, vol. 306.

Kang et al., Immune responses dependent on antigen location in recombinant attenuated *Salmonella typhimurium* vaccines following oral immunization. FEMS Immunol. Med. Microbiol. Lett., 2003, pp. 99-104, vol. 37.

Kang et al., Immune responses to recombinant pneumococcal PspA antigen delivered by live attenuated *Salmonella enterica* serovar typhimurium vaccine. Infect. Immun., 2002, pp. 1739-1749, vol. 70.

Kang et al., Transduction-mediated transfer of unmarked deletion and point mutations through use of counterselectable suicide vectors. J Bacteriol, 2002, pp. 307-312, vol. 184.

Katzman et al., Invertebrate connective tissue. Isolation of D-arabinose from sponge acidic polysaccharide. Biochem J, 1970, pp. 17-19, vol. 119, No. 1.

Hurme et al, A Proteinaceous Gene Regulator Thermameter in *Salmonella*. Cell, 1997, pp. 55-64, vol. 90.

Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.

Klumpp et al., Roles of the influenza virus polymerase and nucleoprotein in forming a functional RNP structure. EMBO J., 1997, pp. 1248-1257, vol. 16.

Kong et al, Regulated programmed lysis of recombinant *Salmonella* in host tissues to release protective antigens and confer biological containment. PNAS, 2008, pp. 9361-9366, vol. 105, No. 27.

Konjufca et al., A Recombinant Attenuated *Salmonella enterica* Serovar Typhimurium Vaccine Encoding Eimeria acervulina Antigen Offers Protection against E. acervulina Challenge. Infect. Immun., 2006, pp. 6785-6796, vol. 74.

Kotton et al., Enteric pathogens as vaccine vectors for foreign antigen delivery. Infect. Immun., 2004, pp. 5535-5547, vol. 72.

Lee et al., Characterization of recent H5 subtype avian influenza viruses from US poultry. Avian Pathol., 2004, pp. 288-297, vol. 33.

Lee et al., Mechanism of araC autoregulation and the domains of two overlapping promoters, PC and PBAD, in the L-arabinose regulatory region of *Escherichia coli*. Proc. Natl. Acad. Sci. USA, 1981, pp. 752-756, vol. 78.

Li et al. A sopB Deletion Mutation Enhances the Immunogenicity and Protective Efficacy of a Heterologous Antigen Delivered by Live Attenuated *Salmonella enterica* Vaccines. Infection and Immunity, 2008, pp. 5238-5246, vol. 76, No. 11.

Lee et al., Trigger factor retards protein export in *Escherichia coli*. J. Biol Chem, 2002, pp. 43527-43535, vol. 277.

Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.

Loessner et al., Differential effect of auxotrophies on the release of macromolecules by *Salmonella enterica* vaccine strains. FEMS Microbiol. Lett., 2006, pp. 81-88, vol. 265.

Loewen et al., Genetic mapping of katF, a locus that with katE affects the synthesis of a second catalase species in *Escherichia coli*. J Bacteriol, 1984, pp. 668-675, vol. 160.

Luytjes et al., Amplification, expression, and packaging of foreign gene by influenza virus. Cell, 1989, pp. 1107-1113, vol. 59.

Malley et al., CD4+T cells mediate antibody-independent acquired immunity to pneumococcal colonization. PNAS, 2005, pp. 4848-4853, vol. 102.

Massin et al., Cloning of the chicken RNA polymerase I promoter and use for reverse genetics of influenza A viruses in avian cells. J. Virol. 2005, pp. 13811-13816, vol. 79.

Matthay et al., Evaluation of the opsonic requirements for phagocytosis of *Streptococcus pneumoniae* serotypes VII, XIV, and XIX by chemiluminescence assay. Infect Immun, 1981, pp. 228-235, vol. 31.

McClelland et al. Complete genome sequence of *Salmonella enterica* serovar Typhimurium LT2. Nature, 2001, pp. 852-856, vol. 413, No. 6858.

McDaniel et al., Monoclonal antibodies against protease sensitive pnuemococcal anitigens can protect mice form fatal infection with *Streptococcus pneumoniae*. J. Exp. Med., 1984, pp. 368-397, vol. 160.

McDaniel et al., Use of insertional inactivation to facilitate studies of biological properties of pneumococcal surface protein A (PspA). J. Exp. Med. 1987, pp. 381-394, vol. 165.

Miller et al., A novel suicide vector and its use in construction of insertion mutations: osmoregulation of outer membrane proteins and virulence determinants in Virbrio cholerae requires toxR. J. Bacteriol, 1988, pp. 2575-2583, vol. 170.

Miller et al, Bacteriophage T4 genome. Microbiol. Mol. Biol. Rev, 2003, pp. 86-156, vol. 67, No. 1.

Molinari et al., The annual impact of seasonal influenza in the US; measuring disease burden and costs. Vaccine, 2007, pp. 5086-5096, vol. 25.

Mulvey et al., Regulation of transcription of katE and katF in *Escherichia coli*. J Bacteriol, 1990, pp. 6713-6720, vol. 172.

Murti et al., Localization of RNA polymerases on influenza viral ribonucleoproteins by immunogold labeling. Virology, 1988, pp. 562-566, vol. 164.

Nardelli-Haefliger et al., Human papillomavirus type 16 virus-like particles expresses in attenuated *Salmonella typhimurium* elicit mucosal and systemic neutralizing antibodies in mice. Infect. Immun., 1997, pp. 3328-3336, vol. 65.

Nayak et al., A live recombinant avirulent oral *Salmonella* vaccine expressing pneumococcal surface protein A induces protective responses against *Streptococcus pneumoniae*. Infect. Immun. 1998, pp. 3744-3751, vol. 66.

Neumann et al., An improved reverse genetics system for influenza A virus generation and its implications for vaccine production. Proc. Natl. Acad. Sci. USA, 2005, pp. 16825-16829, vol. 102.

Neumann et al., Generation of influenza A viruses entirely from cloned cDNAs Proc. Natl. Acad. Sci. USA, 1999, pp. 9345-9350, vol. 96.

Neumann et al., RNA polymerase I-mediated expression of influenza viral RNA molecules. Virology, 1994, pp. 477-479, vol. 202.

Noda et al., Architecture of ribonucleoprotein complexes in influenza A virus particles. Nature, 2006, pp. 490-492, vol. 439.

Oehler et al., The three operators of the lac operon cooperate in repression. EMBO J, 1990, pp. 973-979, vol. 9, No. 4.

Ogunniyi et al., Contributions of Pneumolysin, Pneumococcal Surface Protein A (PspA), and PspC to Pathogenicity of Streptococcus pneumoniae D39 in a Mouse Model. Infect. Immun. 2007, pp. 1843-1851, vol. 75.

Osterholm, Preparing for the next pandemic, N. Engl. J. Med. 2005, pp. 1839-1842, vol. 352.

(56) References Cited

OTHER PUBLICATIONS

Ozaki et al., Generation of high-yielding influenza A viruses in African green monkey kidney (Vero) cells by reverse genetics. J. Virol. 2004, pp. 1851-1857, vol. 78.
Park et al., Engineered viral vaccine constructs with dual specificity: avian influenza and Newcastle disease. Proc. Natl. Acad. Sci. USA, 2006, pp. 8203-8208, vol. 103.
Pascual et al, Expression of Recombinant Enterotoxigenic *Escherichia coli* Colonization Factor Antigen I by *Salmonella Typhimurium* Elicits a Biphasic T Helper Cell Response. Infect. Immun., 1999, pp. 6249-6256, vol. 67.
Pashine et al., Th1 dominance in the immune response to live *Salmonella Typhimurium*requires bacterial invasiveness but not persistence. Int. Immunol., 1999, pp. 481-489, vol. 11.
Peterson et al., RpoS proteolysis is regulated by a mechanism that does not require the SprE (RssB) response regulator phosphorylation site. J Bacteriol, 2004, pp. 7403-7410, vol. 186.
Pizarro-Cerda et al., The bacterial signal molecule, ppGpp, regulates *Salmonella* virulence nucleic acid sequence expression. Mol Microbiol, 2004, pp. 1827-1844, vol. 52, No. 6.
Prouty et al., *Salmonella enterica* serovar Typhimurium invasion is repressed in the presence of bile. Infect Immun, 2000, pp. 6763-6769, vol. 68.
Quinlivan et al., Attenuation of equine influenza viruses through truncations of the NS1 protein. J. Virol., 2005, pp. 8431-8439, vol. 79.
Rand, Crystal violet can be used to visualize DNA bands during gel electrophoresis and to improve cloning efficiency. Tech Tips Online, 1996 http://www.science-direct.com/science/journal/13662120.
Roberts et al., Oral vaccination against tetanus: comparison of the immunogenicities of *Salmonella* strains expressing fragment C fromt he nirB and htrA promoters. Infect. Immun. 1998, pp. 3080-3087, vol. 66.
Romeo et al, Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.
Sadler et al., A perfectly symmetric lac operator binds the lac repressor very tightly. Proc Natl Acad Sci USA 1983, pp. 6785-6789, vol. 80, No. 22.
Saeland et al., Serum samples from infants vaccinated with a pneumococcal conjugate vaccine, PncT, protect mice against invasive infection caused by *Streptococcus pneumoniae* serotypes 6A and 6B. J Infect Dis, 2001, pp. 253-260, vol. 183.
Hori et al, Construction of self disruptive Bacillus megaterium in response to substrate exhaustion for polyhydroxybutryrate production. Appl Microbiol Biotechnol, 2002, pp. 211-216, vol. 59.
Houng et al., Expression of Vi antigen in *Escherichia coli* K-12: characterization of ViaB form Citrobacter freundii and identity of ViaA with RcsB J. Bacterio, 1992, pp. 5910-5915, vol. 174, No. 18.
Schuchat et al, Bacterial meningitis in the United States in 1995. Active Surveillance Team. N. Engl. J. Med., 1997, pp. 970-976, vol. 337.
Schulman et al., Independent variation in nature of hemagglutinin and neuraminidase antigens of influenza virus: distinctiveness of hemagglutinin antigen of Hong Kong—68 virus. Proc. Natl. Acad. Sci. USA, 1969, pp. 326-333, vol. 63.
Simonsen et al., The impact of influenza epidemics of hospitalizations. J. Infect. Dis., 2000, pp. 831-837, vol. 181.
Rytkonen et al., Ssel, a *Salmonella deubiquitinase* required for macrophase killing and virulence. PNAS, 2007, vol. 104 (pp. 3502-3507).
Ribeiro et al., the role of Polyadenylation Signal Secondary Structures on the Resistance of Plasmid Vectors to Nucleases. J. Gene Med., vol. 6, 2004 (pp. 565-573).
Wang et al., Hemagglutinin (HA) Proteins from H1 and H3 Serotypes of Influenza A Viruses Require Different Antigen Designs for the Induction of Optimal Protective Antibody Responses as Studied by Codon—Optimized HA DNA Vaccines. Journal of Virology, 2006. vol. 80 (pp. 11628-11637).
PCT/US/2008/063303 (WO2008/141226)—International Search Report and Written Opinion of the International Searching Authority, Nov. 26, 2008.
U.S. Appl. No. 12/759,842, Office Action dated Oct. 4, 2011.
PCT/US2008/078991 (WO2009/046449)—International Search Report and Written Opinion of the International Searching Authority, Dec. 15, 2008.
PCT/US2008/078993 (WO2009/046451)—International Search Report and Written Opinion of the International Searching Authority, Dec. 15, 2008.
PCT/US2010/035630 (WO2010/135563)—International Search Report and Written Opinion of the International Searching Authority, Sep. 29, 2010.
PCT/US2009/061100 (WO2010/045620)—International Search Report and Written Opinion of the International Searching Authority, Dec. 4, 2009.
PCT/US2010/020137 (WO 2010/078584)—International Search Report and Written Opinion of the International Searching Authority, Mar. 9, 2010.
PCT/US2011/022110 (WO2011/091291)—International Search Report and Written Opinion of the International Searching Authority, Apr. 11, 2011.
PCT/US2011/038588 (WO2011/150421)—International Search Report and Written Opinion of the International Searching Authority, Nov. 22, 2011.
PCT/US98/24295—International Preliminary Examination Report, Dec. 26, 2000 (WO/1999/025387).
PCT/US2001/0139156—International Preliminary Examination Report, Aug. 16, 2002 (WO/2001/083785).
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.
European Patent Application No. 90905859.6 (EP0465560), Intention to Grant dated Jan. 4, 1995.
European Patent Application No. 90905859.0 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant Sep. 7, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.
European Patent Application No. 01979646.5 (EP1326960), Intention to Grant dated Apr. 8, 2004.
European Patent Application No. 01979646.5 (EP1326960), Decision to Grant dated Oct. 28, 2004.

(56) References Cited

OTHER PUBLICATIONS

European Patent Application No. 03721711.4 (EP1499191), Search Report dated May 23, 2006.
European Patent Application No. 03721711.4 (EP1499191), Office Action dated Aug. 24, 2006.
European Patent Application No. 03721711.4 (EP1499191), Office Action dated Jan. 17, 2007.
European Patent Application No. 03721711.4 (EP1499191), Office Action dated Mar. 23, 2009.
European Patent Application No. 03721711.4 (EP1499191), Office Action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.

\* cited by examiner

**Ty2 *adi* locus**

χ11500: Δ(*adiA-adiC*)

χ11552: ΔP$_{adiA}$::TT *araC* P$_{BAD}$ *adiA*

χ11564: ΔP$_{adiA}$::TT *rhaSR* P$_{rhaBAD}$ *adiA*

χ11568: ΔP$_{adiA}$::TT *rhaSR* P$_{rhaBAD}$ *adiA* Δ(P$_{adiY}$-*adiY*-P$_{adiC}$) *adiC*

χ11636: Δ(P$_{adiY}$-*adiY*-P$_{adiC}$) *adiC*

A

B

χ11552 grown with arabinose (%)

χ11564 grown with rhamnose (%)

C

χ11552 grown with arabinose (%)

χ11564 grown with rhamnose (%)

Grown to OD$_{600}$ of ~0.4 in LB with glucose

χ11260: wt
χ11797: Δ*fur*
χ11798: Δ*pmi* Δ*fur*
χ12040: Δ*fur* Δ*cysG::gadBC*
χ12041: Δ*pmi* Δ*fur* Δ*cysG::gadBC*

SEQUENCE LISTING

```
<160> NUMBER OF SEQ ID NOS: 42

<210> SEQ ID NO 1
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 1
ccggtaccga tgggaatatt ccagcg                                        26

<210> SEQ ID NO 2
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 2
ccggatccct tttacccggt tgtg                                          24

<210> SEQ ID NO 3
<211> LENGTH: 31
<212> TYPE: DNA
<213> ORGANISM: Artificial Sequence
<220> FEATURE:
<223> OTHER INFORMATION: SYNTHESIZED

<400> SEQUENCE: 3
ccggatcccc acgtgtagtt aatgttatcg c                                  31

<210> SEQ ID NO 4
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 4
ccaagcttgg caatcacggc tgcc                                          24

<210> SEQ ID NO 5
<211> LENGTH: 25
```

```
<212> TYPE: DNA
<213> ORGANISM: Artificial Sequence
<220> FEATURE:
<223> OTHER INFORMATION: SYNTHESIZED

<400> SEQUENCE: 5
catggcatgc cgaatgagca aattc                                          25

<210> SEQ ID NO 6
<211> LENGTH: 29
<212> TYPE: DNA
<213> ORGANISM: Artificial Sequence
<220> FEATURE:
<223> OTHER INFORMATION: SYNTHESIZED

<400> SEQUENCE: 6
ccggagatct tgatagtggt atccggctt                                      29

<210> SEQ ID NO 7
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 7
catgggtacc aggaggtaaa agatgatgaa ag                                  32

<210> SEQ ID NO 8
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 8
catggagctc cgccataata atcgtg                                         26

<210> SEQ ID NO 9
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 9
catagccgta ccatgcttcg tcg                                            23

<210> SEQ ID NO 10
<211> LENGTH: 28
<212> TYPE: DNA
<213> ORGANISM: Artificial Sequence
<220> FEATURE:
<223> OTHER INFORMATION: SYNTHESIZED

<400> SEQUENCE: 10
gcgctctaga cgcaccaccg acttccag                                       28

<210> SEQ ID NO 11
<211> LENGTH: 37
<212> TYPE: DNA
<213> ORGANISM: Artificial Sequence
<220> FEATURE:
<223> OTHER INFORMATION: SYNTHESIZED

<400> SEQUENCE: 11
```

-continued gtatcatacc ccctcagaat gttgcagcaa tactcag                                    37

<210> SEQ ID NO 12
<211> LENGTH: 37
<212> TYPE: DNA
<213> ORGANISM: Artificial Sequence
<220> FEATURE:
<223> OTHER INFORMATION: SYNTHESIZED

<400> SEQUENCE: 12
ttccctgagt attgctgcaa cattctgagg gggtatg                                    37

<210> SEQ ID NO 13
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 13
gcatggatcc ccagaaccag ccgaag                                                26

<210> SEQ ID NO 14
<211> LENGTH: 28
<212> TYPE: DNA
<213> ORGANISM: Artificial Sequence
<220> FEATURE:
<223> OTHER INFORMATION: SYNTHESIZED

<400> SEQUENCE: 14
ccggtacccg aactccgtta ttccttac                                              28

<210> SEQ ID NO 15
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 15
ccaagcttca gatagccgac gcc                                                   23

<210> SEQ ID NO 16
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 16
gattagcgga tcctacctga cgc                                                   23

<210> SEQ ID NO 17
<211> LENGTH: 29
<212> TYPE: DNA
<213> ORGANISM: Artificial Sequence
<220> FEATURE:
<223> OTHER INFORMATION: SYNTHESIZED

<400> SEQUENCE: 17
cccgggtgct ggctgaacag ttcctcgag                                             29

<210> SEQ ID NO 18
<211> LENGTH: 29
<212> TYPE: DNA
<213> ORGANISM: Artificial Sequence

<220> FEATURE:
<223> OTHER INFORMATION: SYNTHESIZED

<400> SEQUENCE: 18
ccggatcctc cggcattatg caggcgtcg                                        29

<210> SEQ ID NO 19
<211> LENGTH: 36
<212> TYPE: DNA
<213> ORGANISM: Artificial Sequence
<220> FEATURE:
<223> OTHER INFORMATION: SYNTHESIZED

<400> SEQUENCE: 19
ccggatccgc gtgtcctgtc agttttttttt cttctc                              36

<210> SEQ ID NO 20
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 20
tctagatctc cgcatgggta catgaagttc cgg                                  33

<210> SEQ ID NO 21
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 21
acatgcatgc tgtgactggg atgacttctt cccg                                 34

<210> SEQ ID NO 22
<211> LENGTH: 31
<212> TYPE: DNA
<213> ORGANISM: Artificial Sequence
<220> FEATURE:
<223> OTHER INFORMATION: SYNTHESIZED

<400> SEQUENCE: 22
tcccccgggc acttttccgc aatcaaggca g                                    31

<210> SEQ ID NO 23
<211> LENGTH: 29
<212> TYPE: DNA
<213> ORGANISM: Artificial Sequence
<220> FEATURE:
<223> OTHER INFORMATION: SYNTHESIZED

<400> SEQUENCE: 23
gcactctaga ttaatctttc tgcgaattg                                       29

<210> SEQ ID NO 24
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 24
gcatctcgag gctgaatttc attac                                           25

```
<210> SEQ ID NO 25
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 25
tcagtaacga gaaggtcgcg                                              20

<210> SEQ ID NO 26
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 26
gctgaaatat gactccactc ac                                           22

<210> SEQ ID NO 27
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 27
cgtcaacacc aacttcgtc                                               19

<210> SEQ ID NO 28
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 28
accgacttcc agattatgtt cc                                           22

<210> SEQ ID NO 29
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 29
cgtgttgatc agcgttccc                                               19

<210> SEQ ID NO 30
<211> LENGTH: 27
<212> TYPE: DNA
<213> ORGANISM: Artificial Sequence
<220> FEATURE:
<223> OTHER INFORMATION: SYNTHESIZED

<400> SEQUENCE: 30
ggccgagctc ctatcctgcc gcaaacc                                      27

<210> SEQ ID NO 31
<211> LENGTH: 52
<212> TYPE: DNA
<213> ORGANISM: Artificial Sequence
<220> FEATURE:
<223> OTHER INFORMATION: SYNTHESIZED
```

<400> SEQUENCE: 31
caattctagg atagaataat aaagcggccg cgacattacc ccttaatggt tg            52

<210> SEQ ID NO 32
<211> LENGTH: 45
<212> TYPE: DNA
<213> ORGANISM: Artificial Sequence
<220> FEATURE:
<223> OTHER INFORMATION: SYNTHESIZED

<400> SEQUENCE: 32
gtttttttgg gctagcctcg agaggagttt aaaatggata agaag                   45

<210> SEQ ID NO 33
<211> LENGTH: 45
<212> TYPE: DNA
<213> ORGANISM: Artificial Sequence
<220> FEATURE:
<223> OTHER INFORMATION: SYNTHESIZED

<400> SEQUENCE: 33
gaataacagg gctttatttt aagatctaaa aagggagcga tgaat                   45

<210> SEQ ID NO 34
<211> LENGTH: 42
<212> TYPE: DNA
<213> ORGANISM: Artificial Sequence
<220> FEATURE:
<223> OTHER INFORMATION: SYNTHESIZED

<400> SEQUENCE: 34
catcgctccc tttttagatc tgccctgtta ttcagggctt ta                      42

<210> SEQ ID NO 35
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 35
gcatggtacc cgaccaatgc ggcaac                                        26

<210> SEQ ID NO 36
<211> LENGTH: 29
<212> TYPE: DNA
<213> ORGANISM: Artificial Sequence
<220> FEATURE:
<223> OTHER INFORMATION: SYNTHESIZED

<400> SEQUENCE: 36 cccccctcgag ggtatgttta aagctgttc                                    29

<210> SEQ ID NO 37
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 37
ggcaccgttc gtcgccccgg atatcg                                        26

<210> SEQ ID NO 38

```
<211> LENGTH: 27
<212> TYPE: DNA
<213> ORGANISM: Artificial Sequence
<220> FEATURE:
<223> OTHER INFORMATION: SYNTHESIZED

<400> SEQUENCE: 38
caggtaaagc taagcagctc acattac                                          27

<210> SEQ ID NO 39
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 39
cgttctgatg tcccatgtgg caccgg                                           26

<210> SEQ ID NO 40
<211> LENGTH: 50
<212> TYPE: DNA
<213> ORGANISM: Artificial Sequence
<220> FEATURE:
<223> OTHER INFORMATION: SYNTHESIZED

<400> SEQUENCE: 40
cattaagggg taatgtcgcg gccgctttat tattctatcc tagaattgtg                 50

<210> SEQ ID NO 41
<211> LENGTH: 46
<212> TYPE: DNA
<213> ORGANISM: Artificial Sequence
<220> FEATURE:
<223> OTHER INFORMATION: SYNTHESIZED

<400> SEQUENCE: 41
cttcttatcc attttaaact cctctcgagg ctagcccaaa aaaacg                     46

<210> SEQ ID NO 42
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 42
gattagcgga tcctacctga cgc                                              23
```

ATTENUATED LIVE BACTERIA WITH INCREASED ACID RESISTANCE AND METHODS OF USE THEREOF

CROSS REFERENCE TO RELATED APPLICATIONS

This application claims the priority of U.S. provisional application No. 61/836,140, filed Jun. 17, 2013, which is hereby incorporated by reference in its entirety.

GOVERNMENTAL RIGHTS

This invention was made with government support under 1R21AI092307 awarded by the National Institutes of Health. The government has certain rights in the invention.

FIELD OF THE INVENTION

The present invention relates to inducing acid resistance in a bacterium and methods of increasing the acid resistance of an acid sensitive bacterium.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

In order to reach their intestinal habitat, enteric microbes must first survive the formidable low pH environment of the stomach, making an acid-coping strategy imperative. Wild-type Salmonella enterica serotypes have multiple ways to resist low pH. First, the acid tolerance response (ATR) upregulates acid shock proteins to temporarily prevent cellular damage. Second, the acid resistance systems (AR) consume protons to raise the intracellular pH. AR1 system is regulated by Crp and is poorly understood. The remaining systems, AR3, AR4 and AR5 (AR2 is not present in Salmonella) rely on arginine, lysine and ornithine decarboxylases, respectively. However, AR3-5 are typically repressed under standard laboratory growth conditions, and the ATR in many live attenuated Salmonella vaccines is impaired, making gastric transit challenging for these strains. In addition, many means used to attenuate Salmonella for virulence have a secondary effect of increasing sensitivity to acid, thereby increasing the effective dose required for immunogenicity. As a result, oral Salmonella vaccines are typically given with an agent designed to increase the gastric pH, such as bicarbonate. While this approach is helpful, it precludes the Salmonella vaccine from sensing important environmental signals (i.e. low pH) that optimize its ability to effectively interact with host tissues. This results in reduced immunogenicity as a vaccine.

SUMMARY OF THE INVENTION

In an aspect, the invention encompasses a recombinant attenuated derivative of a pathogenic enteric bacterium comprising at least one of the following: a regulatable promoter operably linked to a nucleic acid encoding an arginine decarboxylase and a nucleic acid encoding an arginine agmatine antiporter; a regulatable promoter operably linked to a nucleic acid encoding a glutamate decarboxylase and a nucleic acid encoding a glutamate/γ-aminobutyric acid antiporter; or a regulatable promoter operably linked to a nucleic acid encoding a lysine decarboxylase and a nucleic acid encoding a lysine/cadaverine antiporter.

In another aspect, the invention encompasses a method for increasing the acid resistance of an acid sensitive bacterium, the method comprising introducing into the acid sensitive bacterium a cassette comprising at least one of the following: a regulatable promoter operably linked to a nucleic acid encoding an arginine decarboxylase and a nucleic acid encoding an arginine agmatine antiporter; a regulatable promoter operably linked to a nucleic acid encoding a glutamate decarboxylase and a nucleic acid encoding a glutamate/γ-aminobutyric acid antiporter; or a regulatable promoter operably linked to a nucleic acid encoding a lysine decarboxylase and a nucleic acid encoding a lysine/cadaverine antiporter, such that in the absence of induction of the regulatable promoter, the recombinant bacterium is acid sensitive, but upon induction of the regulatable promoter, the recombinant bacterium displays an increase in acid resistance.

A recombinant Salmonella bacterium, the bacterium comprising a regulatable promoter operably linked to at least one nucleic acid selected from the group consisting of adiA and adiC; gadB and gadC; and cadB and cadA.

BRIEF DESCRIPTION OF THE FIGURES

The application file contains at least one drawing executed in color. Copies of this patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 16. Rescue of acid sensitive *S. Gallinarum* strains by arabinose-inducible gadBC system. Cultures were grown aerobically in LB broth to an optical density at 600 nm of 0.4. Cells were harvested, washed and challenged with E medium at pH 3.0 for one hour. Numbers of surviving cells were determined by direct plating onto LB plates. Data are presented as the mean and SEM for each time point.

FIG. 17. Survival of RASV strains during low pH gastric transit. Histamine-treated mice were inoculated orally with $10^9$ CFU of (A) χ9633 (pYA4088, pWSK129), (B) χ9639 (pYA4088, pWSK129), (C) χ9640 (pYA4088, pWSK129) or (D) χ9558 (pYA4088, pWSK129). Mice received either 1.3% sodium bicarbonate, chocolate Ensure or nothing prior to and immediately following immunization to neutralize gastric acid. The number of viable vaccine cells in the small intestine was quantified one hour after immunization. Data are presented as the number of CFU/g intestine of individual mice, with the geometric mean of the group displayed as a solid horizontal line. Groups that exhibited a significant increase ($p<0.05$) in the number of viable vaccine cells in the small intestine over the control group are marked with an asterisk (*). Data are the combined results of two independent experiments (8 mice total).

DETAILED DESCRIPTION

The present invention encompasses a bacterium with increased acid resistance, methods of increasing the acid resistance of a bacterium, and methods of use thereof. The invention also encompasses vaccine compositions comprised of a bacterium exhibiting an increase in acid resistance. Advantageously, a bacterium with an increase in acid resistance of the invention may be administered orally to a subject and substantially survive the low pH of the subject's stomach, while exposure to the low pH environment stimulates up-regulation of invasion and/or virulence related nucleic acid sequences.

I. Recombinant Attenuated Bacterium

A recombinant bacterium of the invention is typically a bacterial enteric pathogen, and belongs to a species or strain commonly used for a vaccine.

Enteric pathogenic bacteria are agents of intestinal disease typically acquired through ingestion. These pathogens include, but are not limited to, bacteria of the family Enterobacteriaceae, such as *Salmonella* species, *Shigella* species, *Yersinia* species (e.g. *Y. pseudotuberculosis* and *Y. enterocolitica*), certain pathovars of *Escherichia coli*, including enterotoxigenic *E. coli* (ETEC), enterohaemorrhagic *E. coli* (EHEC), enteropathogenic *E. coli* (EPEC) and extraintestinal *E. coli* (ExPEC). Other enteric pathogens include *Vibrio* species (e.g. *V. cholerae*) and the gram-positive bacterium *Listeria monocytogenes*.

To be safe for use as a vaccine, the bacterial enteric pathogen must be attenuated for virulence by deletion or regulated expression of a virulence gene. In the case of *Salmonella*, for instance, the following genes may be altered to achieve attenuation: pab, aroA, aroC, aroD, asdA, dapA, dam, murA, nadA, pncB, galE, pmi, fur, ompR, htrA, hemA, cdt, cya, crp, phoP, phoQ, rfc, rfaH, poxA, galU, guaB, guaA, hfq, msbB or genes required for the function of type 3 secretion systems in pathogenicity island 2, such as ssaV, or an effector molecule secreted by the type 3 secretion system, such as sopB. The genes may be deleted or a regulatable promoter may be inserted in front of the gene to achieve regulated delayed attenuation. As used herein, "regulated delayed attenuation" refers to the ability of the microbe to colonize a host and then display an attenuation phenotype to avoid actually causing a symptomatic infection.

In the case of *Shigella*, these genes may include guaA, guaB, senA, senB, set, aroA, virG, msbB, icsA, iuc, iutA, ipaB, ipaC, ipaD, ipaA. The genes may be deleted or a regulatable promoter may be inserted in front of the gene to achieve regulated delayed attenuation.

In the case of *E. coli*, attenuating mutations may include deletions in ompF, ompC, ompR, aroA, aroC, aroD, astA, eltB, eltA, estA, cya, crp. The genes may be deleted or a regulatable promoter may be inserted in front of the gene to achieve regulated delayed attenuation.

In some embodiments, a recombinant bacterium of the invention is a species or subspecies of the *Salmonella* genera. For instance, the recombinant bacterium may be a *Salmonella enterica* serovar. In an exemplary embodiment, a bacterium of the invention may be derived from *S. Typhimurium, S. Typhi, S. Paratyphi, S. Gallinarum, S. Enteritidis, S. Choleraesius, S. Arizona*, or *S. Dublin*. In another exemplary embodiment, a bacterium of the invention may be an *S. Typhi* bacterium. In yet another exemplary embodiment, a bacterium of the invention may be an *S. Typhi* Ty2 bacterium. In yet still another exemplary embodiment, a bacterium of the invention may be an *S. Gallinarum* bacterium. In still yet another exemplary embodiment, a bacterium of the invention may be an *S. Dublin* bacterium.

A recombinant bacterium of the invention derived from *Salmonella* may be particularly suited for use as a vaccine. Infection of a host with a *Salmonella* strain typically leads to colonization of the gut-associated lymphoid tissue (GALT) or Peyer's patches, which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus the use of recombinant *Salmonella* for oral immunization stimulates all three branches of the immune system, which is particularly important for immunizing against infectious disease agents that colonize on and/or invade through mucosal surfaces.

(a) Regulatable Cassette

A recombinant bacterium of the invention comprises a regulatable cassette. Such a cassette usually comprises a regulatable promoter operably linked to i) an arginine decarboxylase and an arginine agmatine antiporter; ii) a glutamate decarboxylase and a glutamate/γ-aminobutyric acid antiporter; or iii) a lysine decarboxylase and a lysine/cadaverine antiporter. Each of these elements is described in more detail below.

The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function.

Figure 1:
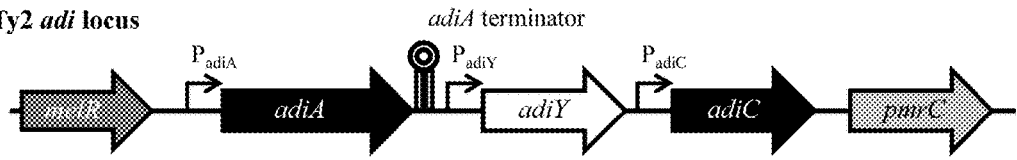
FIG. 1. Schematic diagram of arginine decarboxylase mutations. The genes and associated regulatory sequences for the Δ(adiA-adiC), $\Delta P_{adiA}$::TT araC $P_{araBAD}$ adiA, $\Delta P_{adiA}$::TT rhaSR $P_{rhaBAD}$ adiA, and $\Delta(P_{adiY}$-adiY-$P_{adiC})$ adiC mutations are shown above, along with the archetypal strain number. The wild-type arginine decarboxylase locus (adi) of S. Typhi Ty2 is depicted for comparative purposes. The diagram is approximately to scale. (→) promoter; (⸙) transcription terminator.
Figure 1:
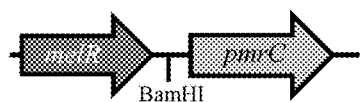
Figure 1:
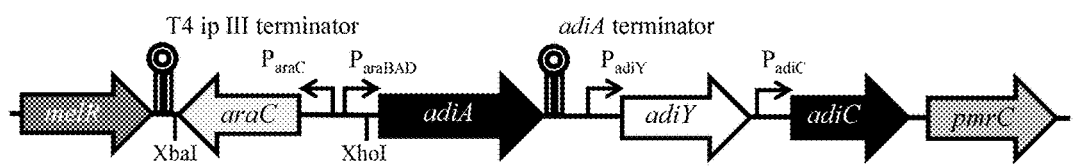
Figure 1:
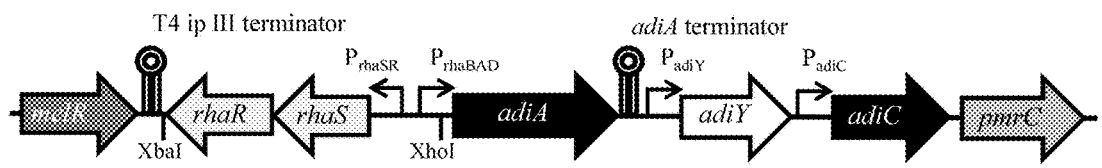
Figure 1:
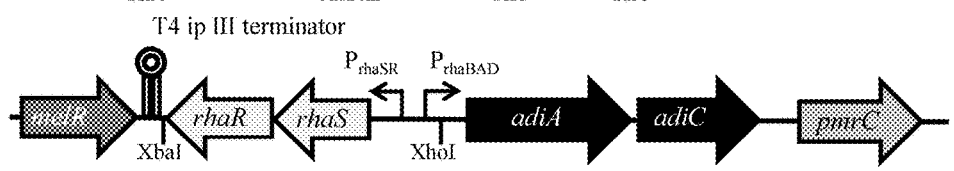
Figure 1:
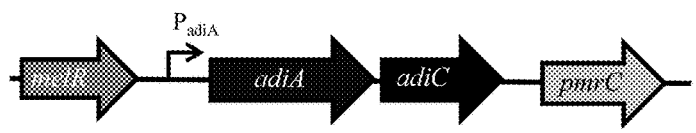

A regulatable cassette of the invention may be present in the chromosome of the recombinant bacterium, or may be present in an extrachromosomal vector. In one embodiment, a regulatable cassette may be present in the chromosome of the recombinant bacterium. Methods of chromosomally integrating a regulatable cassette are known in the art and detailed in the examples. Generally speaking, the regulatable cassette should not be integrated into a locus that disrupts colonization of the host by the recombinant bacterium, or that negatively impacts the use of the bacterium to evoke an immune response, such as in a vaccine. In one embodiment, the regulatable cassette may be chromosomally integrated into the locus that comprises nucleic acid encoding an arginine decarboxylase and/or an arginine agmatine antiporter. In another embodiment, the regulatable cassette may be chromosally integrated into the locus that comprises nucleic acid encoding a glutamate decarboxylase and/or a glutamate/γ-aminobutyric acid antiporter. In yet another embodiment, the regulatable cassette may be chromosomally integrated into the locus that comprises nucleic acid encoding a lysine decarboxylase and/or a lysing/cadaverine antiporter.

In another embodiment, a regulatable cassette of the invention may be present in an extrachromosomal vector. As used herein, "vector" refers to an autonomously replicating nucleic acid unit. The present invention can be practiced with any known type of vector, including viral, cosmid, phasmid, and plasmid vectors. The most preferred type of vector is a plasmid vector.

i) Regulatable Promoter

A regulatable cassette of the invention comprises a regulatable promoter. As used herein, the term "promoter" may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid.

The regulated promoter used herein generally allows transcription of a nucleic acid encoding an arginine decarboxylase and a nucleic acid encoding an arginine agmatine antiporter while in a permissive environment (i.e., in vitro aerobic growth), but ceases transcription while in a non-permissive environment (i.e., during anaerobic growth of the bacterium in an animal or human host). For instance, the promoter may be sensitive to a physical or chemical difference between the permissive and non-permissive environment. Stated another way, a regulated promoter of the invention allows for inducible expression of a nucleic acid encoding an arginine decarboxylase and a nucleic acid encoding an arginine agmatine antiporter, even under aerobic conditions. In another embodiment, the regulated promoter used herein generally allows transcription of a nucleic acid encoding a glutamate decarboxylase and a nucleic acid encoding a glutamate/γ-aminobutyric acid antiporter while in a permissive environment (i.e., in vitro aerobic growth), but ceases transcription while in a non-permissive environment (i.e., during anaerobic growth of the bacterium in an animal or human host). Stated another way, a regulated promoter of the invention allows for inducible expression of a nucleic acid encoding a glutamate decarboxylase and a nucleic acid encoding a glutamate/γ-aminobutyric acid antiporter, even under aerobic conditions. In still another embodiment, the regulated promoter used herein generally allows transcription of a nucleic acid encoding a lysine decarboxylase and a nucleic acid encoding a lysine/cadaverine antiporter while in a permissive environment (i.e., in vitro aerobic growth), but ceases transcription while in a non-permissive environment (i.e., during anaerobic growth of the bacterium in an animal or human host). Stated another way, a regulated promoter of the invention allows for inducible expression of a nucleic acid encoding a lysine decarboxylase and a nucleic acid encoding a lysine/cadaverine antiporter, even under aerobic conditions. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system, which has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$.

Other enteric bacteria contain arabinose regulatory systems homologous to the araC-araBAD system from E. coli. For example, there is homology at the amino acid sequence level between the E. coli and the S. Typhimurium AraC proteins, and less homology at the DNA level. However, there is high specificity in the activity of the AraC proteins. For example, the E. coli AraC protein activates only E. coli $P_{BAD}$ (in the presence of arabinose) and not S. Typhimurium $P_{BAD}$. Thus, an arabinose regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In other embodiments, the promoter may be responsive to the level of maltose in the environment. Generally speaking, maltose may be present during the in vitro growth of a bacterium, while typically absent from host tissue. The malT nucleic acid sequence encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced by the addition of maltose. Unlike the araC-P$_{BAD}$ system, malT is expressed from a promoter (P$_T$) functionally unconnected to the other mal promoters. P$_T$ is not regulated by MalT. The malEFG-malKBM promoter is a bidirectional promoter controlling expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by the malT nucleic acid sequence product, is referred to herein as P$_{KBM}$, and the portion of the malEFG-malKBM promoter that mediates expression of the malEFG nucleic acid sequence, and that is controlled by the malT nucleic acid sequence product, is referred to herein as P$_{EFG}$. Full induction of P$_{KBM}$ requires the presence of the MalT binding sites of P$_{EFG}$. For use in the vectors and systems described herein, a cassette with the malT nucleic acid sequence and one of the mal promoters may be used. This cassette is referred to herein as malT-P$_{mal}$. In the presence of maltose, the MalT protein is a positive regulatory element that allows expression from P$_{mal}$.

In still other embodiments, the promoter may be sensitive to the level of rhamnose in the environment. Analogous to the araC-P$_{BAD}$ system described above, the rhaRS-P$_{rhaB}$ activator-promoter system is tightly regulated by rhamnose. Expression from the rhamnose promoter (P$_{rha}$) is induced to high levels by the addition of rhamnose, which is common in bacteria but rarely found in host tissues. The nucleic acid sequences rhaBAD are organized in one operon that is controlled by the P$_{rhaBAD}$ promoter. This promoter is regulated by two activators, RhaS and RhaR, and the corresponding nucleic acid sequences belong to two transcription units that are located in the opposite direction of the rhaBAD nucleic acid sequences. If L-rhamnose is available, RhaR binds to the P$_{rhaRS}$ promoter and activates the production of RhaR and RhaS. RhaS together with L-rhamnose in turn binds to the P$_{rhaBAD}$ and the P$_{rhaT}$ promoter and activates the transcription of the structural nucleic acid sequences. Full induction of rhaBAD transcription also requires binding of the Crp-cAMP complex, which is a key regulator of catabolite repression.

Generally speaking, the concentration of rhamnose necessary to induce expression is typically less than about 2%. In some embodiments, the concentration is less than about 1.5%, 1%, 0.5%, 0.2%, 0.1%, or 0.05%. In other embodiments, the concentration is about 0.6%, about 0.5%, about 0.4%, about 0.3%, about 0.2%, or about 0.1%. In an exemplary embodiment, the concentration is about 0.1%. In another exemplary embodiment, the concentration is about 0.4%

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC P$_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the P$_{rhaBAD}$ promoter. In some embodiments, the rhaRS-P$_{rhaB}$ activator-promoter cassette from an *E. coli* K-12 strain may be used.

In still other embodiments, the promoter may be sensitive to the level of xylose in the environment. The xylR-P$_{xylA}$ system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-P$_{BAD}$ system described above, the xylR-P$_{xylAB}$ and/or xylR-P$_{xylFGH}$ regulatory systems may be used in the present invention. In these embodiments, xylR P$_{xylAB}$ xylose interacting with the XylR protein activates transcription of nucleic acid sequences operably-linked to either of the two P$_{xyl}$ promoters.

The nucleic acid sequences of the promoters detailed herein are known in the art, and methods of operably-linking them to a nucleic acid sequence encoding an arginine decarboxylase and a nucleic acid encoding an arginine agmatine antiporter are known in the art and detailed in the examples.

ii) A Nucleic Acid Sequence Encoding an Arginine Decarboxylase

A regulatable cassette of the invention further comprises an arginine decarboxylase. An arginine decarboxylase is an enzyme that catalyzes the chemical reaction L-arginine ↔ agmatine and $CO_2$, and is classified as EC 4.1.1.19. Generally speaking, an arginine decarboxylase useful in the present invention will have activity similar to AdiA (e.g. protect a cell from low pH). Suitable examples of arginine decarboxylase are known in the art, and may include the following enzymes (referenced by UNIPROT identifiers, available at www.uniprot.org): Q5L5E7, AAXB_CHLAB; Q822F3, AAXB_CHLCV; Q255I0, AAXB_CHLFF; Q9PK21, AAXB_CHLMU; Q9Z6M7, AAXB_CHLPN; P0C8R4, AAXB_CHLT2; Q3KLY3, AAXB_CHLTA; P0C8R5, AAXB_CHLTB; O84378, AAXB_CHLTR; Q7XRA1, ADC2_ORYSJ; Q96A70, ADC_HUMAN; P28629, ADIA_ECOLI; Q9YG22, ARGDC_AERPE; A8MBV3, ARGDC_CALMQ; A2BM05, ARGDC_HYPBU; A8AAB6, ARGDC_IGNH4; A4YH98, ARGDC_METS5; Q8ZWK3, ARGDC_PYRAE; A4WIW6, ARGDC_PYRAR; A3MTU5, ARGDC_PYRCJ; A1RV83, ARGDC_PYRIL; B1YD10, ARGDC_PYRNV; A3DLU8, ARGDC_STAMF; Q4J932, ARGDC_SULAC; C3N6F7, ARGDC_SULIA; C4 KHX2, ARGDC_SULIK; C3MQN7, ARGDC_SULIL; C3MWN7, ARGDC_SULIM; C3NGS9, ARGDC_SULIN; C3NEW5, ARGDC_SULIY; Q9UWU1, ARGDC_SULSO; Q971K9, ARGDC_SULTO; O27983, PDAD1_ARCFU; Q8TLM4, PDAD1_METAC; P58889, PDAD1_METMA; O30240, PDAD2_ARCFU; Q8TKB4, PDAD2_METAC; P58890, PDAD2_METMA; B3EGI2, PDAD_CHLL2; B3QM53, PDAD_CHLP8; B3ELD9, PDAD_CHLPB; B3QWJ5, PDAD_CHLT3; Q8KEX0, PDAD_CHLTE; B0R6U7, PDAD_HALS3; Q9HNQ0, PDAD_HALSA; A6UUL7, PDAD_META3; Q12UX3, PDAD_METBU; Q57764, PDAD_METJA; Q8TXD4, PDAD_METKA; A4G0Z0, PDAD_METM5; A9A979, PDAD_METM6; A6VHH0, PDAD_METM7; Q6LWX2, PDAD_METMP; O26956, PDAD_METTH; A6UQM7, PDAD_METVS; A9A5S1, PDAD_NITMS; Q3B5D1, PDAD_PELLD; Q6KZS5, PDAD_PICTO; B4S6J7, PDAD_PROA2; A4SFG2, PDAD_PROVI; Q9V173, PDAD_PYRAB; Q8U0G6, PDAD_PYRFU; O59240, PDAD_PYRHO; Q5JFI4, PDAD_PYRKO; Q9HK30, PDAD_THEAC; C6A2R5, PDAD_THESM; Q97AN7, PDAD_THEVO; Q0W1C7, or PDAD_UNCMA.

In some embodiments, an arginine decarboxylase of the invention is from a *Salmonella* species. In particular embodiments, an arginine decarboxylase of the invention is from a *Salmonella Typhi* strain. In still other embodiments, an arginine decarboxylase of the invention is from a *S. Typhi* Ty2 strain. In an exemplary embodiment, an arginine decarboxylase of the invention has the amino acid sequence of the protein at accession number Q8Z1P1.

iii) A Nucleic Acid Encoding an Arginine Agmatine Antiporter

A regulatable cassette of the invention comprises an arginine agmatine antiporter. An arginine agmatine antiporter exchanges extracellular arginine for its intracellular decarboxylation product agmatine (Agm) thereby expelling intracellular protons. Generally speaking, an arginine agmatine antiporter useful in the present invention will have activity similar to AdiC (e.g. protect a cell from low pH). Suitable examples of a arginine agmatine antiporter are known in the art, and may include the following enzymes (referenced by UNIPROT identifiers, available at www.uniprot.org):

| | | | | | |
|---|---|---|---|---|---|
| Q5L5E6 | Q822F2 | Q255I1 | Q9PK20 | Q9Z6M8 | |
| B0B7U3 | Q3KLY0 | B0BC08 | O84379 | P60063 | P60062 |
| P60061 | P60065 | P60066 | P60064 | Q8ZGS9 | F9I2W4 |
| L0ZZ71 | K5SRC8 | L2XUK4 | L0ZZ90 | L3LBG0 | K3L3A1 |
| I7RFE4 | K5JIM6 | H4VPM7 | K3ECI9 | K5JII2 | L4W4Y5 |
| H4VPK5 | F3NW25 | K3B3S5 | I7V0V1 | K3SS41 | K5U1P0 |
| L4F2K6 | L5IZK9 | L4VBA1 | E1IV59 | L8T7H9 | E1IV81 |
| I6FGU1 | L8RFY1 | J1FC03 | I5XD20 | F1ZQN0 | L3RY40 |
| L4T3H6 | L4T549 | B3H9N6 | L0X6N1 | L0X6Q1 | B5NPC3 |
| B5MPV9 | I6JZL9 | I7UDX0 | A9ZUE1 | L1GKB6 | L4YQS8 |
| I2SQ31 | B5PIR2 | L2AD21 | B3YHW3 | F9A052 | G1ZS25 |
| I6I720 | L3ANK2 | I8L5B5 | I7V0M1 | B2P2P0 | I6K2D0 |
| D1TQ94 | B3XCN3 | L4TIY7 | E7UJV3 | G7AK02 | I2ZAI5 |
| I5DC16 | F5MWJ7 | K5U1M6 | L3XAL9 | L5DBB6 | C0AU61 |
| I8AEV7 | I7S457 | J9XI24 | C0AU59 | C0AU62 | F4UGH3 |
| L9HFX9 | I5XWG2 | L3EKM3 | L3VWN3 | L3DTY3 | K3RCT8 |
| L8CSG7 | I5VI26 | K2X636 | L2E4E2 | K3AGX2 | I7UAZ0 |
| L1ZHH6 | L3M033 | D7ZE63 | I5D8I3 | I7X7J6 | I5Q9Q8 |
| I5M3V3 | J1YF14 | D7ZE41 | L2ZZ90 | L2ZV57 | L4FNN9 |
| L1R3X9 | L1R3Z5 | L3YQ74 | D8AX24 | J9XD49 | D8AX02 |
| L3BVT4 | L2Y3Z0 | L3AQT2 | K3L9D5 | I5S6B5 | D2ZGU0 |
| H4W4R4 | L3IJA7 | L4JLJ2 | K2ZXC3 | I8BDE6 | H4W4P4 |
| D6KD06 | L4A9N4 | G5RNX8 | I4JEM2 | K2ZDJ2 | D8AKJ4 |
| L3XEU2 | I8P6H8 | E7K6V9 | L8Z8R4 | L8YKJ3 | D8AKL7 |
| L3NNJ6 | L3BFQ8 | K3MKD0 | H4KAZ1 | H4KAX3 | L4IHB5 |
| L2BF09 | E7V2M9 | G9WDQ0 | F1Y6E3 | K3JZ37 | L2BX70 |
| J9X347 | B3IGV7 | L4CV86 | K5SPP8 | L8BQC1 | L3NN06 |
| K3U0457 | F4T7G8 | E3Y474 | B3AHE0 | L4H192 | E9TP44 |
| I6G8F1 | I6GL91 | I6GBL6 | L8YEL4 | E9TP22 | G7B431 |
| E9U4M4 | I6GBF5 | I6F968 | L0X7G9 | L0X7I9 | K3QB35 |
| I5EN09 | L1GNR1 | L1GNP4 | K5QU54 | L4ZG30 | J1W870 |
| I7XHW6 | G5WM30 | L2WZD7 | L1AB99 | L1AB78 | I7V7C5 |
| G5NFS9 | I8NA30 | G1YHG9 | G5NFT1 | E3XKM9 | L1EFJ6 |
| L4QDY7 | L1EFL8 | K2W2K4 | F4V9D8 | G2CT24 | I7PI89 |
| C8T226 | I5W5W6 | B5P6C4 | H5N2D9 | L4EP61 | I5HRC9 |
| H5N267 | I7UST4 | L1F849 | L1F871 | K5T2Y1 | E7JIF7 |
| F5QPJ9 | H4WZP7 | L3RSY3 | H4WZM8 | I2R8G7 | B5Q4D3 |
| I5MJT7 | L8C1L1 | I2UGJ6 | F3VDW4 | H1FJ08 | G5MRE2 |
| I5MTW8 | G5MRE4 | K3KCA8 | L4XNM3 | K5DXC6 | K5ISM6 |
| K5F1V1 | K5ISH8 | I8AKN2 | I6CMX1 | I7CA768 | G0F4S0 |
| E6B426 | J1C6G7 | L4SYQ4 | K3S724 | I8H5G7 | J5CMZ3 |
| I5M6S7 | J1W394 | L4KR23 | I6BD24 | K3GSB1 | L4UGY3 |
| B2NQU7 | E9TK06 | E9TK28 | I2ZLX4 | F5QBC2 | I5D999 |
| B0GR46 | D8C1N4 | D8BQX0 | L3IMN2 | E5ZS94 | L2X415 |
| B3WYW2 | E5ZSB7 | L8SVA7 | L3MX95 | D7ZVD8 | I7ZAY6 |
| F9ALT1 | I5S787 | K2XVU7 | H1DRT2 | G5U5M4 | I5EVB1 |
| I8SH69 | G9Y8K8 | H1E1A5 | G9Y4C6 | G9Y9L2 | L8SLE6 |
| I3A6R7 | G9Y813 | E7TTL9 | I2T1Y1 | J1GHD8 | G5X1P1 |
| L1BFR5 | L1BFT3 | G5UZS2 | F9C3H2 | G5QBN3 | I5G8K3 |
| L1BCM1 | L1BCJ8 | K2V6L4 | G9SB43 | B0GG51 | L2CSK5 |
| L5D1W2 | J1EY15 | G5VHH0 | G2CCI8 | K3GZI0 | E1HK03 |
| K3PN87 | L4XCP6 | I6DUZ6 | I6EXQ7 | I5QHY5 | E1HJY3 |
| D4E2F3 | G5LHQ4 | L3CJQ8 | L2UQB9 | L3FKD7 | K3TEP7 |

-continued

| | | | | | |
|---|---|---|---|---|---|
| L9EA37 | I6DE79 | F3WRA4 | I2V7B6 | L0YSU5 | K5I296 |
| L0YQH4 | L2AJI5 | F4LZD4 | G2B2X5 | G0DBW7 | L3MTD6 |
| I8IDI1 | I6IKD0 | K3ADY5 | L5AR67 | L4ZY81 | I5Z6K3 |
| B3BTH9 | G5SJZ9 | B0HEW5 | G5QT01 | B2N252 | K3J5D8 |
| I5IS05 | E7JBV5 | L3NM54 | K5HAC9 | L4PPI9 | K5J592 |
| E1JCI2 | L4TRI3 | L5C0A6 | D4F0D4 | D4F4Y3 | D4F2I3 |
| E1JCG1 | I7SA11 | I6KTI0 | J9XCX8 | D4F0F6 | K3HBW8 |
| L4YWU8 | L2UUC4 | I2RRR4 | K5SHK1 | H4USI6 | L3SMZ0 |
| I2TWS7 | I7UER9 | I7RDJ7 | F3W5J5 | G6ZAS1 | H4USG6 |
| H4YPM0 | L5HV94 | H4YPH3 | I5QW95 | I7WAW3 | A9Z9Y2 |
| E9U9I3 | L1CQU5 | L4QRV7 | L4TFJ6 | D7YA60 | L1CQW4 |
| I2SBG7 | L8S2L4 | J5XTX4 | H4Z4M5 | E9U9G3 | D7YA80 |
| K3R0A0 | K3DX62 | L3ZGY3 | L3KR37 | G5PW35 | K2V9Y3 |
| B2PJH9 | I7W0J5 | G5PW33 | G5PGS6 | L3GF20 | L5EKI8 |
| K5GG82 | L5BZY9 | L1KR74 | K3C1C8 | L3H308 | D8E3L6 |
| C4U4Q1 | I2XLP9 | I5WJG5 | D8E3J4 | H6P1D1 | L3VT02 |
| L5GSI7 | I5TR12 | J1LTN0 | L4NC45 | G5VX93 | L9BGL3 |
| I7WXF3 | I5J6Y3 | L9IJ71 | L2VEC8 | J9WRB0 | I5S9Y5 |
| G1YK68 | H3KCD0 | I5V8Q8 | L9HX28 | L4L951 | L1VUB5 |
| L4AJL2 | I6HT62 | I5HAV4 | I5U539 | I7P7U1 | L9ERL8 |
| G2D7C4 | L4I9E1 | M3V1I3 | H5JRD7 | K5G7H8 | K5FEJ8 |
| L9AVL2 | I5XA14 | F5MT32 | I7W894 | H5JRS9 | L1BGE1 |
| L1BGG3 | K3GB62 | F8YV39 | B1EQG3 | J1NUH4 | L2XN23 |
| I6CJ09 | F4UWB4 | I6CSL5 | J1ZYA9 | L1ED04 | L4T2N7 |
| L3EV49 | L1EE45 | F5PH59 | K2VYG0 | L5A3N0 | L3I4F5 |
| L1FUJ6 | L5EEA8 | L1FUB8 | K3I8N8 | L5EBV4 | L4MLC0 |
| L3SMU3 | G5R8V8 | L1WZ84 | D7YJ24 | L4SIF7 | B3BAY7 |
| I7QIR7 | D7YJ03 | I6E3S5 | I6E2M6 | L1FFZ9 | L1FHA6 |
| L3XNJ9 | L3AIS0 | L3DCM3 | L2ZQW7 | G9Z382 | G9Z6T2 |
| F9B733 | L3CTW1 | K5GGB1 | K5GGC9 | L3RU66 | K5V7V7 |
| B5CDU5 | K2W084 | L3R3T7 | L3H2Z3 | I5KPM2 | G5WDR4 |
| I8HN84 | K2XEQ7 | J1XSN7 | L4B207 | J2LYB6 | L9EWN3 |
| H7E8B6 | H7EFP3 | G2BH56 | I7TE46 | G5N5X9 | I2VCV4 |
| K3R9D0 | K3U183 | L4RNN6 | L3FZ43 | G5XKR7 | F8Z5T6 |
| K5SMQ6 | L4NUX8 | H5HFY0 | L5FEK0 | K3F8X8 | H5HFW1 |
| I7PQR4 | L3LTC8 | L4A672 | G5NWE6 | I2Y4M6 | G5UG24 |
| E7THT7 | J9WX42 | G5NWE4 | K3DHG1 | L4YF33 | K5ERV4 |
| L4IQR3 | L3J974 | K5ERT7 | C4UFE9 | F9AC54 | J1EAB4 |
| F3QA56 | L3PA82 | L4WDV5 | L3CZZ0 | K3MPZ0 | J2LWC7 |
| I7Q7C5 | I8QBE8 | I5L1L1 | L8DAI2 | L3WLQ1 | I5SND2 |
| L8T8F8 | E7T215 | I7W989 | L8QUU4 | L4BBX6 | L5C5U6 |
| E2KBB2 | L9B483 | L9G1R7 | L0Z001 | L4RL04 | L0YXM5 |
| E2X4N1 | L9FCW5 | G5Y4V3 | H1ENB2 | L5AT29 | K2Z1I4 |
| F7N4C2 | E7UCF3 | I8HE83 | K2XZX6 | H1F466 | G6Z285 |
| I5KRA0 | F7N4C1 | L4KGB0 | M1SKM5 | L4QZX7 | M1RQ73 |
| F5P3T9 | L4CN89 | L4V0U9 | L3U4Y7 | I5JAK7 | I7WZT3 |
| G7COI5 | F8XI69 | K3FB12 | L3K5K6 | I6FQ39 | F8ZRQ5 |
| I6FQG6 | I2VUS4 | F8X8V9 | K2XJA0 | L5E756 | L4F8M8 |
| L3ZJ80 | K5H5J8 | L1ZPU4 | F9AYU6 | F4QX28 | H4UB16 |
| L4I150 | L2DP62 | B5PY28 | H4UD30 | L9CGU3 | I6CE72 |
| L1WYU6 | L3Q752 | L4DSI6 | E1I8N2 | I0A439 | I2YEN5 | E1I8Q3 |
| I2XF31 | L2B6G5 | L4DSI6 | I2X267 | K2UME8 | L9HY73 |
| G5S484 | L9G6W1 | G5RY80 | L5J565 | L3UUU8 | L4C5Y5 |
| L4MNW4 | L4DPM8 | L3U3J6 | L4A9T1 | L8RSC0 | B6ZV29 |
| L8SCJ8 | L3L740 | L5D6D0 | K3CQ23 | I6BGH7 | I6KUL9 |
| F4VPI9 | J1P1K1 | G6ZP97 | B5MYN3 | D8BNH2 | L0XFR8 |
| E6AW46 | E6BPS4 | K3EY17 | L0XFT6 | L1DUJ6 | L1DUH5 |
| E9A511 | E6AW24 | E9A9Z5 | E6BPQ3 | I5PCC2 | D8BNF2 |
| D8BKR1 | M1YQ20 | M1YQL5 | H5HXX1 | L5FNP9 | D8EPN7 |
| L4J9M5 | G1ZD77 | H5HXV2 | I5FZI4 | G5MBY2 | D8EPL5 |
| F1XKZ5 | L3R5N4 | I2PFB7 | K3CLI6 | I8GHM8 | G5YAK0 |
| I5Z8Y0 | L0YEQ2 | L5GS53 | L0YFU2 | L2Z6T1 | I7YZ57 |
| J1GJF9 | K3SPI8 | L1R4J3 | L1R4N9 | B0H3G9 | L8R4H6 |
| D0YZT1 | L8ZV52 | E2KS00 | G7ATI2 | B3I3F2 | I7NQ44 |
| L4FPP1 | L1YEC5 | L3G7A2 | L4PN37 | E2JZ15 | G7BEV7 |
| L2CG18 | K6BMP2 | K3IBQ9 | L4NAX4 | L4UVT9 | L1YFF5 |
| K6AQQ4 | E7SMJ3 | H4LD96 | I5TK17 | K2YQG0 | B5N8X1 |
| D4BKK1 | H4LD94 | L1ZB17 | L5FGA8 | L2VPB6 | I5UWQ2 |
| G7BSL0 | K2W4M5 | G2A7N1 | I8ABI5 | E6A679 | L3EMC4 |
| B5BW09 | J1EEU3 | J9XAE9 | G2BXS5 | L8ZU36 | I2RDZ7 |
| E6A6A0 | L5BAV4 | L1D8C7 | L1D8A4 | F9BI15 | L9GKG1 |
| G5TR25 | I5GHK7 | E7IWX0 | L5HY14 | K3BUT3 | I5JSB7 |
| I5PZ94 | L4HCK1 | L9DIV7 | B0HU12 | I8R9N2 | F9BVG9 |
| B4AA00 | J9WX07 | D7Z320 | L3W464 | L4WBE5 | D7XTM6 |
| L1VQ23 | D7XTK5 | D7Z341 | I5YHQ1 | F4VMA3 | K3MDC6 |
| F5NAH0 | K3KB42 | L9AF12 | L4DM02 | L1X3N5 | H5ISJ7 |
| B3A6E6 | I2DXM6 | I6D2V7 | I6D2V9 | H1BTG9 | H5ISL6 |
| I2WGN2 | I6D2W0 | I6CR58 | K5FVW8 | K5HMA4 | K5HM79 |
| I7TD77 | I2Z670 | I5EQF3 | K2T9K2 | I7Z9Z3 | I6J638 |

-continued

| | | | | | |
|---|---|---|---|---|---|
| F8ZDV2 | L9CEA9 | B3B061 | E7HSW8 | K3MX00 | F4TP19 |
| K2V813 | L4K1S5 | L3PUI4 | H4J2D2 | G2AP22 | H4J2B4 |
| E7IDB4 | E2X267 | F5PWY4 | J9X778 | D8CBL7 | L1Y967 |
| L4KWW5 | L0ZZ14 | L0ZZ44 | D7X582 | L4XFS7 | L3UDG0 |
| L4EEY0 | D8CBN6 | I5NVZ9 | I2TLP7 | D7X560 | L5HPI1 |
| H5IBZ7 | L2WC77 | I6J919 | L9CH33 | H5IBX8 | J1LJU9 |
| I5HMY4 | L2D672 | L4QAI1 | L1CM27 | L3PH92 | L1CMJ2 |
| L2TZ71 | L9DKJ3 | F4U276 | K2W210 | C4S0N7 | L4MQ21 |
| L3YTD0 | K3GPD1 | K3NAF9 | G6ZZN4 | J1D607 | L2VLJ7 |
| L5GJS3 | K3P2I6 | L1VS42 | L3ITJ5 | D8AFI1 | D8AFF8 |
| D8AFF9 | B3HVQ4 | F4SSI1 | L4GNN4 | L3UXG7 | G4C9J0 |
| E7HCX1 | G4C3K1 | C3SGT2 | C6ED09 | A9ANX5 | B1LQD3 |
| A4JQ30 | B7NG51 | G8W1Q4 | B4TED3 | B7MSM8 | D2TNK2 |
| A9R299 | D3GTZ4 | B4TS79 | B5F2H0 | D2ADB4 | B7M8M5 |
| Q399G7 | E1WEY4 | B2TXC1 | Q0B7H7 | B7NSS7 | B7LB57 |
| B4T2J5 | E3PD34 | A8A7L1 | F8L8H9 | F8L8H8 | B5Z2C3 |
| A7ZUY5 | E8P6N2 | B5FRG8 | E8P6N3 | A7FKG8 | B7MJY9 |

In some embodiments, an arginine agmatine antiporter of the invention is from a *Salmonella* species. In particular embodiments, an arginine agmatine antiporter of the invention is from a *Salmonella Typhi* strain. In still other embodiments, an arginine agmatine antiporter of the invention is from a *S. Typhi* Ty2 strain. In an exemplary embodiment, an arginine agmatine antiporter of the invention has the amino acid sequence of the protein at accession number P60065.

In certain embodiments of the invention the nucleic acid encoding an arginine agmatine antiporter is fused with an arginine decarboxylase encoding sequence such that the intervening regulatory gene adiY is deleted. For instance, in certain embodiments, a *Salmonella* adiA sequence is fused to a *Salmonella* adiC sequence.

iv) A Nucleic Acid Encoding a Glutamate Decarboxylase

In some embodiments, a regulatable cassette may comprise a glutamate decarboxylase. A glutamate decarboxylase is an enzyme that catalyzes the chemical reaction L-glutamate ↔ γ-aminobutyric acid (GABA) and $CO_2$, and is classified as EC 4.1.1.15. Generally speaking, a glutamate decarboxylase useful in the present invention will have activity similar to GadA and/or GadB (e.g. protect a cell from low pH). Suitable examples of glutamate decarboxylase are known in the art, and may include the following enzymes (referenced by UNIPROT identifiers, available at www.uniprot.org): GadB-P69910, O30418, Q928R9, P69909, P69912; GadA-P69908, Q83QR1, P58288, P69912, or Q9F5P3.

In some embodiments, a glutamate decarboxylase of the invention is from *Escherichia coli*. In particular embodiments, a glutamate decarboxylase of the invention is from an *Escherichia coli* O157 strain. In still other embodiments, a glutamate decarboxylase of the invention is from a *Shigella* species. In some embodiments, two glutamate decarboxylases may be present in the same strain (GadA and GadB). In an exemplary embodiment, a glutamate decarboxylase of the invention has the amino acid sequence of P69910.

v) A Nucleic Acid Encoding a Glutamate/γ-Aminobutyric Acid Antiporter

In other embodiments, a regulatable cassette of the invention may comprise a glutamate/γ-aminobutyric acid antiporter. A glutamate/γ-aminobutyric acid antiporter exchanges extracellular glutamate for its intracellular decarboxylation product/γ-aminobutyric acid thereby expelling intracellular protons. Generally speaking, a glutamate/γ-aminobutyric acid antiporter useful in the present invention will have activity similar to GadC (e.g. protect a cell from low pH). Suitable examples of a glutamate/γ-aminobutyric acid antiporter are known in the art, and may include the following enzymes (referenced by UNIPROT identifiers, available at www.uniprot.org): C8U8G2, C6UU78, P58229, P63235, Q8FHG6, E0J6C9, C9QVX6, Q9CG19, O30417, C7LHI1, Q8YBJ1, Q577E9, C4PPM2, B1LFC4, B0BBJ6, B7LZ92, B7L7J1, B6J3P9, Q03U70, A8A049, B0B9W6, E1P9D3, Q3KME6, D5D2L2, C8U8G2, or B7LRF2.

In some embodiments, a glutamate/γ-aminobutyric acid antiporter of the invention may be from *Escherichia coli*. In particular embodiments, a glutamate/γ-aminobutyric acid antiporter of the invention is from an *Escherichia coli* O157 strain. In still other embodiments, a glutamate/γ-aminobutyric acid antiporter of the invention is from a *Shigella* species. In an exemplary embodiment, a glutamate/γ-aminobutyric acid antiporter of the invention has the amino acid sequence of a protein with accession number C6UU78.

vi) A Nucleic Acid Encoding a Lysine Decarboxylase

In certain embodiments, a regulatable cassette of the invention further comprises a lysine decarboxylase. A lysine decarboxylase is an enzyme that catalyzes the chemical reaction L-lysine ↔ cadaverine and $CO_2$, and is classified as EC 4.1.1.18. Generally speaking, a lysine decarboxylase useful in the present invention will have activity similar to CadA (e.g. protect a cell from low pH). Suitable examples of lysine decarboxylase are known in the art, and may include the following enzymes (referenced by UNIPROT identifiers, available at www.uniprot.org): P0A1Z1, Q8X8X4, P0A9H4, or C5A1C4.

In some embodiments, a lysine decarboxylase of the invention is from a *Salmonella* species. In particular embodiments, a glutamate decarboxylase of the invention is from *Salmonella Typhi*. In other embodiments a lysine decarboxylase of the invention is from an *Escherichia coli* strain. In an exemplary embodiment, a lysine decarboxylase of the invention has the amino acid sequence of P0A1Z1.

vii) A Nucleic Acid Encoding a Lysine/Cadaverine Antiporter

A regulatable cassette of the invention comprises lysine/cadaverine antiporter. A lysine/cadaverine antiporter exchanges extracellular lysine for its intracellular decarboxylation product cadaverine thereby expelling intracellular protons. Generally speaking, a lysine/cadaverine antiporter useful in the present invention will have activity similar to CadB (e.g. protect a cell from low pH). Suitable examples of a lysine/cadaverine antiporter are known in the art, and may include the following enzymes (referenced by UNIPROT identifiers, available at www.uniprot.org): Q8Z4M1, P0AAF0, P0AAE8, J9ZST9, K0AT87, K0BD30, D3QL54, Q5PIH7, or B5QTS6.

In some embodiments, a lysine/cadaverine antiporter of the invention is from *Salmonella* species. In particular embodiments, a lysine/cadaverine antiporter of the invention is from *Salmonella Typhi*. In other embodiments a lysine/cadaverine antiporter of the invention is from *Escherichia coli*. In an exemplary embodiment, a lysine/cadaverine antiporter of the invention has the amino acid sequence of Q8Z4M1.

viii) A Nucleic Acid Encoding a Chloride Channel

In some embodiments, a regulatable cassette of the invention comprises a chloride channel protein. A chloride channel prevents membrane hyperpolarization at low pH. Generally speaking, a chloride channel protein useful in the present invention will have activity similar to ClcA from *E. coli*. Suitable examples of a chloride channel are known in the art, and may include the following (referenced by UNIPROT identifiers, available at www.uniprot.org): P37019, Q3Z5K2, Q8ZBM0, Q1RG33, B7LWB6, B5Y1L4, Q325Y4, Q32JV3, Q0T851, P59639, A5F0D5, Q9KM62, C3LVE3, Q87GZ9, Q7MDF0, A7FM08, Q1C3×2, A9R1E4, Q1CLU6, B1IQI5, A6T4V9, B2U300, A7N6K9, Q8D6J0, B2K549, A4TPW7, B1JK21.

In some embodiments, a chloride channel of the invention is from *Escherichia* species. In particular embodiments, a chloride channel of the invention is from *E coli*. In other embodiments, a chloride channel of the invention is has significant homology with the *E. coli* chloride channel, ClcA. A skilled artisan would be able to identify those proteins with significant homology to an *E. coli* chloride channel. In an exemplary embodiment, the chloride channel of the invention has the amino acid sequence of P37019.

ix) Nucleic Acids Encoding a Urease System

In some embodiments, a regulatable cassette of the invention comprises all or some of a Ni-dependent urease system. A Ni-dependent urease system enables survival in extremely low pH by acid acclimation. Generally speaking, a Ni-dependent urease system useful in the present invention has activity similar to the *Helicobacter pylori* Ni-dependent urease system. The regulatable cassette may comprise urease proteins, such as UreA and UreB, and a carbonic anhydrase, such as HP1186. Additional components of the urease system, such as a proton-gated urea channel (UreI) and a chaperone complex necessary to incorporate Ni ions into the urease apoenzyme (UreE, UreF, UreG, UreH) may be under control of a constitutive promoter. Constitutive promoters are known in the art and may include $P_{lpp}$.

In some embodiments, a Ni-dependent urease system of the invention is from *Helicobacter* species. In an exemplary embodiment, the Ni-dependent urease system of the invention is from *H. pylori*.

x) Transcription Termination Sequence

In some embodiments, the regulatable cassette further comprises a transcription termination sequence. A transcription termination sequence may be included to prevent inappropriate expression of nucleic acid sequences adjacent to the cassette.

(b) Acid Sensitive/Increase in Acid Resistance

In some embodiments, a recombinant bacterium of the invention is acid sensitive. As used herein, "acid sensitive" means that when cells are cultured under aerobic conditions in minimal media and in the absence of induction of the regulatable cassette, less than 1% of the bacteria are viable after 4 hours at pH3.

In some embodiments, the bacterium may be acid sensitive due to a loss of function of the acid tolerance response. In other embodiments, the bacterium may be acid sensitive due to loss of function of an acid resistance system such as the arginine decarboxylase or lysine decarboxylase system. Such "loss of function" may be caused by one or more mutations in the acid tolerance response, the arginine decarboxylase acid resistance system, the lysine decarboxylase system, or related systems that result in acid sensitivity. In an alternative embodiment, the bacterium may contain no mutation, but be acid sensitive due to exposure to environmental conditions that repress or fail to induce the acid tolerance or acid resistance systems.

In one embodiment, the bacterium may be acid sensitive, at least in part, because of an rpoS mutation. In another embodiment, the bacterium may be acid sensitive, at least in part, because of a phoPQ mutation. In still another embodiment, the bacterium may be acid sensitive, at least in part, because of a fur mutation. In still yet another embodiment, the bacterium may be acid sensitive, at least in part, because of a guaBA mutation.

Advantageously, an acid sensitive bacterium of the invention increases its acid resistance when the regulatable promoter is induced. As used herein "an increase in acid resistance" means that after induction of the regulatable cassette, when cells are cultured under aerobic conditions in minimal media and challenged at pH 3.0 for 4 hours, the number of viable bacteria after 4 hours is increased >10-fold compared to the parent strain lacking the acid resistance system. In some embodiments, induction of the regulatable promoter results in the same degree of acid resistance as the wild-type strain (e.g. without a mutation(s) that confers acid sensitivity). In other embodiments, induction of the regulatable promoter results in a greater degree of acid resistance than the wild-type strain.

(c) Other Mutations

A bacterium of the invention may comprise one or more mutations desirable in a bacterium used to evoke an immune response, such as in a vaccine. In particular, a bacterium may comprise one or more mutations to increase invasiveness, one or more mutations to allow endosomal escape, one or more mutations to reduce bacterium-induced host programmed cell death, one or more mutations to induce lysis of the bacterium, one or more mutations to express a nucleic acid encoding an antigen, one or more mutations to attenuate the bacterium, and/or other mutations to enhance the performance of the bacterium as a vaccine.

(d) Exemplary Embodiments

In exemplary embodiments of the present invention, the recombinant bacterium is a *Salmonella Typhi* bacterium adapted for use as a live attenuated vaccine. In further exemplary embodiments, the arginine decarboxylase and the arginine agmatine antiporter comprising the regulatable cassette are derived from a *Salmonella* bacterium. In still further exemplary embodiments, the arginine decarboxylase and the arginine agmatine antiporter comprising the regulatable cassette are adiA and adiC from *Salmonella Typhi*. In some embodiments, the clcA gene from *E. coli* is present in the chromosome and transcribed from its own native promoter, a heterologous constitutive promoter or a heterologous regulatable promoter.

In still another embodiment, a recombinant bacterium of the invention may comprise a mutation in at least one of aroD, guaBA, rpoS, fur, or phoPQ. In some embodiments, the regulatable acid resistance cassette is regulated by a sugar-inducible promoter. The recombinant bacterium is acid sensitive in the absence of inducer for the regulatable acid resistance cassette. In particular embodiments, the regulatory promoter is responsive to the presence of rhamnose or arabinose. In some embodiments, the acid resistance mechanism comprises a $\Delta P_{cadBA}$::TT rhaSR $P_{rhaBAD}$ cadBA or $\Delta P_{cadBA}$::TT araC $P_{araBAD}$ cadBA mutation.

In further exemplary embodiments, the lysine decarboxylase and the lysine: cadaverine antiporter comprising the regulatable cassette are derived from a member of the γ-proteobacteria class. In other exemplary embodiments, the lysine decarboxylase and the lysine: cadaverine antiporter are cadA and cadB from *Salmonella*. In still further exemplary embodiments, cadA and cadB are derived from *Salmonella Typhi*. In some embodiments, the clcA gene from *E. coli* is present in the chromosome and transcribed from its own native promoter, a heterologous constitutive promoter or a heterologous regulatable promoter.

In a different exemplary embodiment, the regulatable acid resistance cassette is regulated by a sugar-inducible promoter. The recombinant bacterium is acid sensitive in the absence of inducer for the regulateable acid resistance cassette. In particular embodiments, the promoter is responsive to the presence of rhamnose or arabinose. In further exemplary embodiments, the glutamate decarboxylase and the glutamate/γ-aminobutyric acid antiporter comprising the regulatable cassette are derived from a bacterium of the γ-proteobacteria class. In still further exemplary embodiments, the glutamate decarboxylase and the glutamate/γ-aminobutyric acid antiporter comprising the regulatable cassette are from *Escherichia coli*. In particular embodiments, a glutamate decarboxylase of the invention is from an *Escherichia coli* O157:H7 strain. In still other embodiments, a glutamate decarboxylase of the invention is from a *Shigella* species. In some embodiments, two glutamate decarboxylases may be present in the same strain (GadA and GadB). In some embodiments, the clcA gene from *E. coli* is present in the chromosome and transcribed from its own native promoter, a heterologous constitutive promoter or a heterologous regulatable promoter.

In a different embodiment, a recombinant bacterium of the invention comprises a mutation in at least one of aroD, guaBA, rpoS, fur, or phoPQ. In some embodiments, the regulatable acid resistance cassette is regulated by a sugar-inducible promoter. The recombinant bacterium is acid sensitive in the absence of inducer for the regulateable acid resistance cassette. In particular embodiments, the promoter is responsive to the presence of rhamnose or arabinose. In some exemplary embodiments, the acid resistance mechanism is composed of a urease enzyme. In further embodiments, accessory proteins such as a proton-gated urea channel, carbonic anhydrase or enzyme chaperones will comprise additional components of the acid resistance mechanism. In particular embodiments, the urease, urease channel, carbonic anhydrase and apoenzyme chaperones are derived from a *Helicobacter* species. In other specific embodiments, the components that comprise the acid resistance mechanism are UreA, UreB, UreI, UreE, UreF, UreG, UreH and HP1186 from *Helicobacter pylori*.

In several exemplary embodiments, a recombinant bacterium of the invention is acid sensitive, is a *Salmonella Typhi* bacterium adapted for use as a live attenuated vaccine, and the arginine decarboxylase and the arginine agmatine antiporter comprising the regulatable cassette are adiA and adiC from *Salmonella Typhi*.

In one exemplary embodiment, a recombinant bacterium of the invention comprises a mutation in at least one of aroD, guaBA, rpoS, fur, or phoPQ that renders the bacterium acid sensitive in the absence of rhamnose, and comprises a $\Delta P_{adiA}$::TT rhaSR $P_{rhaBAD}$ adiAC mutation.

In another exemplary embodiment, a recombinant bacterium of the invention comprises a mutation in at least one of aroD, guaBA, rpoS, fur, or phoPQ that renders the bacterium acid sensitive in the absence of arabinose, and comprises a $\Delta P_{adiA}$::TT araC $P_{araBAD}$ adiAC mutation.

In several exemplary embodiments, a recombinant bacterium of the invention is acid sensitive, is a *Salmonella Typhi* bacterium adapted for use as a live attenuated vaccine, and the glutamate decarboxylase and a glutamate/γ-aminobutyric acid antiporter comprising the regulatable cassette are gadB and gadC from *Escherichia coli*.

In one exemplary embodiment, a recombinant bacterium of the invention comprises a mutation in at least one of aroD, guaBA, rpoS, fur, or phoPQ that renders the bacterium acid sensitive in the absence of rhamnose, and comprises a $\Delta P_{gadB}$::TT rhaSR $P_{rhaBAD}$ gadBC mutation.

In another exemplary embodiment, a recombinant bacterium of the invention is a *S. Typhi* strain comprising a mutation in at least one of aroD, guaBA, rpoS, fur, or phoPQ that renders the bacterium acid sensitive in the absence of arabinose, and comprises a $\Delta$cysG::TT araC $P_{BAD}$ gadBC mutation.

In still another exemplary embodiment, a recombinant bacterium of the invention comprises a mutation in at least one of aroD, guaBA, rpoS, fur, or phoPQ that renders the bacterium acid sensitive in the absence of arabinose, and comprises a $\Delta P_{gadB}$::TT araC $P_{BAD}$ gadBC mutation.

In several exemplary embodiments, a recombinant bacterium of the invention is acid sensitive, is a *Salmonella Typhi* bacterium adapted for use as a live attenuated vaccine, and the lysine decarboxylase and a lysine/cadaverine antiporter comprising the regulatable cassette are cadB and cadA from *Salmonella Typhi*.

In one exemplary embodiment, a recombinant bacterium of the invention comprises a mutation in at least one of aroD, guaBA, rpoS, fur, or phoPQ that renders the bacterium acid sensitive in the absence of rhamnose, and comprises a $\Delta P_{cadB}$::TT rhaSR $P_{rhaBAD}$ cadBA mutation.

In another exemplary embodiment, a recombinant bacterium of the invention comprises a mutation in at least one of aroD, guaBA, rpoS, fur, or phoPQ that renders the bacterium acid sensitive in the absence of arabinose, and comprises a $\Delta P_{cadB}$::TT araC $P_{BAD}$ cadBA mutation.

In still another exemplary embodiment, a recombination bacterium of the invention is a *Salmonella enterica* serovar Gallinarum (*S. Gallinarum*) comprising a mutation in at least one of pmi or fur that renders the bacterium sensitive in the absence of arabinose, and comprises a $\Delta$cysG::TT araC $P_{BAD}$ gadBC mutation.

In other exemplary embodiments, a recombinant bacterium of the invention is a *Salmonella enterica* serovar Dublin (*S. Dublin*) comprising a $\Delta P_{adiA}$::TT rhaSR $P_{rhaBAD}$ adiA $\Delta(P_{adiY}$::-adiY-$P_{adiC})$ adiC mutation or a $\Delta$cysG::TT araC $P_{BAD}$ gadBC mutation.

II. Vaccine Compositions and Administration

A recombinant bacterium of the invention may be administered to a host as a vaccine composition. As used herein, a vaccine composition is a composition designed to elicit an immune response to the recombinant bacterium, including any antigens that may be expressed by the bacterium. In an exemplary embodiment, the immune response is protective, as described above. Immune responses to antigens are well studied and widely reported. A survey of immunology is given by Paul, W E, Stites D et. al. and Ogra P L. et. al. Mucosal immunity is also described by Ogra P L et. al.

Vaccine compositions of the present invention may be administered to any host capable of mounting an immune response. Such hosts may include all vertebrates, for example, mammals, including domestic animals, agricultural animals, laboratory animals, and humans, and various species of birds, including domestic birds and birds of agricultural importance. Preferably, the host is a warm-blooded animal. The vaccine can be administered as a prophylactic or for treatment purposes.

In exemplary embodiments, the recombinant bacterium is alive when administered to a host in a vaccine composition of the invention. In further exemplary embodiments, a recombinant bacterium comprising a vaccine of the invention is derived from *Salmonella Typhi*. In still further exemplary embodiments, a recombinant bacterium comprising a vaccine of the invention is derived from *Salmonella Typhi* Ty2. Suitable vaccine composition formulations and methods of administration are detailed below.

(a) Vaccine Composition

A vaccine composition comprising a recombinant bacterium of the invention may optionally comprise one or more possible additives, such as carriers, preservatives, stabilizers, adjuvants, and other substances.

In one embodiment, the vaccine comprises an adjuvant. Adjuvants, such as aluminum hydroxide or aluminum phosphate, are optionally added to increase the ability of the vaccine to trigger, enhance, or prolong an immune response. In exemplary embodiments, the use of a live attenuated recombinant bacterium may act as a natural adjuvant. The vaccine compositions may further comprise additional components known in the art to improve the immune response to a vaccine, such as T cell co-stimulatory molecules or antibodies, such as anti-CTLA4. Additional materials, such as cytokines, chemokines, and bacterial nucleic acid sequences naturally found in bacteria, like CpG, are also potential vaccine adjuvants.

In another embodiment, the vaccine may comprise a pharmaceutical carrier (or excipient) used to resuspend the lyophilized RASV. Live RASVs are generally lyophilized in the presence of various types of protectants, very often sugars, than enhance thermal stability and are reconstituted at time of use. Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the vaccine is preferably presented in the form of an aerosol.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the vaccine formulation against a variety of conditions, such as temperature variations or a freeze-drying process.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

In an embodiment, a vaccine composition of the invention may be administered in combination with a compound to reduce the pH of the gastric components. The compound may be used to buffer the stomach pH of a subject. Buffering the pH of the stomach may further enhance the immune response elicited in response to a vaccine composition. In an exemplary embodiment, Ensure® may be administered in combination with a vaccine composition. In another exemplary embodiment, sodium bicarbonate may be administered in combination with a vaccine composition.

(b) Methods of Administration

In order to stimulate a preferred response of the GALT, NALT or BALT cells, administration of the vaccine composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

III. Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

IV. Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to physicians and other skilled practitioners. For instance, assays such as ELISA, and ELISPOT may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, the invention provides a method for eliciting an immune response against an antigen in a host. The method comprises administering to the host an effective amount of a composition comprising a recombinant bacterium of the invention.

In still another embodiment, a recombinant bacterium of the invention may be used in a method for eliciting an immune response against a pathogen in an individual in need thereof. The method comprises administrating to the host an effective amount of a composition comprising a recombinant bacterium as described herein. In a further embodiment, a recombinant bacterium described herein may be used in a method for ameliorating one or more symptoms of an infectious disease in a host in need thereof. The method comprises administering an effective amount of a composition comprising a recombinant bacterium as described herein.

In a further embodiment, the present invention encompasses a method for increasing the acid resistance of an acid sensitive bacterium. The method comprises introducing into the acid sensitive bacterium a cassette comprising a regulatable promoter operable linked to an arginine decarboxylase and an arginine agmatine antiporter as described in Section I above. Alternatively, the method comprises introducing into the acid sensitive bacterium a cassette comprising a regulatable promoter operable linked to a glutamate decarboxylase and a glutamate/γ-aminobutyric acid antiporter as described in Section I above. In another embodiment, the method comprises introducing into the acid sensitive bacterium a cassette comprising a regulatable promoter operable linked to a lysine decarboxylase and a lysine/cadaverine antiporter as described in Section I above. Upon induction of the regulatable promoter, the recombinant bacterium experiences an increase in acid resistance. In some variations of these embodiments, the regulatable promoter may be induced by a sugar, such as rhamnose or arabinose. In other variations of these embodiments, the recombinant bacterium comprises a mutation in at least one nucleic acid sequence selected from the group consisting of aroD, guaBA, rpoS, fur, and phoPQ.

In yet still another embodiment, the present invention encompasses a method of increasing the survival of probiotic bacteria during passage throught the stomach. The method comprises introducing into the probiotic bacterium a cassette comprising a regulatable promoter operable linked to an arginine decarboxylase and an arginine agmatine antiporter as described in Section I above. Alternatively, the method comprises introducing into the probiotic bacterium a cassette comprising a regulatable promoter operable linked to a glutamate decarboxylase and a glutamate/γ-aminobutyric acid antiporter as described in Section I above. In another embodiment, the method comprises introducing into the probiotic bacterium a cassette comprising a regulatable promoter operable linked to a lysine decarboxylase and a lysine/cadaverine antiporter as described in Section I above. Upon induction of the regulatable promoter, the recombinant bacterium experiences an increase in acid resistance. In some variations of these embodiments, the regulatable promoter may be induced by a sugar, such as rhamnose or arabinose. According to this method, the probiotic bacterium survives the low pH stomach environment and effectively colonizes the subject.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that may changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples are simply intended to further illustrate and explain the present invention. The invention, therefore, should not be limited to any of the details in these examples.

Introduction

Before orally ingested enteric pathogens such as *Salmonella* can reach their target host cells, they must first survive their encounter with the low pH of the human stomach; approximately 2.0 following a fast (1). This is an extremely hostile environment for wild-type *Salmonella*, thus *Salmonella* contains multiple regulatable systems to aid in survival at low pH (2, 3). The best studied of these systems is the acid tolerance response (ATR). Cells exposed to moderately low pH synthesize numerous acid shock proteins. Although the specific functions of these proteins are largely unknown, jointly they mitigate the proton damage experienced by the cell during low pH challenge (pH 3.0) (4, 5). The acid tolerance response is a complex multi-component system coordinated by a number of global regulatory proteins. In stationary phase, RpoS is a key regulator of the acid tolerance response. Not only does the acid tolerance response of an rpoS mutant fail to provide the same level of protection as in a wild-type strain, but rpoS mutants are unable to sustain the acid tolerance response, resulting in rapid cell death upon pH 3.0 challenge (4, 6). In log phase cells, the *Salmonella* virulence proteins PhoP/PhoQ and Fur regulate the acid tolerance response. Fur controls a subset of acid shock proteins essential for protecting the cell against organic acid challenge while PhoP/PhoQ coordinates protection against inorganic acid challenge (7, 8).

The vast majority of live attenuated *Salmonella* vaccines for humans are constructed from *Salmonella Typhi* strain Ty2, an rpoS mutant (9). To create a vaccine, additional attenuating mutations are necessary in virulence genes. However, these mutations can affect more than just virulence. In addition to the rpoS mutation derived from its parent strain Ty2, the licensed typhoid vaccine strain Ty21a carries galE and tvi mutations as well as a number of other, less well-characterized, mutations (10-12). The strain is sensitive to low pH, due at least in part to its inability to mount a functional acid tolerance response (13). Another vaccine strain, Ty800, contains a deletion of the phoPQ locus. This strain is safe and reasonably immunogenic in humans (14), but one would expect that the combination of the phoPQ deletion and rpoS mutation would render this strain exquisitely sensitive to acidic pH (6, 8). A similar situation occurs for the vaccine strains χ9639 (pYA4088) and χ9640 (pYA4088) (15). These strains are also safe and immunogenic in humans (69), but the mutation in their fur locus leaves them vulnerable to low pH.

Most vaccine researchers avoid the problem low gastric pH poses by coating their vaccine in a protective enteric capsule (e.g. Ty21a) or by co-administering an antacid (usually sodium bicarbonate) at the time of immunization (16-21). Preventing vaccine exposure to low pH increases the number of viable cells that reach the intestine and improves vaccine immunogenicity (21, 22). The disadvantage of bypassing the acidic environment of the stomach is that the low pH encounter serves as an important signal to *Salmonella*, allowing it to recognize entry into a host environment. Exposure to acid stimulates up-regulation of the genes that confer resistance to the short chain fatty acids (23), antimicrobial peptides (24) and osmotic stress (6) found in the intestine. Also, induction of the acid tolerance response has been linked to upregulation of SPI-1 and SPI-2 and an increase in epithelial cell invasion in the intestine (25-27). Thus, transient exposure to low pH prepares the invading bacteria for the stresses of the intestine and for host-cell interactions. Therefore, it is possible that if we can enhance the survival rate of live attenuated *Salmonella* vaccine strains at low pH, we can not only eliminate the need for low pH bypass strategies but also improve the ability of the vaccine strain to interact with host tissues to enhance immunogenicity.

As a first step toward this goal, we explored methods to increase the low pH survival of *S. Typhi* strains containing rpoS, phoPQ or fur mutations, because each renders strains acid sensitive and each has been incorporated into live attenuated vaccine strains. One robust means used by *Salmonella* to resist low pH challenge is the arginine decarboxylase acid resistance system (AR3) (28). This system consists of arginine decarboxylase (AdiA) and an arginine-agmatine antiporter (AdiC) (29). Acid resistance is conferred by the activity of AdiA, which consumes one proton from the intracellular environment with each reaction cycle and causes a rapid rise in intracellular pH (30, 31). AdiC then exchanges the agmatine reaction product to the periplasm in exchange for another arginine substrate molecule (29, 32). The combined activities of AdiA and AdiC allow Salmonella to resist pH 2.5 for greater than two hours (3).

Because the arginine decarboxylase system functions independently of the acid tolerance response, we hypothesized that synthesis of AdiA and AdiC would confer high levels of acid resistance on strains containing mutations that affect acid tolerance such as rpoS, phoPQ and fur. However, the arginine decarboxylase system is tightly regulated and is not normally available to cells grown under standard vaccine culture conditions (33). Therefore, we replaced the native promoter of arginine decarboxylase with the araBAD or rhaBAD promoter and compared the level of arginine decarboxylase activity when cells were cultured in the presence of arabinose and rhamnose, respectively. Once we selected the promoter with optimal sugar-dependent expression and activity of the arginine decarboxylase system ($P_{rhaBAD}$), our objectives were two-fold. First, we determined if the rhamnose-regulated arginine decarboxylase system could rescue rpoS, phoPQ and fur mutants during low pH challenge if cells were cultured in the presence of rhamnose but without any other environmental signals that would induce either decarboxylase activity or the acid tolerance response. Second, to determine whether the rhamnose-regulated system functioned equivalently to the native arginine decarboxylase system, we compared the level of acid resistance afforded by the rhamnose-dependent arginine decarboxylase system with the acid resistance of rpoS, phoPQ and fur mutants cultured under decarboxylase- and acid tolerance-inducing conditions.

Materials and Methods

DNA Manipulation and Plasmid Construction. Chromosomal DNA from S. Typhi Ty2 was isolated using the Wizard Genomic DNA Purification kit (Promega, Madison, Wis., USA). Plasmid DNA was isolated using QIAprep Spin Miniprep kit (QIAGEN, Valencia, Calif., USA) or the Wizard Plus Midiprep DNA Purification system (Promega). DNA inserts were amplified by PCR using the Phusion DNA polymerase (New England Biolabs, Ispwich, Mass., USA) or the Easy-A high-fidelity PCR cloning enzyme (Agilent, Santa Clara, Calif., USA). Restriction and modification enzymes for cloning (New England Biolabs) were used in accordance with the manufacturer's instructions.

Construction of S. Typhi Mutants. The bacterial strains and plasmids used in this study are listed in Table 1. Primers used during the construction of plasmids are listed in Table 2. To construct the ΔaroD mutation, two DNA fragments adjacent to the aroD gene were amplified from the chromosome of Ty2. Primers Aro-1 and -2 were used for the upstream fragment, while primers Aro-3 and -4 were used for the downstream fragment. These fragments were digested with BamHI, ligated using T4 DNA ligase, re-amplified by PCR with primers Aro-1 and -4 and cloned into the AhdI sites of pYA4278 via TA overhangs to generate the suicide vector pYA4895. The ΔaroD deletion was introduced into Ty2 by conjugation as described by Kaniga (34). The resulting strain (χ11548) exhibits aromatic amino acid auxotrophy and carries a deletion of the complete coding sequence of aroD that spans 759 bp.

An arabinose-regulated fur mutant was constructed via P22 HT int transduction (35) using a lysate grown on χ9269 containing a chromosomally integrated copy of pYA4181 (36) to create the S. Typhi strain χ11118. The presence of the $\Delta P_{fur}$::TT araC $P_{BAD}$ fur mutation in S. Typhi was confirmed by PCR using the primers Fur-1 and -2. Arabinose-dependent synthesis of Fur was verified by western blot.

To remove the entire adi locus (Δ(adiA-adiC)), the upstream and downstream flanking regions in Ty2 were amplified using PCR primers Adi-1 and -2 and primers Adi-3 and -4, respectively. The flanking regions were digested with BamHI and ligated together with T4 DNA ligase. The resulting product was re-amplified by PCR using primers Adi-1 and -4 and cloned into the AhdI sites of pYA4278 to generate the suicide vector pYA5066. The Δ(adiA-adiC) mutation (hereafter (ΔadiA-adiC) encoded by pYA5066 was moved into Ty2 to create χ11500. This strain carries a 4806-bp deletion of the adi locus (complete coding sequences of adiA, adiY and adiC along with the adiY and adiC promoters) (FIG. 1). The absence of the adi locus was confirmed by PCR and by arginine decarboxylase assay.

Two mutations were constructed that placed adiA under the control of sugar-responsive promoters—$\Delta P_{adiA}$::TT araC $P_{araBAD}$ adiA (regulated by arabinose) and $\Delta P_{adiA}$::TT rhaSR $P_{rhaBAD}$ adiA (regulated by rhamnose). For simplicity, these mutations will be referred to as $P_{araBAD}$ adiA and $P_{rhaBAD}$ adiA, respectively. For the arabinose-regulated construct, the DNA regions flanking the adiA promoter were amplified by PCR from Ty2 using primers Adi-5 and -6 for the upstream region and primers Adi-7 and -8 for the downstream region. Both flanking regions were cloned into pYA3700 (using SphI and BglII for the upstream region and KpnI and SacI for the downstream region) to generate pYA5075. The DNA segment containing the flanking regions and arabinose promoter was amplified by PCR using Adi-5 and -8 and the PCR product was cloned into the AhdI sites of pYA4278 to create the suicide vector pYA5089. To generate the rhamnose-regulated construct, the araC $P_{araBAD}$ promoter of pYA5089 was removed by XhoI and XbaI double digestion. The rhaSR $P_{rhaBAD}$ promoter from pYA5081 was amplified by PCR with the Rha-1 and -2 primers and cloned into pYA5089 using XhoI and XbaI to produce the suicide vector pYA5093. pYA5089 and pYA5093 were introduced into χ11548 by conjugation to produce χ11552 and χ11564, respectively. The juxtaposition of adiA with the appropriate promoter was verified by PCR with the Ara-1 and Adi-9 primers (χ11552) or Rha-3 and Adi-9 primers (χ11564) and by arginine decarboxylase assay. In both strains, 203 bp of the intergenic region between melR and adiA (including the −10 and -35 sites of the adiA promoter) were deleted and replaced with either TT araC $P_{araBAD}$ (χ11552) or TT rhaRS $P_{rhaBAD}$ (χ11564). The strong transcription terminator T4 ip III was placed between the upstream melR gene and araC or rhaSR to prevent expression of anti-sense RNA. A strong Shine-Dalgarno site (AGGA) was inserted 10 bp upstream of the ATG start codon of adiA (FIG. 1).

The adiC gene was fused into an operon with adiA resulting in the $\Delta(P_{adiY}$-adiY-$P_{adiC})$ adiC mutation (hereafter adiAC). The DNA regions flanking adiY were amplified by PCR from Ty2 using primers Adi-10 and -11 for the upstream region and primers Adi-12 and -13 for the downstream region. The two DNA segments were joined by overlap PCR and re-amplification with Adi-10 and -13. The final PCR product was ligated into pYA4278 at the AhdI sites to produce the suicide vector pYA5072. The suicide vector was introduced into χ11564 and χ11548 by conjugation to produce χ11568 (ΔaroD $P_{rhaBAD}$ adiAC) and χ11636 (ΔaroD adiAC), respectively. The presence of the adiAC operon was confirmed by PCR using Adi-14 and -15. Both strains harbor a 1078-bp deletion that spans the transcription terminator following adiA, adiY and the promoter of adiC. The adiA and adiC genes are separated by a 119-bp intergenic sequence expected to decrease expression of adiC from the promoter upstream of adiA (FIG. 1).

Growth Conditions and Culture Media. Experiments testing the regulation of arabinose- and rhamnose-controlled genes were conducted in the carbohydrate-free medium purple broth (BD Biosciences, Franklin Lakes, N.J., USA). For acid resistance experiments, strains were propagated in tryptic soy broth (TSB) (BD Biosciences) with 0.4% glucose, or in minimal E medium, pH 7.0 with 0.4% glucose (EG medium) (37). For our experiments, 22 µg/ml L-cysteine, 20 µg/ml L-tryptophan and 0.1% casamino acids were added to EG medium in order to supplement the growth of all strains (EGA medium). For strains with the ΔaroD mutation, 20 µg/ml L-tryptophan, 2 µg/ml p-aminobenzoic acid and 2.5 µg/ml 2,3-dihydroxybenzoate were added to all media. EGA medium was additionally supplemented with 50 µg/ml L-phenylalanine and 20 µg/ml L-tyrosine. Rhamnose was added to 0.1% or to 0.4% in the case of strain χ11623, as indicated. Strains containing the $\Delta P_{fur}$::TT araC $P_{araBAD}$ fur mutation were supplied with 0.2% arabinose unless otherwise indicated. All chemicals were purchased from Sigma-Aldrich (St. Louis, Mo., USA) or Thermo Fisher Scientific (Pittsburgh, Pa., USA) unless otherwise indicated.

Measurement of adiA Expression by Semi-Quantitative PCR. Strains were grown in purple broth with varying concentrations of rhamnose or arabinose to an optical density at 600 nm ($OD_{600}$) of 0.6. Total cellular RNA was isolated using the RNeasy Mini Kit (QIAGEN) and was treated with RNase-free DNase (QIAGEN). cDNA was generated via reverse transcription-PCR (RT-PCR) using 1 µg of cellular RNA with the TaqMan Reverse Transcriptase kit (Life Technologies, Grand Island, N.Y.) under the following conditions: 10 minutes at 25° C. for optimal random hexamer primer binding, then 45 minutes at 48° C. for extension followed by 5 minutes at 95° C. to heat inactivate the transcriptase. Semi-quantitative PCR of the adiA and gapA transcripts was performed using the GoTaq DNA Polymerase system (Promega) using primers SQ-1 and SQ-2 for gapA and SQ-3 and SQ-4 for adiA under the following conditions: 2.5 minutes at 95° C. for template denaturation, followed by 28 cycles of 40 s at 95° C., 30 s at 48° C. for primer annealing and 1 minute at 72° C. for primer extension. The semi-quantitative PCR primer sequences are listed in Table 2 (SQ1-SQ4). PCR products were electrophoresed on a 2% agarose gel in the presence of ethidium bromide and visualized with the ChemiDoc XRS System (Bio-Rad Laboratories, Hercules, Calif., USA). Images were analyzed in Adobe PhotoshopCS4 (Adobe Systems Incorporated, San Jose, Calif., USA) in order to establish histogram values for the fluorescence signal intensity of the PCR products. Signal intensity values for adiA were normalized to the value obtained with the single gene expression control gapA for each culture.

Preparation of Antiserum Against Arginine Decarboxylase Protein. E. coli BL21 (DE3) harboring pYA5085 was used for the synthesis of His-tagged AdiA protein. Cells were grown in LB at 37° C. to mid-log phase (an optical density value at 600 nm [$OD_{600}$] of 0.6). The growth medium was supplemented with 0.2 g/L pyridoxine to augment protein folding and enzyme activity (38). Protein synthesis was induced with 1 mM IPTG (isopropyl β-D-1-thiogalactopyranoside) (Amresco, Solon, Ohio, USA) for 4 hours at 37° C. Cells were collected by centrifugation and disrupted using lysozyme (3 mg/g cells) and deoxycholic acid (120 mg/g cells) (39). His-tagged AdiA protein from the soluble fraction was purified over TALON™ metal affinity resin (BD Biosciences) in accordance with the manufacturer's instructions except that 10% ethanol was added to the elution buffer. Purified protein was stored in 20 mM HEPES, 50 mM NaCl, pH 8.0 (30).

One juvenile New Zealand white rabbit (Charles River Laboratories, Wilmington, Mass., USA) was immunized with 200 µg of AdiA emulsified in Freund's complete adjuvant, and boosted with an additional 200 µg of AdiA emulsified in Freund's incomplete adjuvant 4 weeks and 8 weeks after the initial injection. Serum was collected 3 weeks following the final immunization.

Western Blot Procedure. Strains were grown overnight at 37° C. in purple broth containing various concentrations of rhamnose or arabinose. The amount of total cellular protein in each sample was normalized by absorbance at 280 nm using the NanoDrop ND-1000 (Thermo Scientific, Wilmington, Del., USA). Equal amounts of cellular protein (100 µg for AdiA; 150 µg for Fur) were mixed with 2×SDS-PAGE buffer, boiled, and electrophoresed on a 10% acrylamide gel (40). Separated proteins were transferred to a PVDF membrane (Bio-Rad) using Towbin's wet transfer method (41), blocked in 5% skim milk, then probed with rabbit antiserum (final dilution 1:10,000) for the presence of AdiA or Fur (36). Bound primary antibody was detected by the addition of goat anti-rabbit IgG conjugated to alkaline phosphatase (Sigma-Aldrich). Blots were developed with NBT/BCIP (Amresco) and photographed using the ChemiDocXRS System.

Arginine Decarboxylase Assays. Arginine decarboxylase enzyme activity was measured using a modified version of the rapid glutamate decarboxylase assay previously described (42). Strains were grown overnight (18 h) to stationary phase in purple broth, washed once in phosphate buffered saline (PBS) (39) and normalized to an $OD_{600}$ value of 0.7. Five ml of normalized cells were pelleted, resuspended in 2.5 ml arginine decarboxylase assay medium [1 g L-arginine, 0.05 g bromocresol green, 90 g NaCl, and 3 ml Triton X-100 per liter of distilled water (adjusted to pH 3.4)] and vortexed for 30 s. Assay tubes were incubated at 37° C. for 5-30 minutes, scored and photographed.

Acid Resistance Assays. Acid resistance was determined essentially as described previously (43, 44) with the following modifications. Strains were grown overnight to stationary phase in minimal EGA medium at pH 7.0 (37) or in TSB with 0.4% glucose. Cultures were normalized to the same $OD_{600}$, then pelleted and washed once in EGA medium, pH 7.0 containing no growth supplements. Cells were pelleted a second time and resuspended at a density of $1 \times 10^9$ CFU/ml in EGA medium containing 1 mM L-arginine at pH 3.0, 2.5 or 2.0. Low pH challenge was conducted at 37° C. and samples were collected immediately after resuspension (t=0) and hourly for 4 h. Samples were serially diluted and plated onto LB agar to assess viability during challenge.

Statistical Analyses. All statistical analyses were performed using GraphPad Prism version 5.04 for Windows (GraphPad Software, San Diego, Calif. USA, www.graphpad.com). Survival curves for 4-hour acid resistance assays were compared using two-way repeated measures (mixed model) ANOVA with Bonferroni's post-test. Data from 1 h acid resistance challenges were compared using the paired t test.

Results

Example 1

Comparison of adiA Regulation from Arabinose- and Rhamnose-Regulated Promoters Genes encoding the arginine decarboxylase system are normally expressed in *Salmonella* only under anaerobic conditions (3, 33). To allow expression during aerobic growth, we constructed two conditional adiA mutants that resulted in strains in which adiA expression was regulated by either the araBAD or rhaBAD promoter. For safety, the sugar-regulated adiA constructions were introduced into *S. Typhi* strain χ11548, which carries an attenuating ΔaroD mutation (17, 45). Thus, in strains χ11552 (ΔaroD $P_{araBAD}$ adiA) and χ11564 (ΔaroD $P_{rhaBAD}$ adiA), adiA expression should be responsive to the levels of exogenous arabinose or rhamnose, respectively. In the absence of the regulating sugar, both strains expressed low levels of adiA transcript consistent with background levels observed in Ty2 cultured under non-inducing conditions for adiA (FIG. 2A). Both strains increased production of the adiA mRNA transcript when 0.1% ($10^{-1}$%) of the appropriate sugar was added. However, at lower sugar concentrations, the two strains behaved differently. Strain χ11552 ($P_{araBAD}$ adiA) continued to express elevated amounts of adiA mRNA at arabinose concentrations as low as 0.001% ($10^{-3}$%). Only when the arabinose concentration fell below 0.001% ($10^{-3}$%) did the amount of adiA transcript return to background levels. In contrast, strain χ11564 ($P_{rhaBAD}$ adiA) expressed adiA transcript only in the presence of 0.1% ($10^{-1}$%) rhamnose and produced background levels of adiA mRNA at lower rhamnose concentrations.

AdiA protein synthesis and enzyme activity levels presented a pattern similar to the mRNA. χ11552 ($P_{araBAD}$ adiA) synthesized AdiA over a wide range of arabinose concentrations ($10^{-1}$-$10^{-4}$% arabinose), while in χ11564 ($P_{rhaBAD}$ adiA) AdiA was detected over a narrower range of rhamnose concentrations ($10^{-1}$-$10^{-2}$% rhamnose) (FIG. 2B). While the highest amounts of AdiA in both strains were observed at the arabinose and rhamnose concentrations that increased levels of adiA transcript, small amounts of AdiA were also detected at sugar concentrations that did not produce a measurable increase in the amount of adiA transcript present ($10^{-4}$% arabinose for χ11552 and $10^{-2}$% rhamnose for χ11564), which could reflect differences in the sensitivity of the two assays or to differences in the stability of the adiA mRNA transcript and AdiA protein.

AdiA activity was evaluated by decarboxylase assay, in which active enzyme raises the assay medium pH above 5.0, resulting in a color change from yellow-green (negative) to blue (positive). Arginine decarboxylase activity (FIG. 2C) correlated with detection of AdiA on the western blot (FIG. 2B) and could be detected in χ11552 ($P_{araBAD}$ adiA) cultures grown in the presence of arabinose concentrations as low as 10-3%. An intermediate reaction suggestive of low levels of enzyme activity was observed at $10^{-4}$% arabinose. In contrast, arginine decarboxylase activity was observed in χ11564 ($P_{rhaBAD}$ adiA) only at rhamnose concentrations greater than $10^{-2}$%. Because the rhamnose-regulated $P_{rhaBAD}$ promoter provided tighter control over AdiA synthesis and activity than the arabinose-regulated $P_{araBAD}$ promoter, we selected the $\Delta P_{adiA}$::TT rhaSR $P_{rhaBAD}$ adiA mutation for further studies.

Example 2

Figure 3:
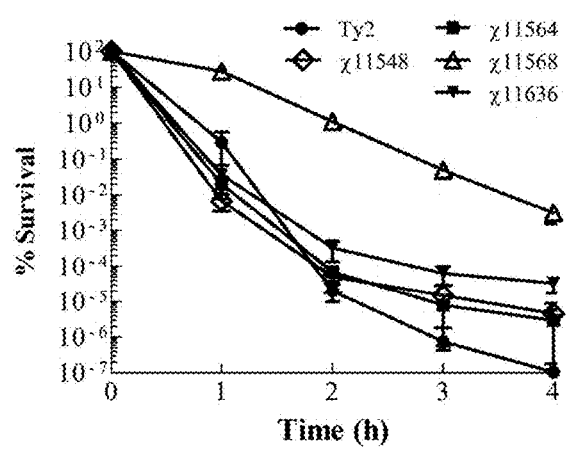
FIG. 3. Co-regulation of adiA and adiC by rhamnose is required for survival during pH 3 challenge. χ11564 (ΔaroD $P_{rhaBAD}$ adiA), χ11568 (ΔaroD $P_{rhaBAD}$ adiAC) and χ11636 (ΔaroD adiAC) were grown to stationary phase in EG medium in the presence of 0.1% rhamnose, then challenged with pH 3.0 EG medium containing 1 mM arginine. Survival was monitored by plating on LB agar containing all necessary supplements. Data shown are the mean and SEM of three independent assays.

Co-Regulation of adiA and adiC is Necessary for Survival During pH 3.0 Challenge Our goal in introducing the $P_{rhaBAD}$ adiA construct into *S. Typhi* was to provide arginine-dependent acid resistance when cells were grown under conditions when this system is not normally induced (non-inducing conditions). To test this, we performed low pH challenges on cells grown aerobically in minimal EGA medium. However, while χ11564 (ΔaroD $P_{rhaBAD}$ adiA) exhibited rhamnose-regulatable arginine decarboxylase activity under these conditions (data not shown), the survival profile of χ11564 (ΔaroD $P_{rhaBAD}$ adiA) at pH 3.0 did not differ from that of Ty2 or its parent strain χ11548 (ΔaroD) (FIG. 3). This is likely due to the fact that arginine-dependent acid resistance requires substrate::product exchange by AdiC in addition to proton consumption by AdiA (29). Based on this, we reasoned that the $P_{rhaBAD}$ promoter in strain χ11564 (ΔaroD $P_{rhaBAD}$ adiA) does not drive adiC expression due to the presence of a transcriptional terminator downstream of adiA and the intervening adiY gene. Thus, it is likely that adiC expression remains under the control of its native promoter and is not induced by rhamnose (FIG. 1). To co-regulate expression of both adiA and adiC, the intergenic region between the two genes, including the regulatory gene adiY and the adiC promoter, was deleted, resulting in the fusion of adiA and adiC into a single operon under the control of the native adiA promoter, resulting in strain χ11636 (adiAC) (FIG. 1). The sensitivity of χ11636 to pH 3.0 challenge was not significantly different from Ty2 and χ11548 (ΔaroD) (p=0.327) (FIG. 3). The adiAC operon fusion was then placed under transcriptional control of $P_{rhaBAD}$ adiA resulting in strain χ11568 (ΔaroD $P_{rhaBAD}$ adiAC). When grown with 0.1% rhamnose, strain χ11568 was highly resistant to pH 3.0 challenge (FIG. 3), displaying a 1,000 to 10,000-fold increase over Ty2 in the number of viable cells present at all time points during challenge (p<0.0001).

Example 3

Survival of Strain χ11568 During pH 3 Challenge is Rhamnose- and Arginine-Dependent A number of acid resistance and acid tolerance mechanisms have been described in stationary phase *Salmonella*. To confirm that the acid-resistant phenotype of χ11568 (ΔaroD $P_{rhaBAD}$ adiAC) was attributable to the rhamnose-regulated arginine decarboxylase system the strain was tested for survival at pH 3.0 in the absence of rhamnose and arginine. When cultured in minimal EGA medium without rhamnose, χ11568 (ΔaroD $P_{rhaBAD}$ adiAC) displayed a survival profile indistinguishable from the wild-type Ty2 and parent strain χ11548 (ΔaroD) during pH 3.0 challenge (FIG. 4A). Adding rhamnose to the EGA culture medium restored the acid resistance of χ11568 (ΔaroD $P_{rhaBAD}$ adiAC), resulting in a 1,000- to 10,000-fold higher survival rate when rhamnose was provided (p=0.001).

The acid resistance of χ11568 (ΔaroD $P_{rhaBAD}$ adiAC) also depended on the presence of arginine in the challenge medium (FIG. 4B). The percentage of viable χ11568 (ΔaroD $P_{rhaBAD}$ adiAC) cells during challenge rapidly declined over 4 hours in the absence of arginine, with few survivors detected after the first two hours. However, cells that were challenged in the presence of 1 mM arginine showed a marked increase in survival (p=0.003). Interestingly, removing arginine from the challenge medium also impaired survival of Ty2 (p=0.022), even though arginine decarboxylase activity was not detected under these culture conditions (data not shown).

Figure 5:
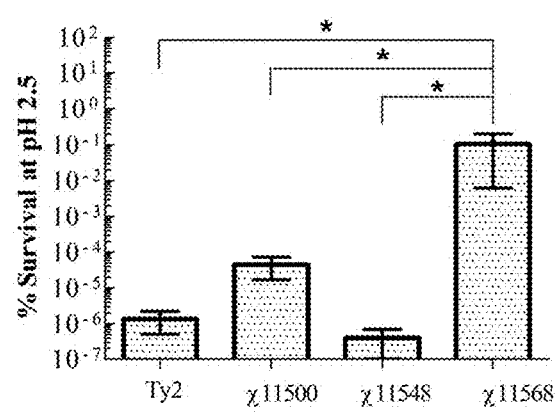
FIG. 5. Acid resistance of an ΔaroD mutant containing rhamnose-regulated arginine decarboxylase at pH 2.5. Ty2, χ11500 (ΔadiA-adiC), χ11548 (ΔaroD) and χ11568 (ΔaroD $P_{rhaBAD}$ adiAC) were grown to stationary phase in EG medium containing 0.1% rhamnose, then challenged with EG medium containing 1 mM arginine at pH 2.5 for 1 hour. Survival in all assays was monitored by plating on LB agar containing all necessary supplements. Data shown are the mean and SEM of three independent assays. Pairs of data marked with an asterisk (*) are significantly different ($p<0.05$).
Figure 8:
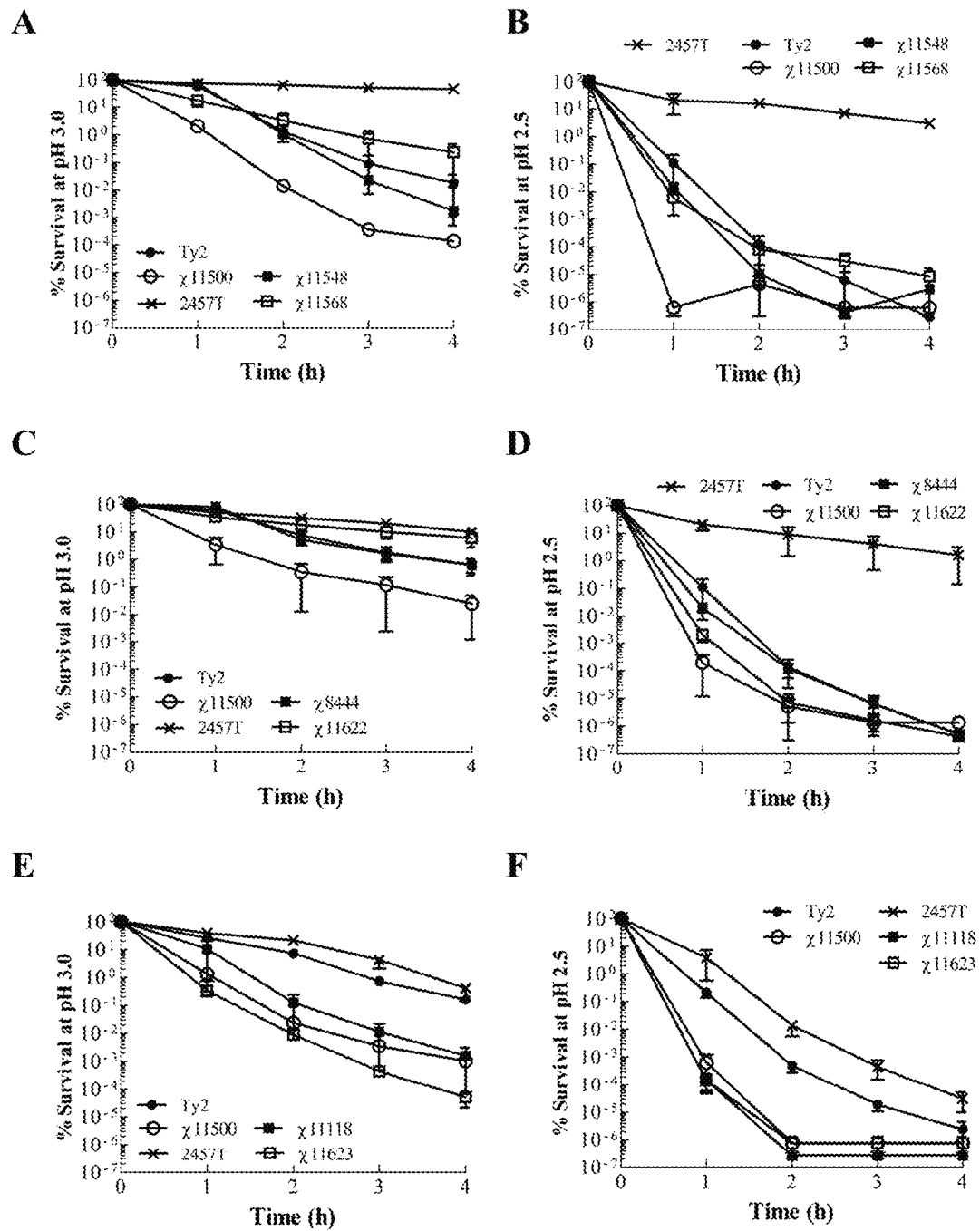

The rhamnose-regulated arginine decarboxylase system provided a substantial benefit to S. Typhi survival during pH 2.5 challenge (FIG. 5). After 1 hour at pH 2.5, χ11568 (ΔaroD $P_{rhaBAD}$ adiAC) survived not only significantly better than its ΔaroD parent (χ11548) (ΔaroD) (p=0.010), but also significantly better than the wild type (p=0.010) and arginine decarboxylase knockout χ11500 (p=0.035). Of the $10^9$ CFU that were challenged, over $10^8$ CFU of χ11568 (ΔaroD $P_{rhaBAD}$ adiAC) remained viable after one hour. Despite this high level of survival and although previous reports indicated that the arginine decarboxylase system could protect *Salmonella Typhimurium* for greater than two hours at pH 2.5 (3), we did not detect any *S. Typhi* survivors after the first hour of challenge (data not shown).

Example 4

Rescue of ΔphoPQ and $\Delta P_{fur}$::TT araC $P_{araBAD}$ Fur Mutants at pH 3 and 2.5

Because the rhamnose-regulated arginine decarboxylase system conferred such a high degree of acid resistance on χ11568 (ΔaroD $P_{rhaBAD}$ adiAC) when grown aerobically in minimal media (non-inducing conditions) (FIG. 3), we tested the ability of this system to rescue two acid sensitive strains of *S. Typhi*—a phoPQ mutant (χ8444) and a conditional fur mutant (χ11118). These mutations result in well-characterized acid sensitivities. Introducing the $P_{rhaBAD}$ adiAC construct into strains χ8444 (ΔphoPQ) and χ11118 ($P_{araBAD}$ fur) resulted in strains χ11622 and χ11623, respectively, that exhibited rhamnose-dependent arginine decarboxylase synthesis as described for χ11568 (ΔaroD $P_{rhaBAD}$ adiAC) (FIG. 2C and data not shown).

To evaluate the ability of the rhamnose-regulated arginine decarboxylase system to rescue ΔphoPQ, strain χ11622 (ΔphoPQ $P_{rhaBAD}$ adiAC) was grown in minimal EGA medium to stationary phase at pH 7.0 in the presence of 0.1% rhamnose and then were challenged at either pH 3.0 or pH 2.5. Under these growth conditions, the ΔphoPQ mutant χ8444 displayed a similar survival profile as the wild-type Ty2 (p=0.996) (FIG. 6A). In contrast, the survival of strain χ11622 (ΔphoPQ $P_{rhaBAD}$ adiAC) was significantly greater than its parent strain χ8444 (ΔphoPQ) or the wild-type Ty2 (p=0.034). Further, strain χ11622 (ΔphoPQ $P_{rhaBAD}$ adiAC) was significantly more resistant to a 1 h challenge at pH 2.5 than any of the other *S. Typhi* strains (p=0.009 for χ8444; 0.010 for Ty2 and 0.0232 for χ11500—ΔadiA-adiC) (FIG. 6B).

We next examined the impact of the arginine decarboxylase system on a fur mutant (χ11623 ($P_{araBAD}$ fur $P_{rhaBAD}$ adiAC)). For this analysis, we utilized the conditional fur mutant χ11118 ($P_{araBAD}$ fur) in which fur expression can be induced by addition of arabinose to the culture medium (36). However, western blot analysis indicated that, while Fur synthesis was induced by arabinose, the level of Fur produced in strain χ11118 ($P_{araBAD}$ fur) was much less than the amount produced by Ty2 (FIG. 7A). Consistent with the low level of arabinose-induced Fur production, the survival of pH 3.0-challenged cells grown in the presence of 0.2% arabinose did not differ from that of cells grown in the absence of arabinose (p=0.934) (FIG. 7B). Since χ11118 ($P_{araBAD}$ fur) had the phenotype of a fur knockout in the acid resistance assay irrespective of the arabinose concentration, we decided to work with it and the rhamnose-regulated arginine decarboxylase daughter strain (χ11623-$P_{araBAD}$ fur $P_{rhaBAD}$ adiAC) only in the absence of arabinose. We observed no difference in survival at pH 3.0 between the wild-type Ty2, the arginine decarboxylase knockout χ11500 (ΔadiA-adiC) and χ11118 ($P_{araBAD}$ fur) in our assay (p=0.392) (FIG. 7C). Strain χ11623 ($P_{araBAD}$ fur $P_{rhaBAD}$ adiAC) displayed greater survival than its parent χ11118 ($P_{araBAD}$ fur) for the first hour of challenge at pH 3.0 (p=0.010) indicating that the arginine decarboxylase system could rescue this fur mutant to some degree. However, there was no difference between χ11623 ($P_{araBAD}$ fur $P_{rhaBAD}$ adiAC) and χ11118 ($P_{araBAD}$ fur) for the later time points (p=0.337). A similar trend was observed at pH 2.5 (FIG. 7D). χ11623 ($P_{araBAD}$ fur $P_{rhaBAD}$ adiAC) survived significantly better after 1 hour at pH 2.5 than its acid-sensitive parent χ11118 ($P_{araBAD}$ fur) (p=0.013), but it was not significantly different from the wild-type Ty2 (p=0.242) or the arginine decarboxylase mutant χ11500 (ΔadiA-adiC) (p=0.122).

Example 5

Rhamnose-Dependent Acid Resistance is Equivalent to Acid Resistance in Cells Grown Under Decarboxylase-Inducing Conditions We next compared the level of acid resistance afforded by the rhamnose-regulated system to the acid resistance provided by the native system. Strains were grown anaerobically in unbuffered rich medium where the pH was allowed to fall below pH 5.0 during growth (native inducing conditions). Strains were supplied with 0.1% (or 0.4%, see below) rhamnose during growth. Cells were then challenged in EGA medium with 1 mM arginine at pH 3.0 or 2.5. The arginine decarboxylase deletion mutant χ11500 (ΔadiA-adiC) rapidly succumbed to challenge at both pH 3.0 and 2.5 (FIG. 8A, 8B). Ty2 and χ11548 (ΔaroD) displayed a high degree of acid resistance at pH 3.0 (greater than $10^4$ CFU/ml were viable after 4 hours), but succumbed to pH 2.5 after 2 hours. In contrast, the highly acid resistant *Shigella flexneri* strain 2457T exhibited >70% viability for 4 hours at pH 3.0 and viability only decreased by one log after 4 hours at pH 2.5. Strain χ11568 (ΔaroD $P_{rhaBAD}$ adiAC) was not able to match the acid resistance profile of *Shigella*, although it displayed a survival profile equivalent to the *S. Typhi* Ty2 and χ11548 (ΔaroD) grown under these conditions (p=0.210). These results indicate that the rhamnose-regulated system provides a level of acid resistance equivalent to the acid resistance afforded by the native system.

Under the native adiA-inducing conditions, both phoPQ mutants, χ8444 (ΔphoPQ) and χ11622 (ΔphoPQ $P_{rhaBAD}$ adiAC), behaved similarly to Ty2 during pH 3.0 challenge (p=0.498) (FIG. 8C). This was in contrast to the arginine decarboxylase deletion strain χ11500 (ΔadiA-adiC), which survived significantly less well than the phoPQ strains at pH 3.0 (p=0.018). No difference was observed in survival at pH 3.0 between χ8444 (ΔphoPQ) (which utilized the native arginine decarboxylase system) and χ11622 (ΔphoPQ $P_{rhaBAD}$ adiAC) (which utilized the rhamnose-regulated system) (p=0.628). A similar pattern was observed at pH 2.5 (FIG. 8D). No difference was observed between the native arginine decarboxylase system in χ8444 (ΔphoPQ) and the rhamnose-regulated system in χ11622 (ΔphoPQ $P_{rhaBAD}$ adiAC) (p=0.702).

Unlike χ11568 (ΔaroD $P_{rhaBAD}$ adiAC) and χ11622 (ΔphoPQ $P_{rhaBAD}$ adiAC), the conditional fur mutant χ11623 (P$_{araBAD}$ fur P$_{rhaBAD}$ adiAC) did not produce detectable arginine decarboxylase activity in the presence of 0.1% rhamnose when cultured in anaerobic rich medium. Arginine decarboxylase activity was detectable only when the rhamnose concentration was increased to 0.4% (data not shown). Therefore, the concentration of rhamnose present in this assay was raised to 0.4% for χ11623 (P$_{araBAD}$ fur P$_{rhaBAD}$ adiAC). In contrast to the phoPQ mutants, the fur mutants χ11118 (P$_{araBAD}$ fur) and χ11623 (P$_{araBAD}$ fur P$_{rhaBAD}$ adiAC) were significantly more sensitive to pH 3.0 than the wild-type Ty2 (FIG. 8E). χ11118 (P$_{araBAD}$ fur) and χ11623 (P$_{araBAD}$ fur P$_{rhaBAD}$ adiAC) displayed a survival profile more similar to that of χ11500 (ΔadiA-adiC) (p=0.392) than Ty2 (p=0.0006). However, there was no observable difference in survival between χ11118 (P$_{araBAD}$ fur) and χ11623 (P$_{araBAD}$ fur P$_{rhaBAD}$ adiAC) at either pH 3.0 (p=0.332) or pH2.5 (p=0.882) (FIG. 8F). These results indicate that for both the ΔphoPQ and P$_{araBAD}$ fur mutants, the rhamnose-regulated arginine decarboxylase system and the native system provided equivalent levels of acid resistance.

Discussion of Examples 1 to 5

Figure 2:
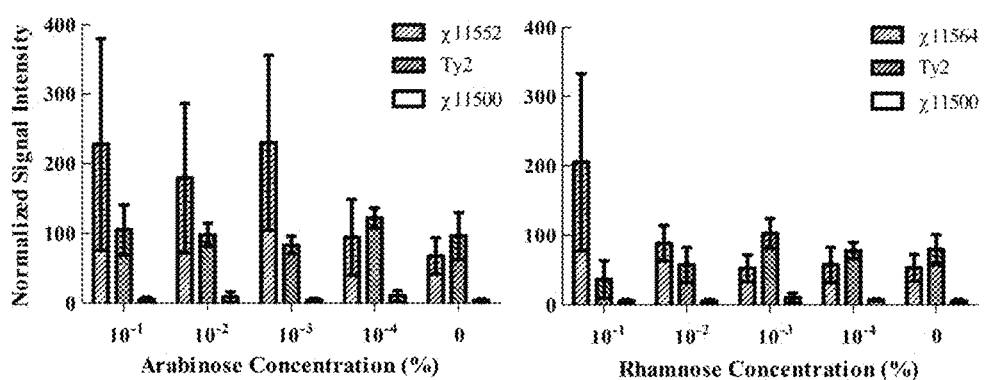
FIG. 2. Regulation of adiA by the araC $P_{araBAD}$ and rhaSR $P_{rhaBAD}$ promoters. χ11552 (ΔaroD $P_{araBAD}$ adiA) and χ11564 (ΔaroD $P_{rhaBAD}$ adiA) were cultured in the presence of varying concentrations of arabinose or rhamnose (ranging from $10^{-1}$-$10^{-5}$%), normalized and (A) assayed by semi-quantitative PCR for the level of adiA transcript, (B) probed for the presence of AdiA by western blot or (C) tested for arginine decarboxylase activity via colorimetric assay. mRNA data are plotted as the mean and SEM of three independent experiments. Western blot and enzyme assay data are representative of three independent assays. In the colorimetric arginine decarboxylase assay, a dark blue color is indicative of the presence of AdiA.
Figure 2:
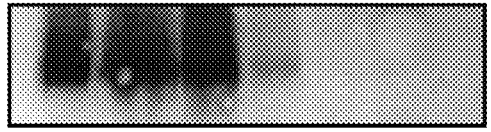
Figure 2:
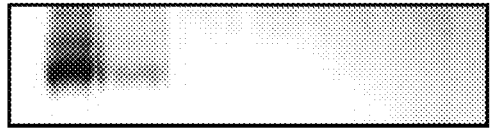
Figure 2:
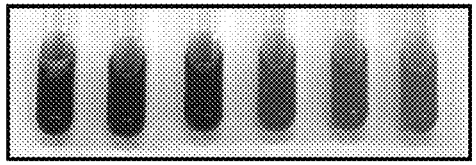
Figure 2:
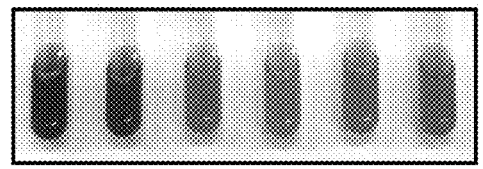
Figure 6:
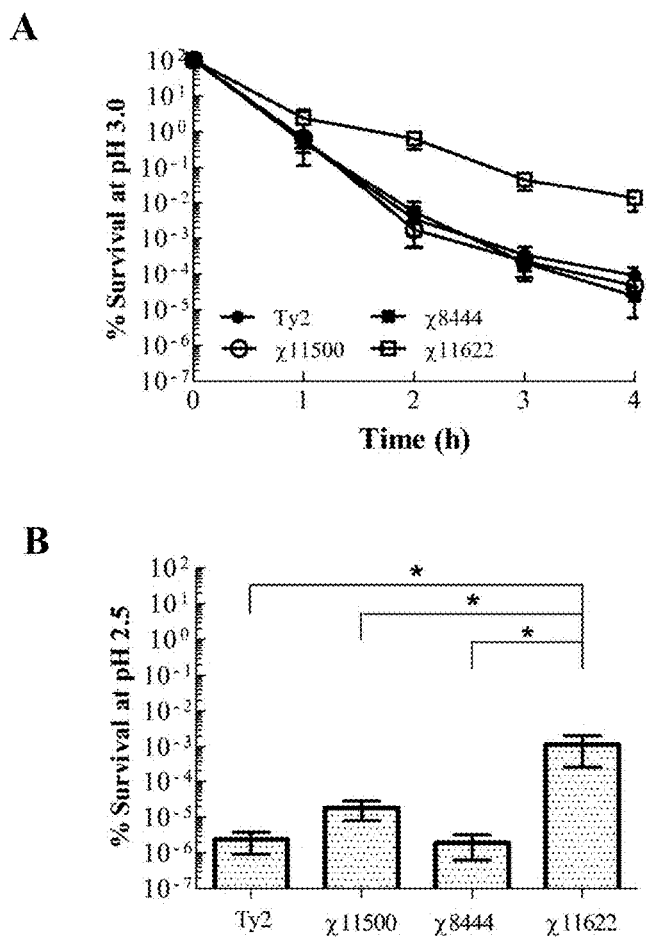
FIG. 6. Acid resistance of a ΔphoPQ mutant containing rhamnose-regulated arginine decarboxylase. Ty2, χ11500 (ΔadiA-adiC), χ8444 (ΔphoPQ) and χ11622 (ΔphoPQ $P_{rhaBAD}$ adiAC) were grown to stationary phase in EG medium containing 0.1% rhamnose, then challenged with EG medium containing 1 mM arginine at (A) pH 3.0 for 4 hours or (B) pH 2.5 for 1 hour. Survival in all assays was monitored by plating on LB agar containing all necessary supplements. Data shown are the mean and SEM of three independent assays. Pairs of data marked with an asterisk (*) are significantly different ($p<0.05$).
Figure 7:
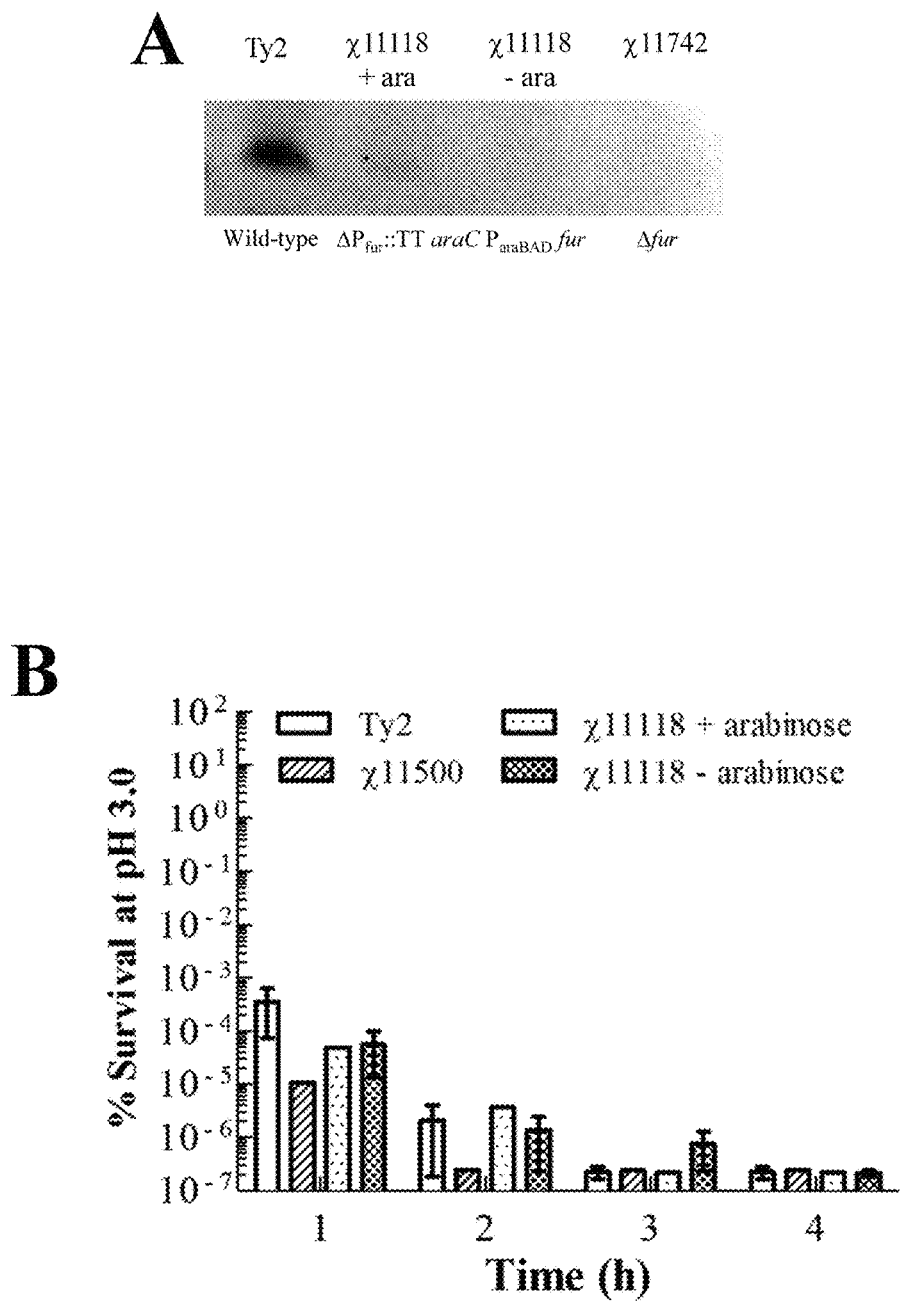
FIG. 7. Acid resistance of a Δ$P_{fur}$::TT araC $P_{araBAD}$ fur mutant containing rhamnose-regulated arginine decarboxylase. (A) Strains were grown overnight in purple broth±0.2% arabinose, then probed for the presence of Fur by western blot. (B) χ11118 was grown to stationary phase in EG medium±0.2% arabinose, then challenged with EG medium containing 1 mM arginine at pH 3.0 for 4 hours. Arginine decarboxylase rescue was performed by growing strains in EG medium to stationary phase in the absence of arabinose and presence of 0.1% rhamnose and challenging with EG medium containing 1 mM arginine at (C) pH 3.0 for 4 hours or (D) pH 2.5 for 1 hour. Survival in all assays was monitored by plating on LB agar containing all necessary supplements. Data shown are the mean and SEM of three independent assays. Pairs of data marked with an asterisk (*) are significantly different ($p<0.05$). χ11500=ΔadiA-adiC; χ11118=$P_{araBAD}$ fur; χ11623=$P_{araBAD}$ fur $P_{rhaBAD}$ adiAC; χ11742=Δfur FIG. 8. Comparison of acid resistance provided by native and rhamnose-regulated arginine decarboxylase. Strains containing (A, B) ΔaroD (C, D) ΔphoPQ or (E, F) Δ$P_{fur}$::TT araC $P_{araBAD}$ fur attenuating mutations were grown overnight in TSB medium with 0.4% glucose and 0.1% rhamnose under anaerobic conditions. For χ11623, 0.4% rhamnose was supplied. Cells were challenged with EG medium containing 1 mM arginine, pH 3.0 (A, C, E) or pH 2.5 (B, D, F). Survival in all assays was monitored by plating on LB agar containing all necessary supplements. Data shown are the mean and SEM of three independent assays. 11500=ΔadiA-adiC; 11548=ΔaroD; 11568=ΔaroD $P_{rhaBAD}$ adiAC; 8444=ΔphoPQ; 11622=ΔphoPQ $P_{rhaBAD}$ adiAC; 11118=$P_{araBAD}$ fur; 11623=$P_{araBAD}$ fur $P_{rhaBAD}$ adiAC.
Figure 7:
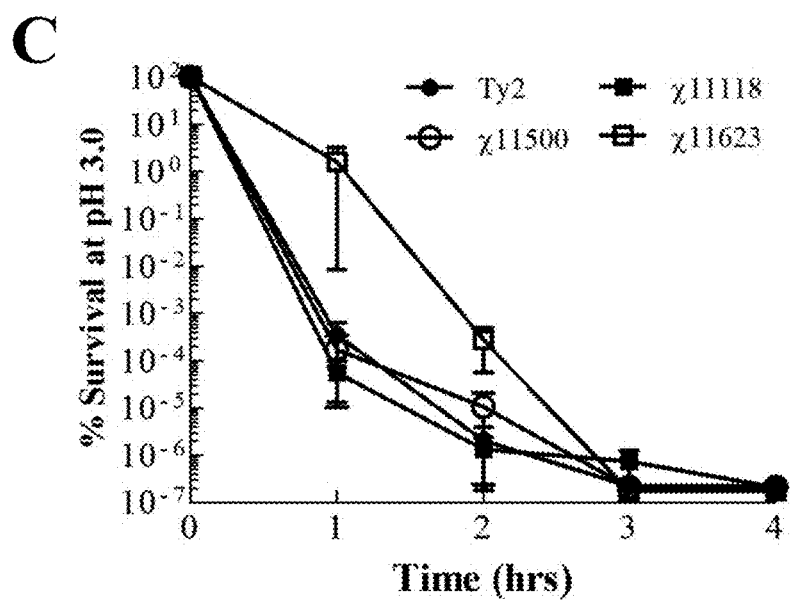
Figure 7:
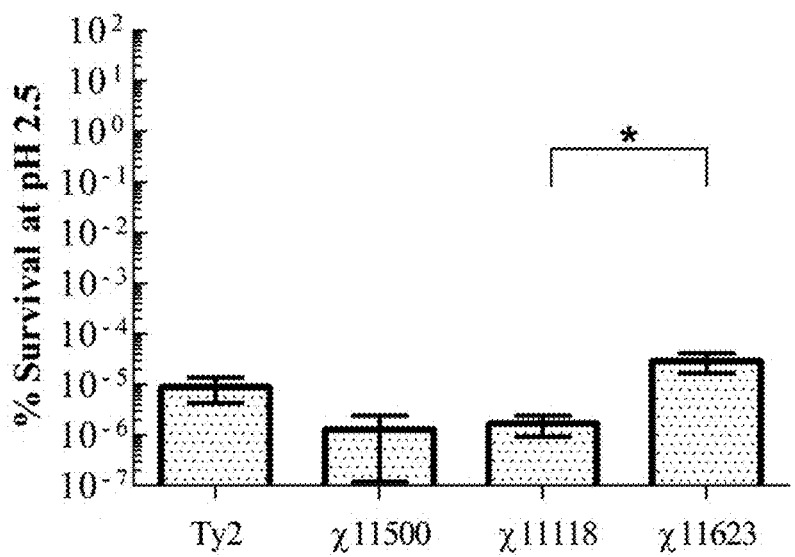

In this work, we constructed an acid resistance system whose expression and activity responded to the presence of a single sugar, either arabinose or rhamnose. Both adiA and adiC expression were required for acid resistance (FIG. 3) and the rhamnose-regulated P$_{rhaBAD}$ promoter provided tighter control over adiA expression than the arabinose-regulated P$_{araBAD}$ promoter (FIG. 2). The level of acid resistance provided by P$_{rhaBAD}$ adiAC grown with rhamnose under decarboxylase-inducing conditions was equivalent to the level of acid resistance observed with the native arginine decarboxylase system grown under the same conditions. However, the rhamnose-regulated adiAC system was regulatable in cells otherwise unprepared for low pH challenge, thus our rhamnose-regulated system significantly improved the survival of acid-unadapted aroD, phoPQ and fur mutants at pH 3 and 2.5 (FIGS. 3, 6 and 7).

Comparison of the arabinose-regulated P$_{araBAD}$ and rhamnose-regulated P$_{rhaBAD}$ promoters indicated that P$_{rhaBAD}$ was less sensitive to its regulatory sugar than P$_{araBAD}$. At high concentrations of arabinose or rhamnose (0.1%), both promoters were active. The two promoters drove production of essentially equivalent amounts of adiA transcript at this concentration, consistent with previous results (46). As the amount of regulatory sugar present in the culture was decreased, the activity of the two promoters decreased differentially. While background levels of transcription were detected from P$_{rhaBAD}$ at rhamnose concentrations below 0.01% ($10^{-2}$%), P$_{araBAD}$ continued to function until the arabinose concentration fell below 0.0001% ($10^{-4}$%). Some of this difference may be attributable to the "leakiness" of the P$_{araBAD}$ promoter (47, 48). However, we used a modified sequence for P$_{araBAD}$, which exhibits tightly controlled arabinose-dependent transcription (49). Since rhamnose is transported into Salmonella more efficiently than arabinose, differences in sugar uptake are unlikely to be the cause of this discrepancy (50, 51). It is possible that rhamnose is converted to a non-inducing state following transport, because while neither arabinose nor rhamnose can be fermented by S. Typhi (52), the rhaB and rhaA genes are intact and their gene products may be able to act on the transported rhamnose. Another explanation is the previously observed slow rate of transcription from the P$_{rhaBAD}$ promoter (53) resulting from the cascade of regulation by RhaR and RhaS on P$_{rhaBAD}$ (51, 54) The reduced sensitivity of the P$_{rhaBAD}$ promoter makes it an ideal choice to regulate the arginine decarboxylase system since it allows tight control of gene expression even in media containing trace amounts of rhamnose, such as LB and TSB.

Figure 4:
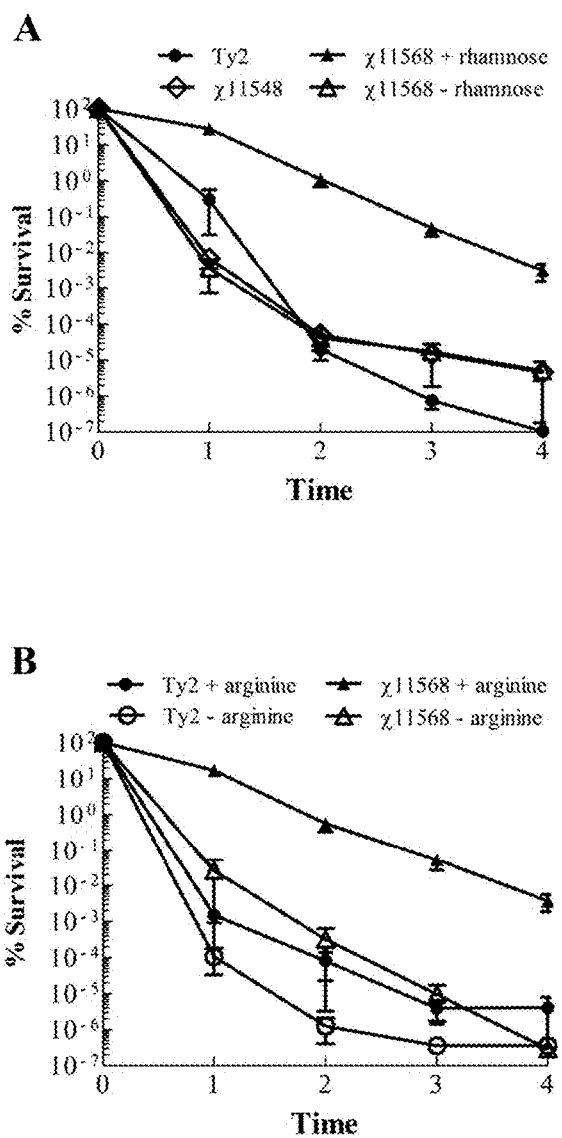
FIG. 4. Acid resistance depends on the presence of rhamnose and arginine. Ty2, χ11548 (ΔaroD) and χ11568 (ΔaroD $P_{rhaBAD}$ adiAC) were grown to stationary phase in EG medium, then challenged with EG medium, pH 3.0. (A) Strains cultured in the presence or absence of 0.1% rhamnose. (B) Strains challenged in the presence or absence of 1 mM arginine. Survival in all assays was monitored by plating on LB agar containing all necessary supplements. Data shown are the mean and SEM of three independent assays.

Rhamnose-dependent acid resistance in S. Typhi depended on three things—the presence of rhamnose in the culture medium, the presence of arginine in the challenge medium, and the fusion of adiA and adiC into an operon under the control of P$_{rhaBAD}$. The absence of any of these components resulted in rapid cell death at pH 3.0 (FIGS. 3 and 4). The requirement for co-regulation of adiA and adiC is consistent with the known mechanism of the arginine decarboxylase system. Although AdiA is the enzyme that consumes protons and is responsible for raising the intracellular pH during low pH challenge (55), AdiC is required to import a continuous supply of arginine substrate from the periplasm (29). Deletions of either adiA or adiC abolish arginine-dependent acid resistance (3). The arginine requirement for survival at low pH confirms that the acid resistance we observed was due to the Salmonella arginine decarboxylase system and not to the stationary phase acid tolerance response or the oxidative acid resistance response (AR1), as neither of these systems requires arginine (2, 43). Interestingly, even though cells were cultured in aerobic minimal medium to prevent induction of the native arginine decarboxylase system in wild-type S. Typhi strain Ty2 (3), we observed an arginine-dependent increase in resistance to pH 3 challenge (FIG. 4B). This suggests that arginine decarboxylase is expressed at low levels in S. Typhi during stationary phase culture—a conclusion consistent with the low, but detectable, levels of adiA transcript observed in Ty2.

Substituting the rhamnose promoter P$_{rhaBAD}$ for the native adiA promoter did not affect the degree of acid resistance afforded at low pH. Strains with rhamnose-dependent acid resistance survived low pH challenge as well as their respective parent strain cultured under native decarboxylase-inducing conditions. Cells remained viable for over 4 hours at pH 3.0 and for at least 2 hours at pH 2.5. No protection was afforded against pH 2.0 challenge (data not shown), consistent with previous reports for Salmonella (2, 56). By substituting the rhamnose promoter for the native arginine decarboxylase promoter, we were able to rescue χ11568 (ΔaroD P$_{rhaBAD}$ adiAC), a derivative of the rpoS mutant strain Ty2, from low pH challenge via rhamnose induction of the arginine decarboxylase system (FIG. 3). χ11568 (ΔaroD P$_{rhaBAD}$ adiAC) cells grown under non-inducing conditions (aerobic minimal medium, pH 7) remained viable for over 4 hours at pH 3 when rhamnose was included in the growth medium. This indicates that the activity of the arginine decarboxylase system alone is sufficient for low pH survival in S. Typhi. However, χ11568 (ΔaroD P$_{rhaBAD}$ adiAC) cultured under decarboxylase-inducing conditions (anaerobic rich medium with 0.4% glucose) approximately 100-fold more cells survived pH 3 challenge than when it was cultured aerobically in minimal medium (compare FIG. 3 and FIG. 7A). This is because the growth conditions necessary to induce arginine decarboxylase production in wild-type Salmonella simultaneously induce the stationary phase acid tolerance response (3, 6, 57). The disparity in survival rates between cells cultured aerobically in minimal medium and cells cultured under fermentative conditions underscore the comprehensive nature of the acid response in Salmonella—maximum resistance to low pH is achieved by use of a variety of strategies to counter the effects of low pH.

The rhamnose regulated arginine decarboxylase system was also able to rescue a phoPQ mutant from low pH challenge (FIG. 6). The rhamnose-regulated arginine decarboxylase system in strain χ11622 (ΔphoPQ P$_{rhaBAD}$ adiAC) provided approximately a 1000-fold increase in viability at pH 3.0 over the parent phoPQ mutant (χ8444) when cells were grown aerobically in minimal medium (cells unprepared for low pH). At pH 2.5, the viability of χ11622 (ΔphoPQ P$_{rhaBAD}$ adiAC) after 1 hour exceeded not only that of the parent phoPQ mutant, but also that of the wild-type Ty2. The success of our system at rescuing the phoPQ mutant may be due to two reasons. First, the strains were challenged during stationary phase, when PhoP/PhoQ are less important for acid tolerance (58). Second, a mutation in the phoPQ locus causes a very well characterized sensitivity to inorganic acid (8). At low pH, inorganic acids exist almost exclusively in their dissociated state (free proton with conjugate base), which makes them ideal candidates for neutralization by arginine decarboxylase (it will consume the free protons in the decarboxylase reaction, which immediately raises the intracellular pH and stops further cytoplasmic damage by the free protons). Thus the arginine decarboxylase system is well-poised to compensate for the acid sensitivity imposed by a phoPQ mutation.

Survival of the P$_{araBAD}$ fur mutant (χ11623) was enhanced by P$_{rhaBAD}$ adiAC, although the improvement was not as great as it was for the ΔaroD and ΔphoPQ mutants. The addition of the rhamnose-regulated arginine decarboxylase system improved viability during pH 3 and pH 2.5 challenges, but unlike the phoPQ mutant, the fur mutant only benefited during the first hour of challenge (FIG. 7). The reason for the difficulty of rescue may be two-fold. First, unlike phoPQ mutants, fur mutants are sensitive to organic acids. Inorganic acids such as HCl and organic acids behave quite differently inside the cell, due to differences in their dissociation constants. Our EGA challenge medium contained not only the inorganic acid HCl, but also 10 mM citric acid (37). It is possible that the consumption of free protons by the arginine decarboxylase system is less effective at countering the effects of an organic acid such as citric acid than the strong inorganic acid HCl (8, 23, 37, 59). Second, because the ΔP$_{fur}$::TT araC P$_{araBAD}$ fur mutation was introduced into Ty2, the strain also contains an rpoS mutation. RpoS and Fur jointly regulate a number of key effectors responsible for protection against organic acid. Thus, the combination of fur and rpoS mutations may have rendered χ11623 much more sensitive to acid than the rpoS mutation alone or the combination of phoPQ and rpoS (4, 6). Finally, the P$_{fur}$ mutation may have altered the ability of χ11623 to transport rhamnose, as it required four times the concentration of rhamnose to induce arginine decarboxylase activity as the aroD and phoPQ mutants. Fur is known to regulate expression of a number of outer membrane proteins and other genes that may influence surface structure (60). Thus, it is possible that membrane perturbations due to the lack of Fur in the cell may have resulted in a reduction in rhamnose transport activity by RhaT.

The construction of the rhamnose-regulated arginine decarboxylase system allowed us to increase the acid resistance of *S. Typhi* (to pH 2.5) on demand. Importantly, aerobically grown vaccine strains were protected from pH 3 and pH 2.5. Since the low pH of the gastric environment poses a significant threat to the success of any live attenuated *Salmonella* vaccine, the rhamnose-regulated arginine decarboxylase system represents a novel means to augment survival in this in vivo compartment. Also, because low gastric pH is an important virulence signal, the ability to administer vaccines without stomach pH neutralization may also improve vaccine performance in the host.

TABLE 1

Strains and plasmids used in this study

| Strain or plasmid | Genotype[a] | Derivation or Source |
|---|---|---|
| *E. coli* strains | | |
| BL21 (DE3) | F− ompT hsdS$_B$(r$_B^-$ m$_B^-$) gal dcm (DE3) | Novagen |
| χ7213 | thr-1 leuB6 fhuA21 lacY1 glnV44 recA1 ΔasdA4 Δ(zhf-2::Tn10) thi-1 RP4-2-Tc::Mu [λpir] | (61) |
| χ7573 | Wild type O157: H7 strain 278F2 | J. Giron |
| *S. Typhi* strains | | |
| χ3769(Ty2) | Wild-type, cys trp rpoS | (62) |
| χ8444 | ΔphoPQ | (63) |
| χ11118 | ΔP$_{fur}$::TT araC P$_{araBAD}$ fur | Ty2 |
| χ11500 | Δ(adiA-adiC) | Ty2 |
| χ11548 | ΔaroD | Ty2 |
| χ11552 | ΔaroD ΔP$_{adiA}$::TT araC P$_{araBAD}$ adiA | χ11548 |
| χ11564 | ΔaroD ΔP$_{adiA}$::TT rhaSR P$_{rhaBAD}$adiA | χ11548 |
| χ11568 | ΔaroD ΔP$_{adiA}$::TT rhaSR P$_{rhaBAD}$ adiA Δ(P$_{adiY}$-adiY-P$_{adiC}$) adiC | χ11564 |
| χ11622 | ΔphoPQ ΔP$_{adiA}$::TT rhaSR P$_{rhaBAD}$ adiA Δ(P$_{adiY}$-adiY-P$_{adiC}$) adiC | χ8444 |
| χ11623 | ΔP$_{fur}$::TT araC P$_{araBAD}$ fur ΔP$_{adiA}$::TT rhaSR P$_{rhaBAD}$ adiA Δ(P$_{adiY}$-adiY-P$_{adiC}$) adiC | χ11118 |
| χ11636 | ΔaroD Δ(P$_{adiY}$-adiY-P$_{adiC}$) adiC | χ11548 |
| χ11742 | Δfur | Ty2 |
| *Shigella flexneri* strains | | |
| 2457T | *S. flexneri* 2a, wild-type, Pcr+ Mal−λ− | (64) |
| Plasmids | | |
| pET28a | Protein synthesis vector, T7 promoter; Kan$^r$ | Novagen |
| pJET1.2 | Commercial cloning vector, pMB1 ori, Ap$^r$ | Thermo Scientific |
| pUC18 | Commercial cloning vector, pMB1 ori, Ap$^r$ | Lab stock |
| pYA3700 | Vector encoding the tightly regulated TT araC P$_{araBAD}$ cassette | (65, 66) |
| pYA4181 | Suicide vector to generate the ΔP$_{fur}$::TT araC P$_{araBAD}$ fur mutation | (36) |

TABLE 1-continued

Strains and plasmids used in this study

| Strain or plasmid | Genotype[a] | Derivation or Source |
|---|---|---|
| pYA4278 | Suicide vector, sacB mobRP4 oriR6K; Cm[r] | (67) |
| pYA4895 | Suicide vector to generate the ΔaroD mutation | pYA4278 |
| pYA5066 | Suicide vector to generate the Δ(adiA-adiC) mutation | pYA4278 |
| pYA5072 | Suicide vector to generate the Δ($P_{adiY}$-adiY-$P_{adiC}$) adiC mutation | pYA4278 |
| pYA5075 | Intermediate vector for the creation of Δ$P_{adiA}$::TT araC $P_{araBAD}$ adiA | pYA3700 |
| pYA5081 | Suicide vector specifying the tightly regulated rhaSR $P_{rhaBAD}$ cassette | (68) |
| pYA5085 | Protein synthesis vector with N-terminal His-tag on AdiA | pET28a |
| pYA5089 | Suicide vector to generate the Δ$P_{adiA}$::TT araC $P_{araBAD}$ adiA mutation | pYA4278, pYA5075 |
| pYA5093 | Suicide vector to generate the Δ$P_{adiA}$::TT rhaSR $P_{rhabad}$ adiA mutation | pYA5089, pYA5081 |
| pYA5116 | Suicide vector to generate ΔendA | pYA5103 |
| pYA5119 | Suicide vector to generate ΔendA::clcA | pYA5116 |
| pYA5120 | Suicide vector to generate ΔcysG::TT araC $P_{BAD}$ gadBC | pYA5115 |

[a]In genotype descriptions, the subscripted number refers to a composite deletion and insertion of the indicated gene. P, promoter; TT, T4 ip III transcription terminator; Cm[r], chloramphenicol resistance; Kan[r], kanamycin resistance.

TABLE 2

PCR primers used in the study

| Name | Sequence (5' - 3') | Relevant mutation |
|---|---|---|
| Adi-1 | CCGGTACCGATGGGAATATTCCAGCG | Δ(adiA-adiC) |
| Adi-2 | CCGGATCCCTTTTACCCGGTTGTG | Δ(adiA-adiC) |
| Adi-3 | CCGGATCCCCACGTGTAGTTAATGTTATCGC | Δ(adiA-adiC) |
| Adi-4 | CCAAGCTTGGCAATCACGGCTGCC | Δ(adiA-adiC) |
| Adi-5 | CATGGCATGCCGAATGAGCAAATTC | Δ$P_{adiA}$::TT araC $P_{araBAD}$ adiA |
| Adi-6 | CCGGAGATCTTGATAGTGGTATCCGGCTT | Δ$P_{adiA}$::TT araC $P_{araBAD}$ adiA |
| Adi-7 | CATGGGTACCAGGAGGTAAAAGATGATGAAAG | Δ$P_{adiA}$::TT araC $P_{araBAD}$ adiA |
| Adi-8 | CATGGAGCTCCGCCATAATAATCGTG | Δ$P_{adiA}$::TT araC $P_{araBAD}$ adiA |
| Adi-9 | CATAGCCGTACCATGCTTCGTCG | Regulated adiA constructs |
| Adi-10 | GCGCTCTAGACGCACCACCGACTTCCAG | Δ($P_{adiY}$-adiY-$P_{adiC}$) adiC |
| Adi-11 | GTATCATACCCCCTCAGAATGTTGCAGCAATACTCAG | Δ($P_{adiY}$-adiY-$P_{adiC}$) adiC |
| Adi-12 | TTCCCTGAGTATTGCTGCAACATTCTGAGGGGGTATG | Δ($P_{adiY}$-adiY-$P_{adiC}$) adiC |
| Adi-13 | GCATGGATCCCCAGAACCAGCCGAAG | Δ($P_{adiY}$-adiY-$P_{adiC}$) adiC |
| Adi-14 | CCGGTACCCGAACTCCGTTATTCCTTAC | Δ($P_{adiY}$-adiY-$P_{adiC}$) adiC |
| Adi-15 | CCAAGCTTCAGATAGCCGACGCC | Δ($P_{adiY}$-adiY-$P_{adiC}$) adiC |
| Ara-1 | GATTAGCGGATCCTACCTGACGC | araC $P_{araBAD}$ |
| Aro-1 | CCCGGGTGCTGGCTGAACAGTTCCTCGAG | ΔaroD |
| Aro-2 | CCGGATCCTCCGGCATTATGCAGGCGTCG | ΔaroD |
| Aro-3 | CCGGATCCGCGTGTCCTGTCAGTTTTTTTCTTCTC | ΔaroD |
| Aro-4 | TCTAGATCTCCGCATGGGTACATGAAGTTCCGG | ΔaroD |
| Fur-1 | ACATGCATGCTGTGACTGGGATGACTTCTTCCCG | Δ$P_{fur}$::TT araC $P_{BAD}$ fur |
| Fur-2 | TCCCCCGGGCACTTTTCCGCAATCAAGGCAG | Δ$P_{fur}$::TT araC $P_{BAD}$ fur |
| Rha-1 | GCACTCTAGATTAATCTTTCTGCGAATTG | Δ$P_{adiA}$::TT rhaSR $P_{rhaBAD}$adiA |
| Rha-2 | GCATCTCGAGGCTGAATTTCATTAC | Δ$P_{adiA}$::TT rhaSR $P_{rhaBAD}$adiA |

TABLE 2-continued

PCR primers used in the study

| Name | Sequence (5' - 3') | Relevant mutation |
|---|---|---|
| Rha-3 | TCAGTAACGAGAAGGTCGCG | rhaSR P$_{rhaBAD}$ |
| SQ-1 | GCTGAAATATGACTCCACTCAC | gapA |
| SQ-2 | CGTCAACACCAACTTCGTC | gapA |
| SQ-3 | ACCGACTTCCAGATTATGTTCC | adiA |
| SQ-4 | CGTGTTGATCAGCGTTCCC | adiA |
| Gad-1 | GGCCGAGCTCCTATCCTGCCGCAAACC | ΔcysG::TT araC P$_{BAD}$ gadBC |
| Gad-2 | CAATTCTAGGATAGAATAATAAAGCGGCCGCGACATTACCCCTTAATGGTTG | ΔcysG::TT araC P$_{BAD}$ gadBC |
| Gad-3 | GTTTTTTTGGGCTAGCCTCGAGAGGAGTTTAAAATGGATAAGAAG | ΔcysG::TT araC P$_{BAD}$ gadBC |
| Gad-4 | GAATAACAGGGCTTTATTTTAAGATCTAAAAAGGGAGCGATGAAT | ΔcysG::TT araC P$_{BAD}$ gadBC |
| Gad-5 | CATCGCTCCCTTTTTAGATCTGCCCTGTTATTCAGGGCTTTA | ΔcysG::TT araC P$_{BAD}$ gadBC |
| Gad-6 | GCATGGTACCCGACCAATGCGGCAAC | ΔcysG::TT araC P$_{BAD}$ gadBC |
| Gad-7 | CCCCCTCGAGGGTATGTTTAAAGCTGTTC | ΔcysG::TT araC P$_{BAD}$ gadBC |
| Gad-8 | GGCACCGTTCGTCGCCCCGGATATCG | gadBC seq |
| Gad-9 | CAGGTAAAGCTAAGCAGCTCACATTAC | gadBC seq |
| Gad-10 | CGTTCTGATGTCCCATGTGGCACCGG | gadBC seq |
| Ara-1 | CATTAAGGGGTAATGTCGCGGCCGCTTTATTATTCTATCCTAGAATTGTG | ΔcysG::TT araC P$_{BAD}$ gadBC |
| Ara-2 | CTTCTTATCCATTTTAAACTCCTCTCGAGGCTAGCCCAAAAAACG | ΔcysG::TT araC P$_{BAD}$ gadBC |
| Ara-3 | GATTAGCGGATCCTACCTGACGC | ΔcysG::TT araC P$_{BAD}$ gadBC |

REFERENCES FOR EXAMPLES 1-5

1. Verdu, E., F. Viani, D. Armstrong, R. Fraser, H. H. Slegrist, B. Pignatelli, J. P. Idstrom, C. Cederberg, A. L Blum, and M. Fried. 1994. Effect of omeprazole on intragastric bacterial counts, nitrates, nitrites, and N-nitroso compounds. Gut 35:455-60.
2. Lin, J., I. S. Lee, J. Frey, J. L. Slonczewski, and J. W. Foster. 1995. Comparative analysis of extreme acid survival in *Salmonella typhimurium, Shigella flexneri*, and *Escherichia coli*. J Bacteriol 177:4097-104.
3. Kieboom, J., and T. Abee. 2006. Arginine-dependent acid resistance in *Salmonella enterica* serovar *Typhimurium*. J Bacteriol 188:5650-3.
4. Foster, J. W. 1993. The acid tolerance response of *Salmonella Typhimurium* involves transient synthesis of key acid shock proteins. J Bacteriol 175:1981-7.
5. Foster, J. W., and M. P. Spector. 1995. How *Salmonella* survive against the odds. Annu Rev Microbiol 49:145-74.
6. Lee, I. S., J. Lin, H. K. Hall, B. Bearson, and J. W. Foster. 1995. The stationary-phase sigma factor sigma S (RpoS) is required for a sustained acid tolerance response in virulent *Salmonella typhimurium*. Mol Microbiol 17:155-67.
7. Hall, H. K., and J. W. Foster. 1996. The role of fur in the acid tolerance response of *Salmonella Typhimurium* is physiologically and genetically separable from its role in iron acquisition. J Bacteriol 178:5683-91.
8. Bearson, B. L., L. Wilson, and J. W. Foster. 1998. A low pH-regulatable, PhoPQ-dependent acid tolerance response protects *Salmonella Typhimurium* against inorganic acid stress. J Bacteriol 180:2409-17.
9. Robbe-Saule, V., and F. Norel. 1999. The rpoS mutant allele of *Salmonella typhi* Ty2 is identical to that of the live typhoid vaccine Ty21a. FEMS Microbiol Lett 170:141-3.
10. Germanier, R., and E. Furer. 1975. Isolation and characterization of Gal E mutant Ty 21a of *Salmonella typhi*: a candidate strain for a live, oral typhoid vaccine. J Infect Dis 131:553-8.
11. Germanier, R., and E. Furer. 1983. Characteristics of the attenuated oral vaccine strain "*S. typhi*" Ty 21a. Dev Biol Stand 53:3-7.
12. Hone, D., R. Morona, S. Attridge, and J. Hackett. 1987. Construction of defined galE mutants of *Salmonella* for use as vaccines. J Infect Dis 156:167-74.
13. Hone, D. M., A. M. Harris, and M. M. Levine. 1994. Adaptive acid tolerance response by *Salmonella typhi* and candidate live oral typhoid vaccine strains. Vaccine 12:895-8.
14. Hohmann, E. L., C. A. Oletta, K. P. Killeen, and S. I. Miller. 1996. phoP/phoQ-deleted *Salmonella typhi*

(Ty800) is a safe and immunogenic single-dose typhoid fever vaccine in volunteers. J Infect Dis 173:1408-14.
15. Shi, H., S. Wang, K. L. Roland, B. M. Gunn, and R. Curtiss, 3rd. 2010. Immunogenicity of a live recombinant *Salmonella* vaccine expressing pspA in neonates and infant mice born from naive and immunized mothers. Clin Vaccine Immunol.
16. Tacket, C. O., M. B. Sztein, G. A. Losonsky, S. S. Wasserman, J. P. Nataro, R. Edelman, D. Pickard, G. Dougan, S. N. Chatfield, and M. M. Levine. 1997. Safety of live oral *Salmonella typhi* vaccine strains with deletions in htrA and aroC aroD and immune response in humans. Infect Immun 65:452-6.
17. Tacket, C. O., D. M. Hone, R. Curtiss, 3rd, S. M. Kelly, G. Losonsky, L. Guers, A. M. Harris, R. Edelman, and M. M. Levine. 1992. Comparison of the safety and immunogenicity of ☐aroC☐aroD and ☐cya☐crp *Salmonella typhi* strains in adult volunteers. Infect Immun 60:536-41.
18. Kirkpatrick, B. D., K. M. Tenney, C. J. Larsson, J. P. O'Neill, C. Ventrone, M. Bentley, A. Upton, Z. Hindle, C. Fidler, D. Kutzko, R. Holdridge, C. Lapointe, S. Hamlet, and S. N. Chatfield. 2005. The novel oral typhoid vaccine M01ZH09 is well tolerated and highly immunogenic in 2 vaccine presentations. J Infect Dis 192:360-6.
19. DIPetrillo, M. D., T. Tibbetts, H. Kleanthous, K. P. Killeen, and E. L. Hohmann. 1999. Safety and immunogenicity of phoP/phoQ-deleted *Salmonella typhi* expressing *Helicobacter pylori* urease in adult volunteers. Vaccine 18:449-59.
20. Gilman, R. H., R. B. Hornick, W. E. Woodard, H. L. DuPont, M. J. Snyder, M. M. Levine, and J. P. Libonati. 1977. Evaluation of a UDP-glucose-4-epimeraseless mutant of *Salmonella typhi* as a live oral vaccine. J Infect Dis 136:717-23.
21. Black, R., M. M. Levine, C. Young, J. Rooney, S. Levine, M. L. Clements, S. O'Donnell, T. Hugues, and R. Germanier. 1983. Immunogenicity of Ty21a attenuated *Salmonella typhi* given with sodium bicarbonate or in enteric-coated capsules. Dev Biol Stand 53:9-14.
22. Levine, M. M., C. Ferreccio, R. E. Black, and R. Germanier. 1987. Large-scale field trial of Ty21a live oral typhoid vaccine in enteric-coated capsule formulation. Lancet 1:1049-52.
23. Baik, H. S., S. Bearson, S. Dunbar, and J. W. Foster. 1996. The acid tolerance response of *Salmonella typhimurium* provides protection against organic acids. Microbiology 142 (Pt 11):3195-200.
24. Groisman, E. A., J. Kayser, and F. C. Soncini. 1997. Regulation of polymyxin resistance and adaptation to low-Mg2+ environments. J Bacteriol 179:7040-5.
25. Rychlik, I., and P. A. Barrow. 2005. *Salmonella* stress management and its relevance to behaviour during intestinal colonisation and infection. FEMS Microbiol Rev 29:1021-40.
26. Durant, J. A., D. E. Corrier, and S. C. Ricke. 2000. Short-chain volatile fatty acids modulate the expression of the hilA and invF genes of *Salmonella typhimurium*. J Food Prot 63:573-8.
27. Lee, A. K., C. S. Detweiler, and S. Falkow. 2000. OmpR regulates the two-component system SsrA-SsrB in *Salmonella* pathogenicity island 2. J Bacteriol 182:771-81.
28. Richard, H., and J. W. Foster. 2004. *Escherichia coli* glutamate- and arginine-dependent acid resistance systems increase internal pH and reverse transmembrane potential. J Bacteriol 186:6032-41.
29. Gong, S., H. Richard, and J. W. Foster. 2003. YjdE (AdiC) is the arginine:agmatine antiporter essential for arginine-dependent acid resistance in *Escherichia coli*. J Bacteriol 185:4402-9.
30. Andrell, J., M. G. Hicks, T. Palmer, E. P. Carpenter, S. Iwata, and M. J. Maher. 2009. Crystal structure of the acid-induced arginine decarboxylase from *Escherichia coli*: reversible decamer assembly controls enzyme activity. Biochemistry 48:3915-27.
31. Blethen, S. L., E. A. Boeker, and E. E. Snell. 1968. Arginine decarboxylase from *Escherichia coli*. I. Purification and specificity for substrates and coenzyme. J Biol Chem 243:1671-7.
32. Iyer, R., C. Williams, and C. Miller. 2003. Arginine-agmatine antiporter in extreme acid resistance in *Escherichia coli*. J Bacteriol 185:6556-61.
33. Auger, E. A., K. E. Redding, T. Plumb, L. C. Childs, S. Y. Meng, and G. N. Bennett. 1989. Construction of lac fusions to the regulatable arginine- and lysine decarboxylase genes of *Escherichia coli* K12. Mol Microbiol 3:609-20.
34. Kaniga, K., I. Delor, and G. R. Cornelis. 1991. A wide-host-range suicide vector for improving reverse genetics in gram-negative bacteria: inactivation of the blaA gene of *Yersinia enterocolitica*. Gene 109:137-41.
35. Kang, H. Y., C. M. Dozois, S. A. Tinge, T. H. Lee, and R. Curtiss, 3rd. 2002. Transduction-mediated transfer of unmarked deletion and point mutations through use of counterselectable suicide vectors. J Bacteriol 184:307-12.
36. Curtiss, R., 3rd, S. Y. Wanda, B. M. Gunn, X. Zhang, S. A. Tinge, V. Ananthnarayan, H. Mo, S. Wang, and W. Kong. 2009. *Salmonella enterica* serovar *Typhimurium* strains with regulated delayed attenuation in vivo. Infect Immun 77:1071-82.
37. Vogel, H. J., and D. M. Bonner. 1956. Acetylornithinase of *Escherichia coli*: partial purification and some properties. J Biol Chem 218:97-106.
38. De Biase, D., A. Tramonti, R. A. John, and F. Bossa. 1996. Isolation, overexpression, and biochemical characterization of the two isoforms of glutamic acid decarboxylase from *Escherichia coli*. Protein Expr Purif 8:430-8.
39. Sambrook, and Russell. 2001. Molecular Cloning: A Laboratory Manual, vol. 3. Cold Spring Harbor Press, Plainview Harbor, N.Y.
40. Laemmli, U. K. 1970. Cleavage of structural proteins during the assembly of the head of bacteriophage T4. Nature 227:680-5.
41. Towbin, H., T. Staehelin, and J. Gordon. 1989. Immunoblotting in the clinical laboratory. J Clin Chem Clin Biochem 27:495-501.
42. Rice, E. W., C. H. Johnson, M. E. Dunnigan, and D. J. Reasoner. 1993. Rapid glutamate decarboxylase assay for detection of *Escherichia coli*. Appl Environ Microbiol 59:4347-9.
43. Castanie-Comet, M. P., T. A. Penfound, D. Smith, J. F. Elliott, and J. W. Foster. 1999. Control of acid resistance in *Escherichia coli*. J Bacteriol 181:3525-35.
44. Berk, P. A., R. Jonge, M. H. Zwietering, T. Abee, and J. Kieboom. 2005. Acid resistance variability among isolates of *Salmonella enterica* serovar *Typhimurium* DT104. J Appl Microbiol 99:859-66.

45. Hoiseth, S. K., and B. A. Stocker. 1981. Aromatic-dependent *Salmonella typhimurium* are non-virulent and effective as live vaccines. Nature 291:238-9.
46. Haldimann, A., L. L. Daniels, and B. L Wanner. 1998. Use of new methods for construction of tightly regulated arabinose and rhamnose promoter fusions in studies of the *Escherichia coli* phosphate regulon. J Bacteriol 180:1277-86.
47. Lee, N. L., W. O. Gielow, and R. G. Wallace. 1981. Mechanism of araC autoregulation and the domains of two overlapping promoters, $P_c$ and $P_{BAD}$, in the L-arabinose regulatory region of *Escherichia coli*. Proc Natl Acad Sci USA 78:752-6.
48. Guzman, L. M., D. Belin, M. J. Carson, and J. Beckwith. 1995. Tight regulation, modulation, and high-level expression by vectors containing the arabinose $P_{BAD}$ promoter. J Bacteriol 177:4121-30.
49. Kong, W., S. Y. Wanda, X. Zhang, W. Bollen, S. A. Tinge, K. L. Roland, and R. Curtiss, 3rd. 2008. Regulated programmed lysis of recombinant *Salmonella* in host tissues to release protective antigens and confer biological containment. Proc Natl Acad Sci USA 105:9361-6.
50. Lee, J. H., R. J. Russo, L. Heffernan, and G. Wilcox. 1982. Regulation of L-arabinose transport in *Salmonella typhimurium* LT2. Mol Gen Genet. 185:136-41.
51. Tate, C. G., J. A. Muiry, and P. J. Henderson. 1992. Mapping, cloning, expression, and sequencing of the rhaT gene, which encodes a novel L-rhamnose-H+ transport protein in *Salmonella typhimurium* and *Escherichia coli*. J Biol Chem 267:6923-32.
52. Chai, L. C., B. H. Kong, O. I. Elemfareji, and K. L. Thong. 2012. Variable carbon catabolism among *Salmonella enterica* serovar *Typhi* isolates. PLoS One 7:e36201.
53. Tobin, J. F., and R. F. Schleif. 1987. Positive regulation of the *Escherichia coli* L-rhamnose operon is mediated by the products of tandemly repeated regulatory genes. J Mol Biol 196:789-99.
54. Egan, S. M., and R. F. Schleif. 1993. A regulatory cascade in the induction of rhaBAD. J Mol Biol 234:87-98.
55. Stim, K. P., and G. N. Bennett. 1993. Nucleotide sequence of the adi gene, which encodes the biodegradative acid-induced arginine decarboxylase of *Escherichia coli*. J Bacteriol 175:1221-34.
56. Foster, J. W. 1999. When protons attack: microbial strategies of acid adaptation. Curr Opin Microbiol 2:170-4.
57. de Jonge, R., W. S. Ritmeester, and F. M. van Leusden. 2003. Adaptive responses of *Salmonella enterica* serovar *Typhimurium* DT104 and other *S. Typhimurium* strains and *Escherichia coli* O157 to low pH environments. J Appl Microbiol 94:625-32.
58. Foster, J. W., and H. K. Hall. 1990. Adaptive acidification tolerance response of *Salmonella typhimurium*. J Bacteriol 172:771-8.
59. McHan, F., and E. B. Shotts. 1993. Effect of short-chain fatty acids on the growth of *Salmonella typhimurium* in an in vitro system. Avian Dis 37:396-8.
60. Troxell, B., R. C. Fink, S. Porwollik, M. McClelland, and H. M. Hassan. 2011. The Fur regulon in anaerobically grown *Salmonella enterica* sv. *Typhimurium*: identification of new Fur targets. BMC Microbiol 11:236.
61. Roland, K., R. Curtiss, 3rd, and D. Sizemore. 1999. Construction and evaluation of a ☐cya ☐crp *Salmonella typhimurium* strain expressing avian pathogenic *Escherichia coli* O78 LPS as a vaccine to prevent airsacculitis in chickens. Avian Dis 43:429-41.
62. Felix, A., and R. M. Pitt. 1951. The pathogenic and immunogenic activities of *Salmonella typhi* in relation to its antigenic constituents. J Hyg (Lond) 49:92-110.
63. Brenneman, K. E., C. McDonald, S. M. Kelly-Aehle, K. L. Roland, and R. Curtiss, 3rd. 2012. Use of RapidChek® SELECT *Salmonella* to detect shedding of live attenuated *Salmonella enterica* serovar *Typhi* vaccine strains. J Microbiol Methods 89:137-47.
64. Formal, S. B., G. J. Dammin, E. H. Labrec, and H. Schneider. 1958. Experimental *Shigella* infections: characteristics of a fatal infection produced in guinea pigs. J Bacteriol 75:604-10.
65. Wang, S., Y. L1, H. Shi, G. Scarpellini, A. Torres-Escobar, K. L. Roland, and R. Curtiss, 3rd. 2010. Immune responses to recombinant pneumococcal PsaA antigen delivered by a live attenuated *Salmonella* vaccine. Infect Immun 78:3258-71.
66. Santander, J., S. Y. Wanda, C. A. Nickerson, and R. Curtiss, 3rd. 2007. Role of RpoS in fine-tuning the synthesis of Vi capsular polysaccharide in *Salmonella enterica* serotype *Typhi*. Infect Immun 75:1382-92.
67. Kong, Q., J. Yang, Q. Liu, P. Alamuri, K. L. Roland, and R. Curtiss, 3rd. 2011. Effect of deletion of genes involved in lipopolysaccharide core and O-antigen synthesis on virulence and immunogenicity of *Salmonella enterica* serovar *Typhimurium*. Infect Immun 79:4227-39.
68. Kong, W., M. Brovold, J. Tully, L. Benson and R. Curtiss III. 2012. Presented at the ASM 112th General Meeting, San Francisco, Calif., Jun. 16-19, 2012.
69. Frey, S. E., H. Hill, K. R. Lottenbach, K. E. Brenneman, Y. Zhang, S. M. Kelly-Aehle, C. McDonald, A. Jansen and Roy Curtiss III. 2013. A phase I, dose-escalation trial in adults of three recombinant attenuated *Salmonella Typhi* vaccine vectors producing *Streptococcus pneumoniae* surface protein antigen PspA. Vaccine 31:4874-4880.

Example 6

Sugar-Inducible Amino Acid Decarboxylase Systems

Glutamate Decarboxylase.

Figure 9:
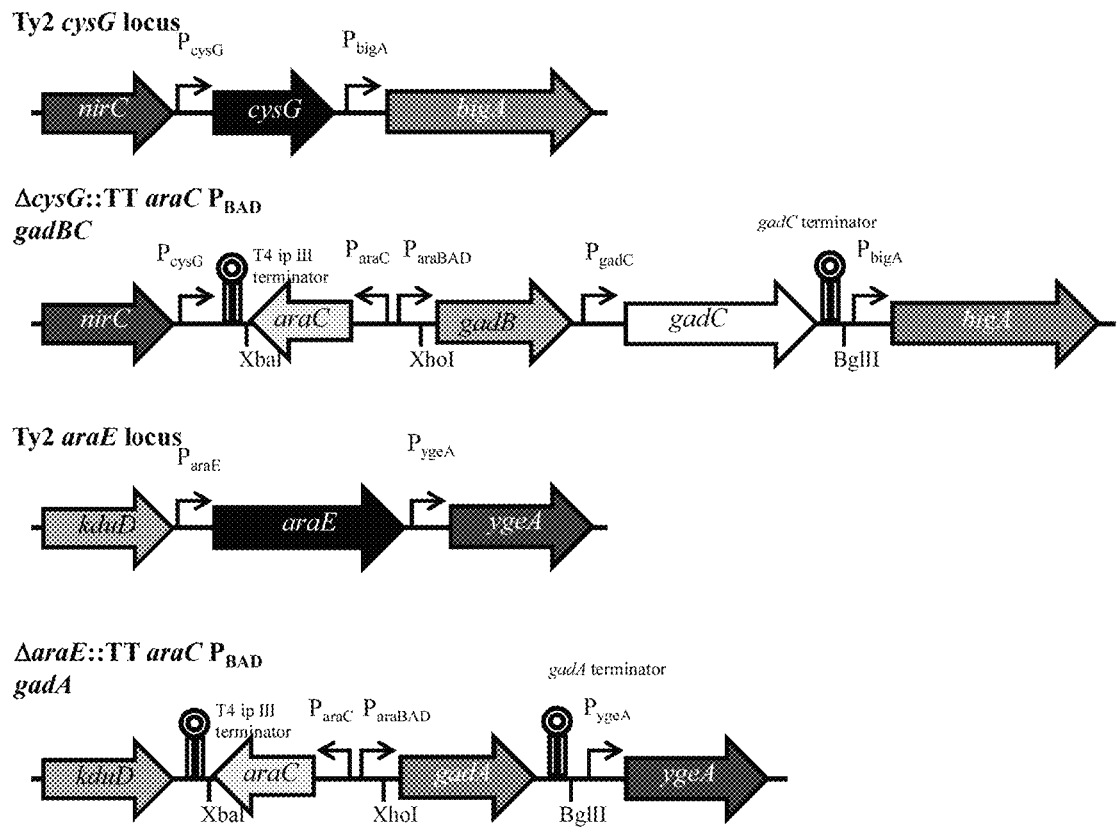
FIG. 9. Schematic diagram of glutamate decarboxylase constructions. The genes and associated regulatory sequences for the ΔcysG and ΔcysG::TT araC $P_{BAD}$ gadBC mutations are shown above along with the hypothetical sequence mutations ΔaraE and ΔaraE::TT araC $P_{BAD}$ gadA. The wild-type cysG and araE loci of S. Typhi Ty2 depicted for comparative purposes. The diagram is approximately to scale. (→) promoter; (⚲) transcription terminator.

The glutamate decarboxylase (GAD) system of *E. coli* O157:H7 is composed of two homologous decarboxylases (GadA and GadB) and a glutamate/γ-aminobutyric acid antiporter (GadC) (15). GadA and GadB are biochemically indistinguishable and only one is required for survival at pH 2.5 in *E. coli*. However, both are required for survival at pH 2 (5, 6). In *E. coli*, this system maintains an internal pH between 4-5 (14). Based on our findings that the antiporter is required for acid resistance in the AdiA system, we took advantage of the fact that gadB and gadC are co-transcribed from a single operon (5) (gadA is located at a distant site on the chromosome (15)) by cloning the gadBC operon and placing it under transcriptional control of the araC $P_{BAD}$ promoter. To accomplish this, we engineered an operon substitution mutation into the cysG locus: ΔcysG::TT araC $P_{BAD}$ gadBC. We fused the arabinose-regulator cassette containing araC, the araC promoter, and the $P_{BAD}$ promoter to the flanking region upstream of the cysG locus in *Salmonella Typhi* Ty2 (FIG. 9). The upstream flanking region was amplified by PCR from Ty2 using primers Gad-1 and -2

(Table 2); the araC cassette was amplified by PCR from plasmid pYA3700 using primers Ara-1 and -2. The two DNA segments were joined by overlap PCR and re-amplified with primers Gad-1 and Ara-2. The overlap PCR product was ligated into pUC18 at the SalI/XhoI and SacI sites to produce the intermediate vector pYA5105. The strong transcription terminator T4 ip III placed between the upstream nirC gene and araC prevents expression of antisense RNA as well as transcription due to the cysG promoter that remains within the coding sequence of nirC.

We fused the gadBC operon with the cysG downstream flanking region. Flanking DNA was amplified by PCR from Ty2 using primers Gad-3 and -4; the gadBC operon was amplified from enterohemorrhagic $E.$ $coli$ strain $\chi$7573 using primers Gad-5 and -6. The two DNA segments were joined by overlap PCR and re-amplified with primers Gad-3 and -6. The overlap product was ligated into pCR2.1 TOPO to generate pYA5101. The upstream flanking region-araC fusion from pYA5105 and the gadBC operon-downstream flanking region fusion from pYA5101 were amplified using Gad-1/Ara-2 and Gad-3/-6 respectively (see above) and joined by overlap PCR and re-amplified with primers Gad-1 and -6. This PCR product was ligated into pJET1.2 to produce intermediate vector, pYA5115. The intergenic region between the araC cassette and gadBC operon was confirmed by PCR primers, Ara-3 and Gad-7. We confirmed the sequence integrity of the gadBC operon using primers Gad-8, -9 and -10. The fusion product from pYA5115 was amplified with primers Gad-1 and -6 and ligated into pYA4278 at the Ahdl sites, generating the suicide vector pYA5120. pYA5120 was introduced into $Salmonella$ $Typhi$ Ty2 phoPQ mutant, $\chi$8444, by conjugation to produce $\chi$11760. The generation and activity of $E.$ $coli$ decarboxylase within $Salmonella$ was verified by Western blot, acid resistance survival and glutamate decarboxylase assay.

Figure 10:
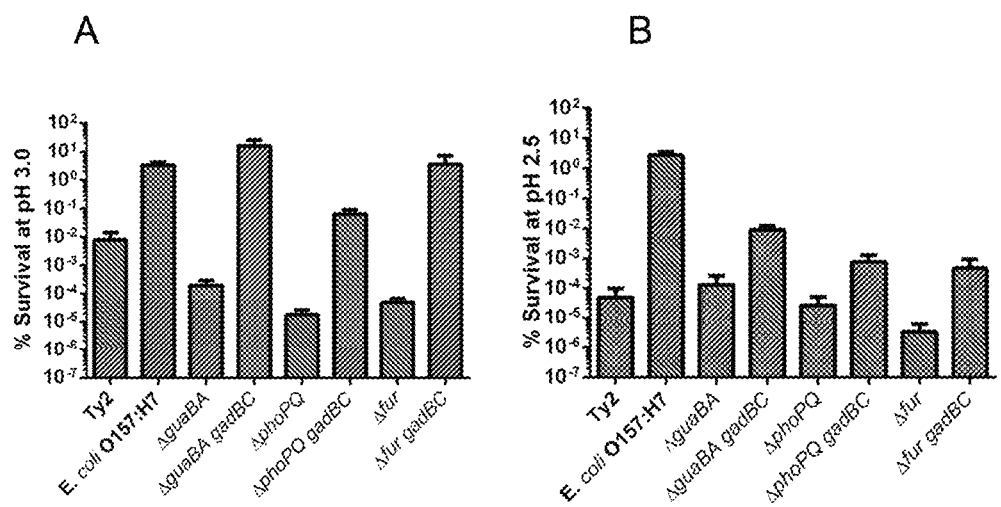
FIG. 10. Survival of S. Typhi strains during in vitro low pH challenge. Strains were grown to stationary phase in EGA medium, pH 7.0 containing arabinose with aeration, then washed and challenged in EG medium containing 1 mM glutamic acid. ΔguaBA, ΔphoPQ, and Δfur mutants were challenged at pH 3.0 (A) or pH 2.5 (B) for 1 h. Data are presented as the mean and SEM for each time point.
Figure 11:
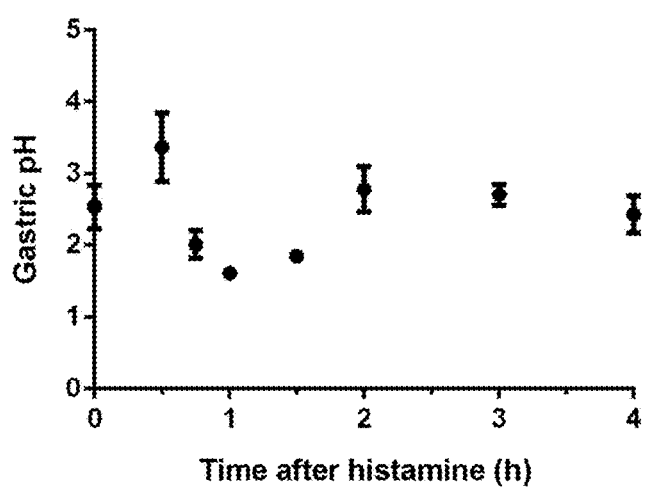
FIG. 11. Gastric pH following histamine injection. Following a 6 hour fast, mice were injected subcutaneously with 10 mg/kg histamine. Mice were anaesthetized with pentobarbital prior to gastric surgery. Gastric pH was measured at the mucosal surface of the stomach for up to 4 hours post histamine injection. Data shown are the mean and standard deviation of at least five mice per time point.
Figure 12:
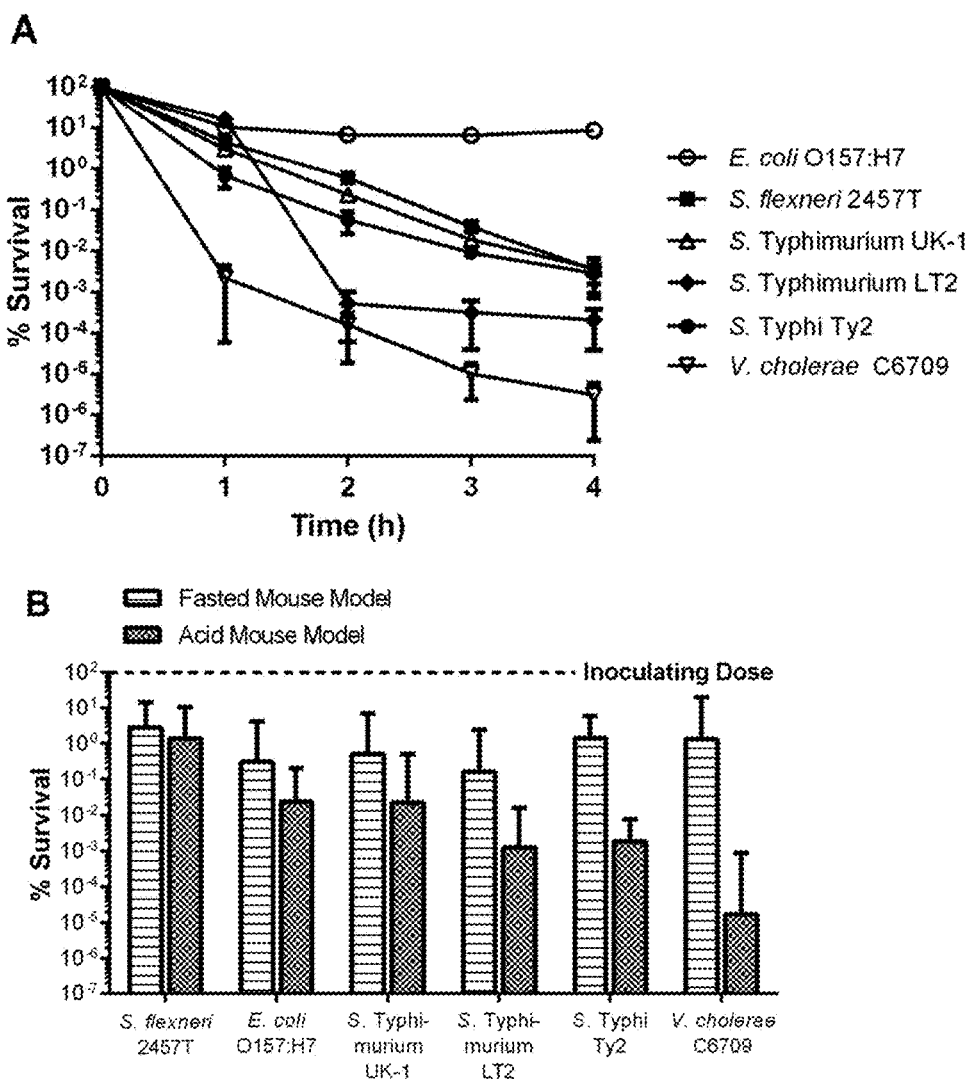
FIG. 12. Survival of strains cultured under non-acid resistance inducing conditions. Wild-type enteric strains were grown in LB medium to late log phase under aerobic conditions. (A) Cells were washed and challenged in EG medium (pH 3.0) containing 0.1% casamino acids. Survival during EG medium challenge was assayed hourly for 4 hours by plating onto LB agar. Data shown are the mean and SEM of three independent experiments. (B) Cells were washed and then resuspended in PBS containing 0.1% casamino acids. Mice were either fasted for 6 hours (fasted mouse model) or fasted and low gastric pH was induced by histamine injection (acid mouse model) and then inoculated with $10^9$ CFU of each strain. Cells contained the pWSK129 plasmid ($Kan^R$) to enhance recovery from intestinal tissues. Sixty minutes after inoculation, mice were euthanized and the entire small intestine removed and homogenized. Survival was assayed by plating onto LB agar containing kanamycin. Data are expressed as the percent of initial inoculum recovered (% survival). The geometric mean and 95% confidence interval of two independent experiments (8 mice total) is depicted.
Figure 13:
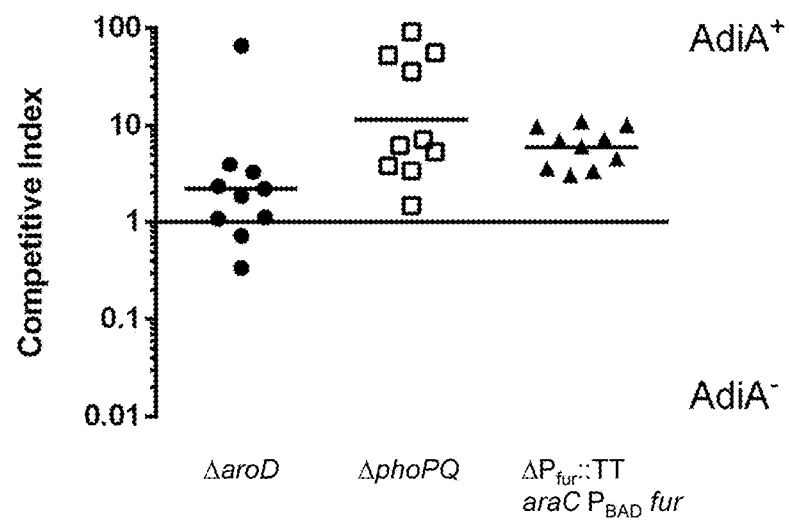
FIG. 13. Effect of arginine decarboxylase on the gastric survival of S. Typhi. Pairs of attenuated S. Typhi strains differing only in their arginine decarboxylase locus were grown to stationary phase in EGA medium under aerobic conditions. Cells were combined in a 1:1 ratio in PBS containing 1 mM arginine. Low gastric pH was induced by histamine injection in mice fasted for 6 h. Mice were inoculated with $10^9$ CFU of each strain. Sixty min after inoculation, mice were euthanized and the entire small intestine removed and homogenized. Strain survival was assayed by plating onto LB agar containing kanamycin or streptomycin. Data shown are the competitive index of the two strains in each mouse with the geometric mean of two independent experiments (10 mice total) indicated as a solid line.
Figure 14:
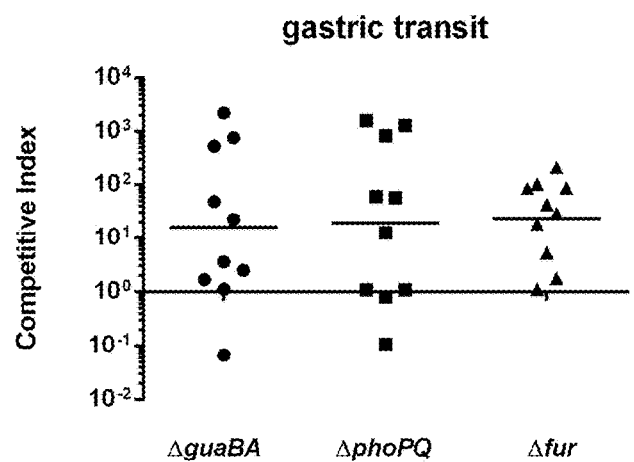
FIG. 14. Effect of glutamate decarboxylase on the gastric survival of S. Typhi. Pairs of attenuated S. Typhi strains differing only in their glutamate decarboxylase locus were grown to stationary phase in EGA medium under aerobic conditions. Cells were combined in a 1:1 ratio in PBS containing 1 mM glutamic acid. Low gastric pH was induced by histamine injection in mice fasted for 6 h. Mice were inoculated with $10^9$ CFU of each strain. Sixty min after inoculation, mice were euthanized and the entire small intestine removed and homogenized. Strain survival was assayed by plating onto LB agar containing kanamycin or streptomycin. Data shown are the competitive index of the two strains in each mouse with the geometric mean of two independent experiments (10 mice total) indicated as a solid line.

Using pYA5120, the araC $P_{BAD}$ gadBC construct (FIG. 9) was introduced into several $S.$ $Typhi$ strains, each carrying a mutation known to attenuate $Salmonella$, $\Delta$guaBA (19), $\Delta$phoPQ (9, 10) or $\Delta$fur (4, 20). Note that $Salmonella$ strains with mutations in either phoPQ (8) or fur (7) are extremely acid sensitive. In addition, preliminary results indicate that our $\Delta$guaBA $S.$ $Typhi$ mutant is also more sensitive to acid shock than its Ty2 parent (data not shown). Although this phenotype has not been documented in the literature, it is interesting to note that a previous study reported that in $E.$ $coli$, GuaB synthesis is induced by exposure to low pH (21). The araC $P_{BAD}$ gadBC system confers sugar-inducible acid resistance to all three mutant strains when $S.$ $Typhi$ cells are grown aerobically at pH 7.0 (FIG. 10). In fact, the survival of strains carrying this system was greater than wild-type Ty2 grown under the same conditions.

Low Gastric pH Mouse Model. While In vitro acid resistance assays provide good preliminary information, an animal model will give us a better idea of how our strains will behave in the clinic. As mentioned above, the gastric environment of a fasted mouse is around pH 4 (12) compared to a fasted human, whose stomach pH is around 2 (17). This difference can have a profound effect on *Salmonella* survival and could provide data that does not reflect what will happen in humans. To create a gastric pH closer to the human stomach, we took advantage of the observation that injecting mice with histamine transiently increases HCl secretion by parietal cells lining the stomach (3). Note that in this model, mice are injected with the H1 antagonist chlorpheniramine prior to injection with histamine to block an allergic reaction (3). This approach was also used in a study to establish the significance of low gastric pH as a barrier to infection (16). Based on these observations, we have adapted this model to evaluate the ability of attenuated *Salmonella* to transit the stomach (22). In preliminary studies, we monitored gastric pH in live mice as a function of time after histamine injection (FIG. 11). Our results indicated that the minimum pH was reached after one hour.

To validate the low gastric pH mouse model, we monitored survival of a variety of enteric pathogens in fasted mice with or without histamine injection. For these experiments, cells were grown in LB and either challenged at pH 3.0 in vitro (FIG. 12A) or used to inoculate fasted mice with or without histamine injection. In all cases, survival was less in the low pH mouse than in the fasted mouse (FIG. 12B). Not surprisingly, the *Vibrio cholerae* strain underwent the most killing, consistent with our in vitro results.

Survival of *S. Typhi* Strains Carrying Sugar-Inducible Acid Resistance Systems in the Low Gastric pH Mouse Model. To evaluate the impact of these systems in low gastric pH mice, we set up a co-infection experiment in which strains with or without the rhamnose inducible adiAC genes carried plasmids with different antibiotic resistance markers. Strains were grown aerobically with 0.1% rhamnose and used to co-infect fasted, low gastric pH mice. Overall, induction of adiAC enhanced the survival of all strains (FIG. 13). The greatest increase in survival, 10-fold, was observed in the ΔphoPQ strain, consistent with our published in vitro results, which showed that the rhamnose-inducible adiAC system had the greatest impact on the ΔphoPQ mutant. A similar experiment was performed to evaluate strains carrying arabinose-inducible gadBC. Survival of all strains was enhanced about 10-fold (FIG. 14). Taken together, these results demonstrate that both systems are capable of increasing the survival of a variety of *S. Typhi* strains carrying mutations that can be used to attenuate virulence for use as human vaccines.

Lysine Decarboxylase System. In addition to the adiAC and gadBC systems, resistance to acid shock can also be mediated by the AR4 system, lysine decarboxylase and lysine:cadaverine antiporter, encoded by cadA and cadB, respectively (13). In *Salmonella*, the cadAB genes are present as an operon and are induced by low pH and anaerobiosis, in a CadC-dependent manner when lysine is present (13). The cadAB system also plays a role in the acid tolerance response (13). This system greatly enhances the ability of *Salmonella* to survive an acid challenge at pH 2.3 after overnight anaerobic growth in a rich medium at pH 5 (18). Unlike adiAC or gadBC, this system can also enhance the growth of *Salmonella* at a moderately acidic pH of 4.5. Notably, this is observed under both aerobic and anaerobic growth conditions, which may be of additional benefit during vaccine preparation and transit through the stomach. In addition, this system lead to an increase the pH external to the cell, which may have benefits in the macrophage lysosome. To evaluate this system, we will construct *S. Typhi* vaccine strains (e.g ΔphoP, Δfur, ΔguaAB) in which cadAB expression is driven by a sugar-inducible promoter and characterize them in vitro, as we have done for adiAC and gadBC.

Construction of an *S. Typhi* Vaccine Strain with Enhanced Survival at pH 2.0. (i) Addition of gadA to strains carrying a sugar-regulated gadBC operon. In *E. coli*, GadA and GadB are nearly identical isoforms of glutamate decarboxylase located at different places on the chromosome (15). The gadBC operon alone is effective acid protection at pH 2.5, while both gadA and gadBC are required for maximum rates of survival at pH 2.0 (2). We observed similar results in that insertion of the gadBC into *S. Typhi* protects well against acid shock down to pH 2.5 (FIG. 10), but is ineffective against a pH 2.0 challenge (data not shown). Thus, it may be possible to enhance *S. Typhi* survival by introduction of an araC $P_{BAD}$ gadA construct into strains already carrying araC $P_{BAD}$ gadBC. The gadA gene will be inserted into the chromosome by substituting it for araE. Deletion of araE does not affect the virulence of *S. Typhimurium* (data not shown). The construction of the araC $P_{BAD}$ gadA cassette will be done essentially as we have described for araC $P_{BAD}$ adiA (1) and araC $P_{BAD}$ gadBC.

Addition of Chloride Channel Protein ClcA from *E. coli. Survival below pH* 3 in *E. coli* is predicated on the reversal of the transmembrane potential (14). Currently no data are available to indicate whether this occurs in *Salmonella*, but it is likely that this will be the case. To test this, we will introduce the CIC chloride channel (eriC/clcA) from *E. coli*, using suicide plasmid pYA5119, as this has been shown to be an essential player in acid resistance by preventing membrane hyperpolarization at low pH (11, 14). Although *S. Typhimurium* and *S. Typhi* contain genes designated as CIC channels, alignment with the *E. coli* eriC reveals no significant homology and casts doubt on the ability of the *Salmonella* channels to serve as a substitute at low pH.

REFERENCES CITED IN EXAMPLE 6

1. Brenneman, K. E., C. Willingham, W. Kong, R. Curtiss, 3rd, and K. L Roland. 2013. Low pH Rescue of Acid-Sensitive *Salmonella Typhi* Strains by a Rhamnose-Regulated Arginine Decarboxylase System. J. Bacteriol. 195:3062-3072.
2. Castanie-Comet, M. P., T. A. Penfound, D. Smith, J. F. Elliott, and J. W. Foster. 1999. Control of acid resistance in *Escherichia coli*. J Bacteriol 181:3525-3535.
3. Chew, C. S., X. Chen, R. J. Bollag, C. Isales, K. H. Ding, and H. Zhang. 2008. Targeted disruption of the Lasp-1 gene is linked to increases in histamine-stimulated gastric HCl secretion. Am J Physiol Gastrointest Liver Physiol 295:G37-G44.
4. Curtiss, R., 3rd, S. Y. Wanda, B. M. Gunn, X. Zhang, S. A. Tinge, V. Ananthnarayan, H. Mo, S. Wang, and W. Kong. 2009. *Salmonella* strains with regulated delayed attenuation in vivo. Infect Immun.
5. De Biase, D., A. Tramonti, F. Bossa, and P. Visca. 1999. The response to stationary-phase stress conditions in *Escherichia coli*: role and regulation of the glutamic acid decarboxylase system. Mol Microbiol 32:1198-1211.
6. De Biase, D., A. Tramonti, R. A. John, and F. Bossa. 1996. Isolation, overexpression, and biochemical characterization of the two isoforms of glutamic acid decarboxylase from *Escherichia coli*. Protein Expr Purif 8:430-438.
7. Foster, J. W. 1991. *Salmonella* acid shock proteins are required for the adaptive acid tolerance response. J Bacteriol 173:6896-6902.
8. Foster, J. W., and H. K. Hall. 1990. Adaptive acidification tolerance response of *Salmonella typhimurium*. J Bacteriol 172:771-778.
9. Galan, J. E., and R. Curtiss, 3rd. 1989. Virulence and vaccine potential of phoP mutants of *Salmonella Typhimurium*. Microb Pathog 6:433-443.
10. Hohmann, E. L., C. A. Oletta, K. P. Killeen, and S. I. Miller. 1996. phoP/phoQ-deleted *Salmonella typhi* (Ty800) is a safe and immunogenic single-dose typhoid fever vaccine in volunteers. J Infect Dis 173:1408-1414.
11. Iyer, R., T. M. Iverson, A. Accardi, and C. Miller. 2002. A biological role for prokaryotic CIC chloride channels. Nature 419:715-718.
12. McConnell, E. L., A. W. Basit, and S. Murdan. 2008. Measurements of rat and mouse gastrointestinal pH, fluid and lymphoid tissue, and implications for in-vivo experiments. J Pharm Pharmacol 60:63-70.
13. Neely, M. N., and E. R. Olson. 1996. Kinetics of expression of the *Escherichia coli* cad operon as a function of pH and lysine. J Bacteriol 178:5522-5528.
14. Richard, H., and J. W. Foster. 2004. *Escherichia coli* glutamate- and arginine-dependent acid resistance systems increase internal pH and reverse transmembrane potential. J Bacteriol 186:6032-6041.
15. Smith, D. K., T. Kassam, B. Singh, and J. F. Elliott. 1992. *Escherichia coli* has two homologous glutamate decarboxylase genes that map to distinct loci. J Bacteriol 174:5820-5826.
16. Tennant, S. M., E. L. Hartland, T. Phumoonna, D. Lyras, J. I. Rood, R. M. Robins-Browne, and I. R. van Driel. 2008. Influence of gastric acid on susceptibility to infection with ingested bacterial pathogens. Infect Immun 76:639-645.
17. Verdu, E. F., R. Fraser, D. Armstrong, and A. L. Blum. 1994. Effects of omeprazole and lansoprazole on 24-hour intragastric pH in *Helicobacter pylori*-positive volunteers. Scand J Gastroenterol 29:1065-1069.
18. Viala, J. P., S. Meresse, B. Pocachard, A. A. Guilhon, L. Aussel, and F. Barras. 2011. Sensing and adaptation to low pH mediated by inducible amino acid decarboxylases in *Salmonella*. PLoS One 6:e22397.
19. Wang, J. Y., M. F. Pasetti, F. R. Noriega, R. J. Anderson, S. S. Wasserman, J. E. Galen, M. B. Sztein, and M. M. Levine. 2001. Construction, genotypic and phenotypic characterization, and immunogenicity of attenuated ΔguaBA *Salmonella enterica* serovar *Typhi* strain CVD 915. Infect Immun 69:4734-4741.
20. Wilmes-Riesenberg, M. R., B. Bearson, J. W. Foster, and R. Curtiss, 3rd. 1996. Role of the acid tolerance response in virulence of *Salmonella typhimurium*. Infect Immun 64:1085-1092.
21. Yohannes, E., D. M. Barnhart, and J. L. Slonczewski. 2004. pH-dependent catabolic protein expression during anaerobic growth of *Escherichia coli* K-12. J Bacteriol 186:192-199.
22. Brenneman, K. E., C. Willingham, J. Kilbourne, R. Curtiss III and K. L. Roland. 2014. A low gastric pH mouse model to evaluate live attenuated bacterial vaccines. PLoS One 9:e87411.

Example 7

Urease System

Another method to increase the acid resistance of *Salmonella* vaccine strains is to introduce the Ni-dependent urease system of *Helicobacter pylori*. The urease system is a unique acid resistance strategy, different from the others described herein. *Helicobacter* survives at extremely low pH not by acid resistance (temporary halt of all metabolic activities while protons are consumed and exported away from the cell), but by acid acclimation, where the cytoplasm is buffered to almost neutral pH (pH 5-7) and metabolic processes can still occur [1]. This system is more complex than the GAD or ADI systems and involves many more gene products. Urea from the gastric fluid is allowed to enter the cell at low pH by UreI (a proton-gated urea channel) [2]. The urea is then converted to ammonia by the urease (composed of UreA and UreB) [3]. The ammonia freely diffuses into the periplasm, where it is used in conjunction with $H_2CO_3$ generated by carbonic anhydrase (named HP1186) to establish a periplasmic reservoir of bicarbonate buffer [4]. This system consumes two protons per reaction cycle, as opposed to one proton per cycle in the GAD and ADI systems. The urease system has the additional advantage of consuming protons in the periplasm (as opposed to the cytoplasm), which further protects essential cytoplasmic molecules.

The urease system involves more genes than the decarboxylase systems, and for this system, it is unlikely that all of these genes must be under the control of a regulatable promoter, only the ones that directly contribute to proton consumption (ureAB and HP1186). These genes will be introduced into the *Salmonella* chromosome under the control of a sugar-regulatable promoter such as rhaRS-$P_{rhaBAD}$. The additional components of this system, ureI—encoding the proton-gated urea channel—and ureEFGH—encoding a chaperone complex necessary to incorporate Ni ions into the urease apoenzyme [5]—will be introduced into the chromosome under the control of a constitutive promoter such as $P_I$.

REFERENCES CITED IN EXAMPLE 7

1. Sachs, G., et al., *The gastric biology of Helicobacter pylori*. Annu Rev Physiol, 2003. 65: p. 349-69.
2. Rektorschek, M., et al., *Acid resistance of Helicobacter pylori depends on the UreI membrane protein and an inner membrane proton barrier*. Mol Microbiol, 2000. 36(1): p. 141-52.
3. Labigne, A., V. Cussac, and P. Courcoux, *Shuttle cloning and nucleotide sequences of Helicobacter pylori genes responsible for urease activity*. J Bacteriol, 1991. 173(6): p. 1920-31.
4. Marcus, E. A., et al., *The periplasmic alpha-carbonic anhydrase activity of Helicobacter pylori is essential for acid acclimation*. J Bacteriol, 2005. 187(2): p. 729-38.
5. Park, J. U., et al., *Effect of the urease accessory genes on activation of the Helicobacter pylori urease apoprotein*. Mol Cells, 2005. 20(3): p. 371-7.

Example 8

The Presence of Acid Resistance Systems Increases the Immunogenicity of a Live Attenuated *Salmonella* Vaccine To investigate the effect of our system on immunogenicity, we constructed derivatives of *S. Typhimurium* ΔphoPQ strain χ8089 that carried either the $\Delta P_{adiA}$::TT araC $P_{BAD}$ adiAC or the ΔcysG::TT araC $P_{BAD}$ gadBC systems in which adiAC or gadBC expression is regulated by arabinose. Strains were grown in the presence of 0.1% arabinose and used to inoculate mice treated with histamine to induce a low gastric pH. Mice were given various doses of each strain, $1 \times 10^4$, $1 \times 10^6$ or $1 \times 10^8$ CFU. Mice were inoculated with the same dose of the same strains on days 0 and 28 (low gastric pH induced prior to both doses). Mice were challenged on day 49 with $1 \times 10^8$ CFU of wild-type *S. Typhimurium* strain χ3761 and observed for two weeks post challenge. The results (Table 3) indicated that only strains carrying the arabinose-inducible acid resistance system were protective when administered at doses of $1 \times 10^6$ CFU or $1 \times 10^8$ CFU. None were protective at the $1 \times 10^4$ dose. These results indicate that an acid-resistance system can enhance the immunogenicity of live attenuated *Salmonella* vaccines.

TABLE 3

Effect of arabinose-inducible acid resistance systems on protective efficacy of *S. Typhimurium* ΔphoPQ strains

| Strain* | Immunizing Dose (CFU) | Post challenge live/total |
|---|---|---|
| χ8089 | $1 \times 10^4$ | 0/5 |
| χ11808 | $1 \times 10^4$ | 0/5 |
| χ11789 | $1 \times 10^4$ | 1/5 |
| χ8089 | $1 \times 10^6$ | 0/5 |
| χ11808 | $1 \times 10^6$ | 3/5 |
| χ11789 | $1 \times 10^6$ | 2/5 |
| χ8089 | $1 \times 10^8$ | 0/5 |
| χ11808 | $1 \times 10^8$ | 5/5 |
| χ11789 | $1 \times 10^8$ | 5/5 |
| PBS | — | 0/5 |

*genotypes - χ8089 = ΔphoPQ
χ11808 = ΔphoPQ $\Delta P_{adiA}$::TT araC $P_{BAD}$ adiAC
χ11789 = ΔphoPQ ΔcysG::TT araC $P_{BAD}$ gadBC Mice were immunized day 0 and 28 (acid mice both times). Challenge on day 49 with $1 \times 10^8$ CFU wild-type *S. Typhimurium* χ3761. Mice observed for 21 days post challenge Example 9

Use of Acid-Resistance Systems in Probiotic Bacteria

Probiotics are live microorganisms, which may provide beneficial effects when ingested. Although the mechanisms underlying still remain poorly understood, studies have demonstrated that the probiotics can efficiently inhibit the impact of pathogens in the gut either by directly by growth competition or indirectly via production of inhibitory substances such as bacteriocins [1]. Typical probiotics such as Lactic acid bacteria, bifidobacteria, certain yeasts and bacilli have been well studied for decades and show beneficial effects on treatment of antibiotic-associated diarrhea [2], lactose intolerance [3] and colon cancer [4]. The ability of probiotics to improve host immune function [5,6], modulate inflammatory and hypersensitivity responses [5] have also been documented. The *Escherichia coli* Nissle 1917 strain has been used as a probiotic agent in human and animal medicine to treat chronic inflammatory and infectious diseases of the human and animal intestine [7].

Similar to live bacterial vaccines, probiotic strains are administered orally a must survive the low pH stomach environment in order to be effective. The regulatable acid resistance systems may serve to increase the survival of probiotic bacteria during passage through the stomach.

REFERENCES CITED IN EXAMPLE 9

1. Sanders M E. Impact of probiotics on colonizing microbiota of the gut. *J Clin Gastroenterol* 45 Suppl, S115-119 (2011).
2. D'Souza A L, Rajkumar C, Cooke J, Bulpitt C J. Probiotics in prevention of antibiotic associated diarrhoea: meta-analysis. *Bmj* 324(7350), 1361 (2002).
3. Sanders M E. Considerations for use of probiotic bacteria to modulate human health. *The Journal of nutrition* 130(2S Suppl), 384S-390S (2000).
4. Brady L J, Gallaher D D, Busta F F. The role of probiotic cultures in the prevention of colon cancer. *The Journal of nutrition* 130(2S Suppl), 410S-414S (2000).

5. Reid G, Jass J, Sebulsky M T, McCormick J K. Potential uses of probiotics in clinical practice. *Clinical microbiology reviews* 16(4), 658-672 (2003).

6. Ouwehand A C, Salminen S, Isolauri E. Probiotics: an overview of beneficial effects. *Antonie van Leeuwenhoek* 82(1-4), 279-289 (2002).

7. Kamada N, Inoue N, Hisamatsu T et al. Nonpathogenic *Escherichia coli* strain Nissle 1917 prevents murine acute and chronic colitis. *Inflammatory bowel diseases* 11(5), 455-463 (2005).

Example 10

Use of Acid Resistance Systems in a Live Attenuated *Salmonella enterica* Serovar *Gallinarum* Vaccine for Poultry

Figure 15:
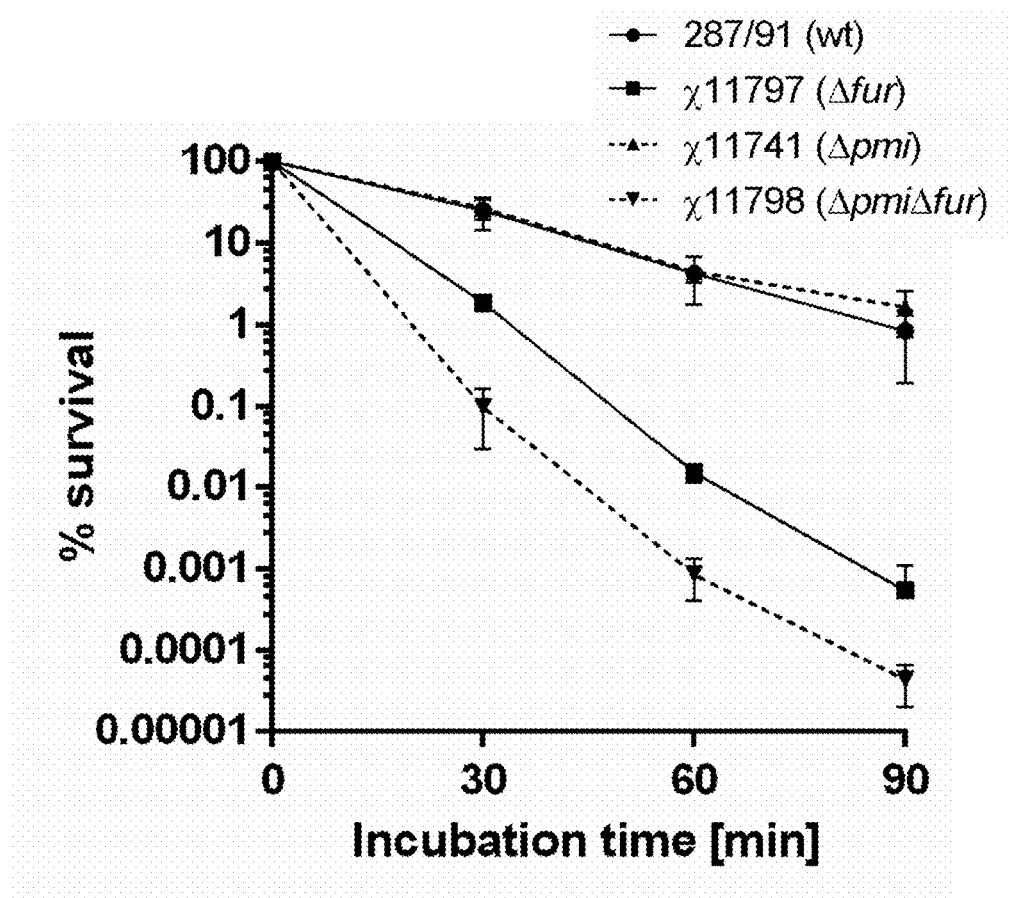
FIG. 15. Survival of *S. Gallinarum* strains during low pH challenge. Mid-log aerobic cultures grown in LB broth were harvested, washed and challenged with E medium at pH 3.0. Samples were taken and numbers of surviving cells were determined by direct plating onto LB plates. Data are presented as the mean and SEM for each time point.

*Salmonella enterica* serovar *Gallinarum* (*S. Gallinarum*) is a host-adapted pathogen that causes fowl typhoid—an important disease of poultry (1). Fowl typhoid is a septicemic disease with a typically short course and significant morbidity and mortality, which can reach as high as 100% (2). The disease occurs primarily in mature flocks, although birds of all ages may be infected. Certain mutations of *S. Gallinarum*, such as Δfur mutant χ11797 and Δfur Δpmi mutant χ11798, are effective when delivered intramuscularly, but are only partially effective when delivered orally. This discrepancy can be explained by the acid sensitivity of these strains (FIG. 15).

Thus, it may be that because the double mutant is more sensitive to low pH than the Δfur strain (FIG. 15), it does not survive as well during passage through the low pH environment of the proventriculus. If this is the case, pH sensitivity may also help to explain our conflicting results with fur mutant χ11797, which was protective when orally administered to chicks (Table 4), but was less effective when orally administered to older layers. The proventricular pH in chickens changes during the first few weeks of life, ranging from a pH of about 5 at two days of age to about 3 to 3.5 by fifteen days of age (3). Thus, it is possible that survival of strain χ11797 was greater in chicks than in the older birds used in our study. When we bypassed the gastric compartment by intramuscular injection, the χ11797 was able to elicit a protective response (Table 4). The increased acid sensitivity of χ11798 could account for its lack of immunogenicity in chicks.

Figure 16:
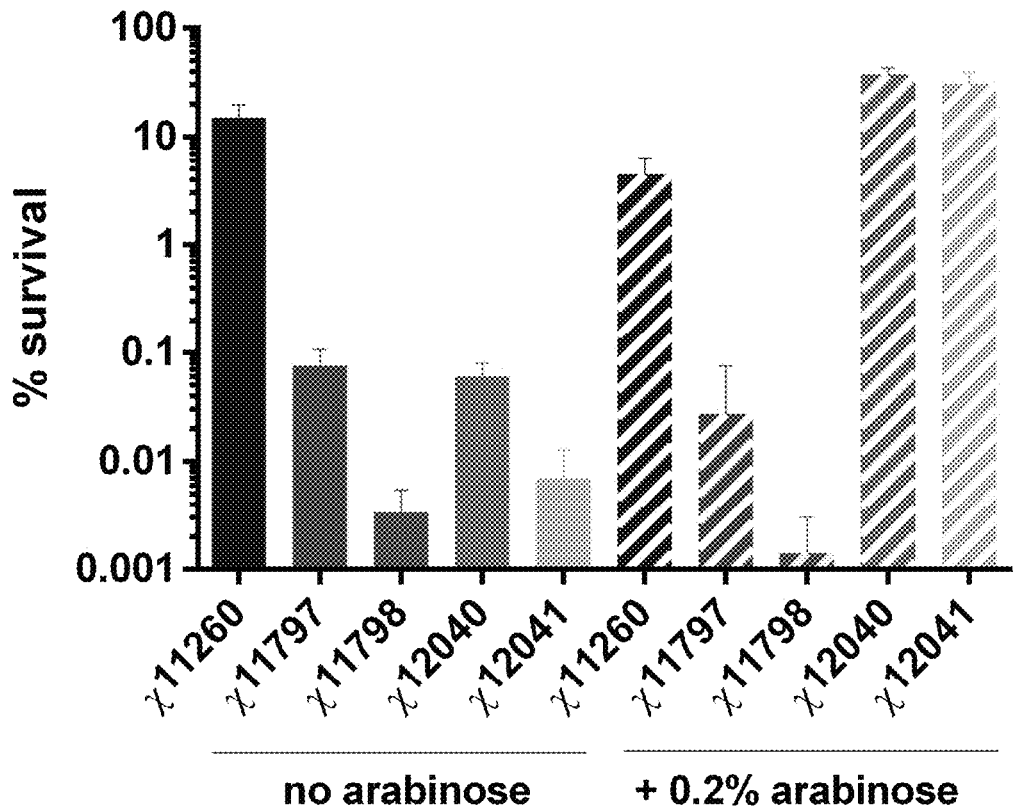

Introduction of an inducible acid resistance system can overcome this acid sensitivity. We introduced the arabinose-regulated gadBC system by introducing suicide plasmid pYA5120 (Table 1) into strains χ11797 and χ11798 by conjugation. Transconjugants are selected on LB plates with 20 µg/ml chloramphenicol. Loss of the integrated suicide plasmid is selected for on LB plates with 5% sucrose. The resulting strains derived from χ11797 and χ11798 are designated χ12040 and χ12041, respectively. When the strains are grown in the presence of 0.05% arabinose, the presence of the gadBC system increased the acid resistance of both strains to wild-type levels (FIG. 16). Thus, inclusion of the gadBC system can enhance acid resistance of *S. Gallinarum* vaccine strains.

TABLE 4

Efficacy of Δfur and Δfur Δpmi mutants as vaccines against *S. Gallinarum* challenge in chickens.

| S. Gallinarum vaccine strain | Genotype | Age of bird at vaccination | Breed | Route of vaccination | % survival |
|---|---|---|---|---|---|
| χ11797 | Δfur | 5 days | Rhode Island Red | oral | 91% |
| χ11798 | Δpmi Δfur | 5 days | Rhode Island Red | oral | 22% |
| Buffer | — | 5 days | Rhode Island Red | oral | 18% |
| χ11797 | Δfur | 7 weeks | Brown layers | oral | 50% |
| χ11797 | Δfur | 7 weeks | Brown layers | intramuscular | 100% |
| χ11798 | Δpmi Δfur | 7 weeks | Brown layers | intramuscular | 100% |
| No vaccine | | | | | 38% |

REFERENCES CITED IN EXAMPLE 10

1. Shlivaprasad H L. 2000. Fowl typhoid and pullorum disease. Rev Sci Tech 19:405-424.
2. Barrow P A, Freitas Neto O C. 2011. Pullorum disease and fowl typhoid—new thoughts on old diseases: a review. Avian Pathol 40:1-13.
3. Rynsburger J M, Classen H L. 2007. Effect of age on intestinal pH of broiler chickens, International Poultry Scientific Forum, Atlanta, Ga., USA.

Example 11

Use of Acid Resistance Systems in *Salmonella enterica* Serovar *Dublin* Vaccines

*Salmonella Dublin* is host-adapted for cattle, causing systemic infections, enteritis and abortions (1). It can also cause human disease (1). As in non-ruminants, the gastrointestinal tract of cattle is composed of low pH compartments in which acid-sensitive bacteria are killed (2). During transit through the ruminant gastrointestinal tract, *Salmonella* encounters various acidic conditions. Volatile fatty acid (VFA) concentrations are high in the rumen of grain-fed animals, and the pH may vary from 5.0 to 6.5. In these conditions, VFAs are in the undissociated form and can freely enter the bacterial cells, dissociate, and acidify the cytosol. In hay-fed animals, less fermentation occurs in the rumen, and the pH remains between 6.5 and 7. In the abomasum, *Salmonella* can encounter strongly acidic conditions, regardless of the diet, due to the presence of mineral acids, resulting in a pH below 3. Then the pH increases from the proximal part to the distal part of the small intestine, cecum and colon. Inclusion of an inducible acid resistance system into live attenuated *S. Dublin* vaccines will enhance survival during low pH encounters in orally vaccinated cattle, leading to improved immunogenicity and efficacy. Introduction of an inducible acid resistance system can be accomplished by step-wise introduction of the $\Delta P_{adiA}$::TT rhaSR $P_{rhaBAD}$ adiA using plasmid pYA5093 followed by introduction of the $\Delta(P_{adiY}\text{-adiY-}P_{adiC})$ adiC mutation using suicide plasmid pYA5072 to yield the rhamnose-regulated adiA system $\Delta P_{adiA}$::TT rhaSR $P_{rhaBAD}$ adiA $\Delta(P_{adiY}\text{-adiY-}$ $P_{adiC}$) adiC. Alternatively, the arabinose-regulated gadBC system can be introduced using plasmid pYA5120 (ΔcysG::TT araC $P_{BAD}$ gadBC).

REFERENCES CITED IN EXAMPLE 11

1. Uzzau S, Brown D J, Wallis T, Rubino S, Leori G, Bernard S, Casadesus J, Platt D J, Olsen J E. 2000. Host adapted serotypes of *Salmonella enterica*. Epidemiol Infect 125:229-255.
2. Chaucheyras-Durand F, Faqir F, Ameilbonne A, Rozand C, Martin C. 2010. Fates of acid-resistant and non-acid-resistant Shiga toxin-producing *Escherichia coli* strains in ruminant digestive contents in the absence and presence of probiotics. Appl Environ Microbiol 76:640-647.

Example 12

Survival of Vaccine Strains in Low Gastric pH Mouse Model is Enhanced by Co-Administration of Ensure® Nutrition Shake Methods. Strains used in this study are shown in Table 5. Plasmids are shown in Table 6. Six week old, female BALB/c mice (Charles River Laboratories, Wilmington, Mass., USA) were fasted without food or water for 6 h prior to the start of the experiment. Mice received the histamine $H_1$-receptor antagonist chlorpheniramine (0.3 mg/kg) subcutaneously to prevent allergy/anaphylaxis symptoms. Prior to inoculation, low gastric pH was induced by subcutaneous injection of histamine dihydrochloride (10 mg/kg). Strains were grown to late log phase (optical density at 600 nm of 0.9), then pelleted and resuspended in PBS at a concentration of $5\times10^{10}$ CFU/ml. Groups of 5 mice were orally inoculated 50 min after the administration of histamine (1). Low gastric pH was treated with sodium bicarbonate, Ensure, or nothing. Groups that were treated with bicarbonate received 40 μl of a 1.3% sodium bicarbonate solution orally 10 minutes prior to inoculation and an additional 10 μl 10 minutes after immunization. Groups that were treated with Ensure received 20 μl of Ensure® Nutrition shake (milk chocolate flavor) 10 minutes prior to inoculation and an additional 20 μl 10 minutes after immunization.

Gastric Transit Assays. Mice were inoculated as described above. Strains used in the gastric transit assays contained the low copy number plasmid pWSK129 (Kan) to allow for precise quantitation of strain numbers in the non-sterile environment of the gastrointestinal tract. Mice were euthanized 1 h after inoculation and the entire small intestine was removed, homogenized and serially diluted. Samples were plated onto LB agar containing 0.2% arabinose with kanamycin to determine the number of viable bacteria present following low pH gastric transit. The survival of the Ensure® and bicarbonate groups was compared to the control group using the Mann-Whitney test. Statistical analysis was performed by GraphPad Prism version 6.00 for Windows (GraphPad Software, La Jolla Calif. USA).

Figure 17:
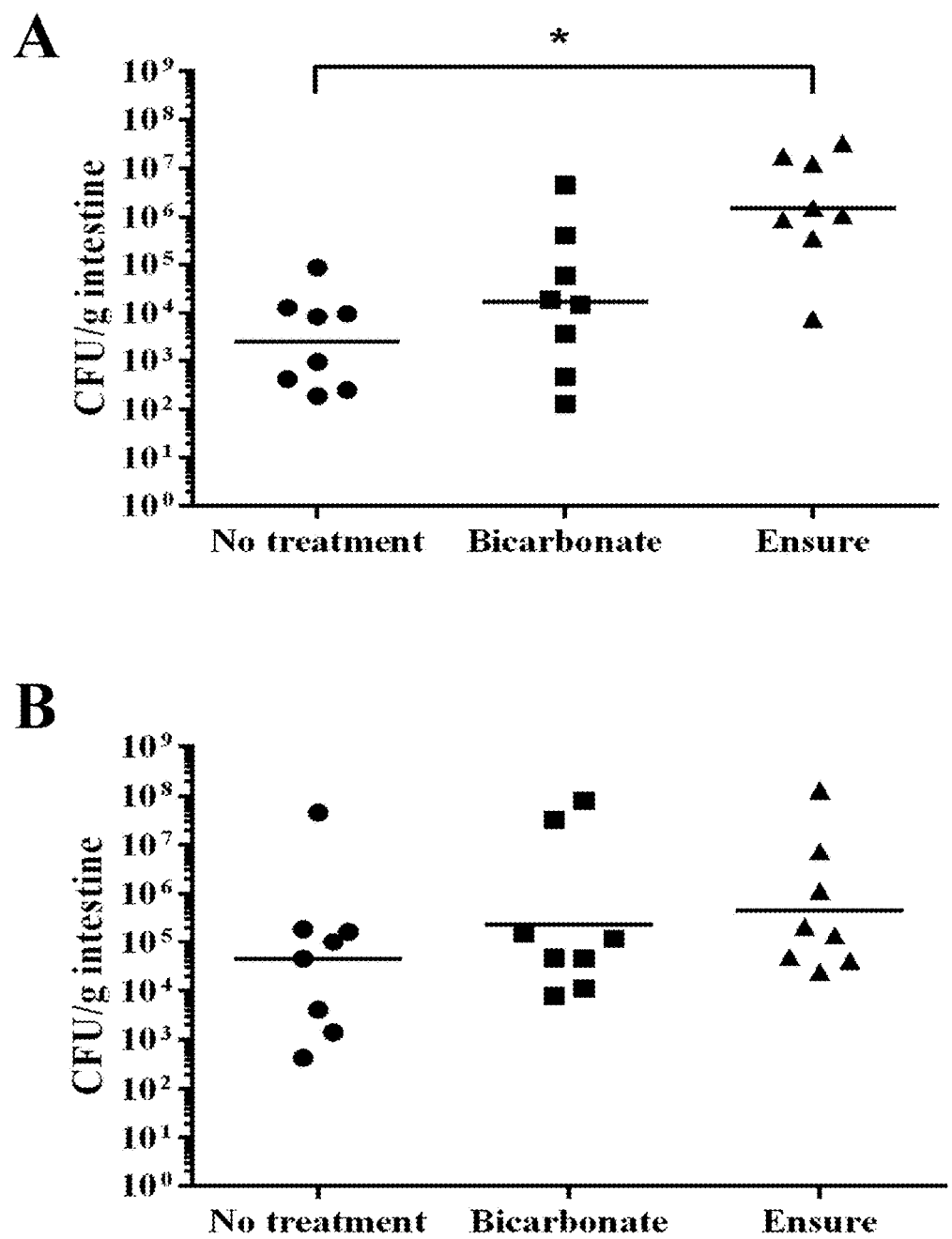
Figure 17:
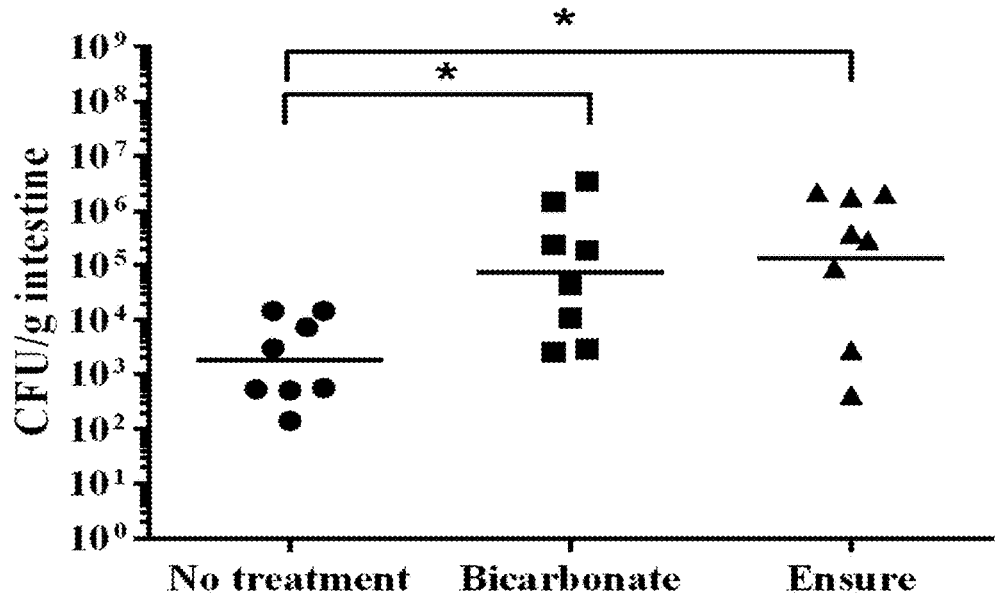
Figure 17:
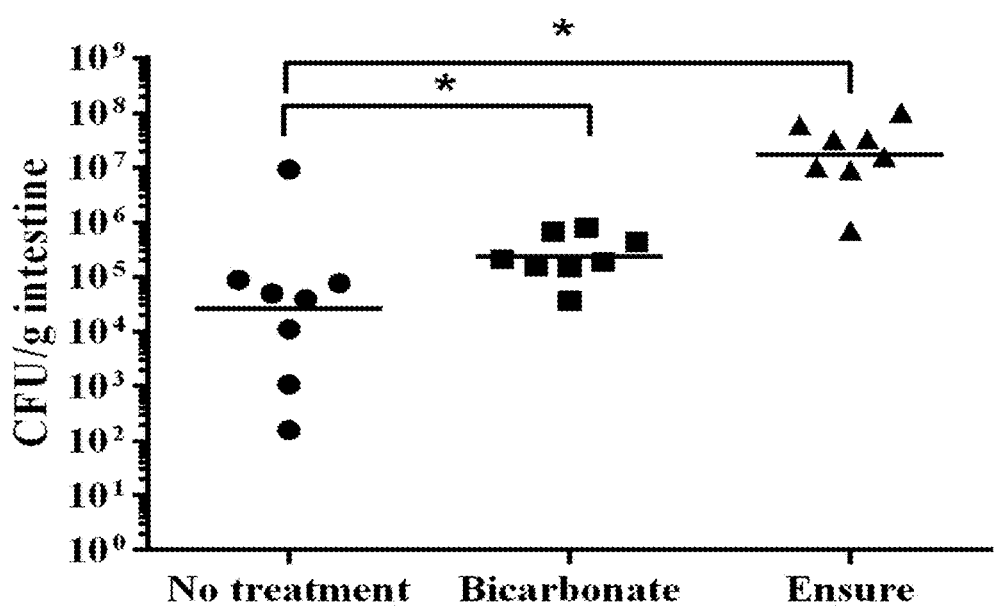

Results. To examine the ability of bicarbonate and Ensure® to combat gastric pH, these were used to buffer the stomach pH of mice. Because the gastric pH of a fasted mouse is about pH 4.0 and the gastric pH of a fasted human is about pH 1-2 (3,5,7), gastric acid secretion was induced in mice prior to immunization to better mimic the situation in humans. Using this protocol, the pH in the mouse stomach is reduced to around 1.5. Mice received either bicarbonate or Ensure® prior to and immediately following inoculation. Control mice received no treatment. Vaccine viability was measured following gastric transit (FIG. 17). For two of the three *S. Typhi* vaccine strains and the *S. Typhimurium* model strain, administration of Ensure® significantly increased the number of viable cells that reached the small intestine (p=0.0019 for χ9633 (pYA4088), p=0.0256 for χ9640 (pY4088) and p=0.0006 for χ9558 (pYA4088)). This was a 599-, 75.0- and 647-fold increase, respectively, in the geometric mean number of viable cells to reach the ileum. Administration of Ensure® prior to and following immunization did not significantly affect the ability of χ9639 (pYA4088) to transit the gastric compartment (p=0.2317), quite possibly due to the mutation in the rpoS gene which confers acid sensitivity. Bicarbonate similarly improved the survival of χ9640 (pYA4088) (p=0.0190) and χ9558 (pYA4088) (p=0.0379) during gastric transit, resulting in a 41.0- and 8.79-fold increase in the geometric mean number of cells to reach the ileum, respectively. Administration of bicarbonate did not significantly impact the survival of χ9633 (pYA4088) or χ9639 (pYA4088) (p=0.2317 and 0.4945, respectively). Overall, Ensure® worked best to protect these strains from low gastric pH. We infer that inclusion of a sugar-inducible acid resistance system such as araC $P_{BAD}$ gadBC or $\Delta P_{adiA}$::TT rhaSR $P_{rhaBAD}$ adiA $\Delta(P_{adiY}$-adiY-$P_{adiC})$-adiC, will enhance survival of these vaccines further.

TABLE 5

Strains used in gastric transit assays demonstrating protective effect of Ensure ® Nutrition shake.

| Strain | Salmonella Serovar | Genotype/Phenotype[a] | Reference |
|---|---|---|---|
| χ9558 | Typhimurium | Δpmi Δ(gmd-fcl) $\Delta P_{fur}$::TT araC $P_{BAD}$ fur $\Delta P_{crp}$::TT araC $P_{BAD}$ crp ΔasdA:TT araC $P_{BAD}$ c2 ΔaraE ΔaraBAD ΔrelA::araC $P_{BAD}$ lacI TT ΔsopB ΔagfBAC, RpoS+ | (4) |
| χ9633 | Typhi | $\Delta P_{crp}$::TT araC $P_{BAD}$ crp $\Delta P_{fur}$::TT araC $P_{BAD}$ fur Δpmi Δ(gmd-fcl) ΔsopB ΔrelA::araC $P_{BAD}$ lacI TT ΔaraE ΔaraBAD ΔtviABCDE ΔagfBAC ΔasdA, RpoS+ | (6) |
| χ9639 | Typhi | $\Delta P_{crp}$::TT araC $P_{BAD}$ crp $\Delta P_{fur}$::TT araC $P_{BAD}$ fur Δpmi Δ(gmd-fcl) ΔrelA::araC $P_{BAD}$ lacI TT ΔaraE ΔtviABCDE ΔagfBAC ΔsopB ΔasdA, RpoS− | (6) |
| χ9640 | Typhi | $\Delta P_{crp}$::TT araC $P_{BAD}$ crp $\Delta P_{fur}$::TT araC $P_{BAD}$ fur Δpmi Δ(gmd-fcl) ΔrelA::araC $P_{BAD}$ lacI TT ΔaraE ΔtviABCDE ΔagfBAC ΔsopB ΔasdA RpoS+ | (6) |

[a]In genotype descriptions, the subscripted number refers to a composite deletion and insertion of the indicated gene. P, promoter; TT, T4 ip III transcription terminator.

TABLE 6

Plasmids used in this study

| Plasmid | Description[a] | Reference |
|---|---|---|
| pWSK129 | pSC101 ori, Kan[r] | (8) |
| pYA3493 | pBR ori, Asd+ vector with bla SS-based periplasmic antigen secretion | (2) |
| pYA4088 | Encodes the α-helical region of PspA (aa 3-285) in pYA3493 | (9) |

[a]ori, replication of origin; SS, secretion signal; Kan[r], kanamycin resistance

REFERENCES CITED FOR EXAMPLE 12

1. Brenneman, K. E., C. Willingham, J. A. Kilbourne, R. Curtiss, 3rd and K. L. Roland. A low gastric pH mouse model to evaluate live attenuated bacterial vaccines. PLoS One 9: e87411.2014

2. Kang, H. Y., J. Srinivasan and R. Curtiss, 3rd. Immune responses to recombinant pneumococcal PspA antigen delivered by live attenuated *Salmonella enterica* serovar *Typhimurium* vaccine. Infect Immun 70: 1739-1749.2002
3. Kararli, T. T. Comparison of the gastrointestinal anatomy, physiology, and biochemistry of humans and commonly used laboratory animals. Biopharm Drug Dispos 16: 351-380.1995
4. L1, Y., S. Wang, G. Scarpellini, B. Gunn, W. Xin, S. Y. Wanda, K. L. Roland and R. Curtiss, 3rd. Evaluation of new generation *Salmonella enterica* serovar *Typhimurium* vaccines with regulated delayed attenuation to induce immune responses against PspA. Proc Natl Acad Sci USA 106: 593-598.2009
5. McConnell, E. L., A. W. Basit and S. Murdan. Measurements of rat and mouse gastrointestinal pH, fluid and lymphoid tissue, and implications for in-vivo experiments. J Pharm Pharmacol 60: 63-70.2008
6. Shi, H., J. Santander, K. E. Brenneman, S. Y. Wanda, S. Wang, P. Senechal, W. Sun, K. L. Roland and R. Curtiss. Live recombinant *Salmonella Typhi* vaccines constructed to investigate the role of rpoS in eliciting immunity to a heterologous antigen. PLoS One 5: e11142.2010
7. Verdu, E., F. Viani, D. Armstrong, R. Fraser, H. H. Slegrist, B. Pignatelli, J. P. Idstrom, C. Cederberg, A. L Blum and M. Fried. Effect of omeprazole on intragastric bacterial counts, nitrates, nitrites, and N-nitroso compounds. Gut 35: 455-460.1994
8. Wang, R. F. and S. R. Kushner. Construction of versatile low-copy-number vectors for cloning, sequencing and gene expression in *Escherichia coli*. Gene 100:195-199.1991
9. Xin, W., S. Y. Wanda, Y. L1, S. Wang, H. Mo and R. Curtiss, 3rd. Analysis of type II secretion of recombinant pneumococcal PspA and PspC in a *Salmonella enterica* serovar *Typhimurium* vaccine with regulated delayed antigen synthesis. Infect Immun 76: 3241-3254.2008

What is claimed is:

1. A recombinant attenuated derivative of a pathogenic enteric Salmonella bacterium comprising a nucleic acid encoding an antigen and at least one of the following:
   a) a regulatable promoter operably linked to a nucleic acid encoding a Salmonella AdiA arginine decarboxylase and a nucleic acid encoding a Salmonella AdiC arginine agmatine antiporter;
   b) a regulatable promoter operably linked to a nucleic acid encoding an E. coli GadB and/or an E. coli GadA glutamate decarboxylase and a nucleic acid encoding an E. coli GadC glutamate/γ-aminobutyric acid antiporter; or
   c) a regulatable promoter operably linked to a nucleic acid encoding a Salmonella CadA lysine decarboxylase and a nucleic acid encoding a Salmonella CadB lysine/cadaverine anti porter.

2. The recombinant bacterium of claim 1, wherein the enteric bacterium is either naturally acid sensitive or becomes more acid sensitive because of attenuating mutations, such that in the absence of induction of the regulatable promoter, the recombinant bacterium is acid sensitive, but upon induction of the regulatable promoter, the recombinant bacterium displays an increase in acid resistance.

3. The recombinant bacterium of claim 2, wherein the bacterium is acid sensitive because of a mutation in a nucleic acid sequence selected from the group consisting of rpoS, fur, phoPQ and guaBA.

4. The recombinant bacterium of claim 1, wherein the regulatable promoter is induced by a sugar.

5. The recombinant bacterium of claim 4, wherein the sugar is selected from the group consisting of arabinose and rhamnose.

6. The recombinant bacterium of claim 1, wherein the bacterium comprises at least one mutation selected from the group consisting of:
   a) $\Delta P_{adiA}$::TT araC $P_{araBAD}$ adiAC mutation;
   b) $\Delta P_{adiA}$::TT rhaSR $P_{rhaBAD}$ adiAC mutation;
   c) rhaSR $P_{rhaBAD}$ gadBC mutation;
   d) araC $P_{araBAD}$ gadBC mutation;
   e) $\Delta P_{cadB}$::TT rhaSR $P_{rhaBAD}$ cadBA mutation; and
   f) $\Delta P_{cadB}$::TT araC $P_{araBAD}$ cadBA mutation.

7. The recombinant bacterium of claim 6, wherein the bacterium further comprises at least one element selected from the group consisting of:
   a) a regulatable promoter operably linked to gadA;
   b) the cicA gene from *E. coli* transcribed from its own native promoter, a heterologous constitutive promoter or a heterologous regulatable promoter; and
   c) a Ni-dependent urease system from *H. pylori*.

8. A vaccine composition, the composition comprising a bacterium of claim 1.

* * * * *